United States Patent
Franco et al.

(10) Patent No.: US 11,445,729 B2
(45) Date of Patent: Sep. 20, 2022

(54) INOCULANTS AND METHODS FOR USE THEREOF

(71) Applicant: The Flinders University of South Australia, Bedford Park (AU)

(72) Inventors: Christopher Milton Mathew Franco, Stonyfell (AU); Hoang Xuyen Le, St. Marys (AU); Ross Alexander Ballard, Belair (AU)

(73) Assignee: The Flinders University of South Australia, Bedford Park (AU)

( * ) Notice: Subject to any disclaimer, the term of this patent is extended or adjusted under 35 U.S.C. 154(b) by 406 days.

(21) Appl. No.: 16/541,834

(22) Filed: Aug. 15, 2019

(65) Prior Publication Data

US 2020/0037528 A1    Feb. 6, 2020

Related U.S. Application Data

(62) Division of application No. 15/320,301, filed as application No. PCT/AU2015/000360 on Jun. 19, 2015, now Pat. No. 10,462,990.

(30) Foreign Application Priority Data

Jun. 20, 2014 (AW) ............................. 2014902374

(51) Int. Cl.
| | |
|---|---|
| C12N 1/20 | (2006.01) |
| C12N 15/82 | (2006.01) |
| A01N 63/28 | (2020.01) |
| A01N 63/20 | (2020.01) |
| A01H 3/00 | (2006.01) |
| C12R 1/465 | (2006.01) |

(52) U.S. Cl.
CPC ............ *A01N 63/28* (2020.01); *A01H 3/00* (2013.01); *A01N 63/20* (2020.01); *C12N 1/20* (2013.01); *C12N 1/205* (2021.05); *C12N 15/8261* (2013.01); *C12N 15/8279* (2013.01); *C12R 2001/465* (2021.05)

(58) Field of Classification Search
CPC .............................. A01N 63/00; A01N 63/28
See application file for complete search history.

(56) References Cited

U.S. PATENT DOCUMENTS

| | | |
|---|---|---|
| 2,200,532 A | 5/1940 | Bond |
| 4,940,834 A | 7/1990 | Hurley et al. |
| 5,041,290 A | 8/1991 | Gindrat et al. |
| 5,113,619 A | 5/1992 | Leps et al. |
| 5,229,291 A | 7/1993 | Nielsen et al. |
| 5,292,507 A | 3/1994 | Charley |
| 5,415,672 A | 5/1995 | Fahey et al. |
| 5,730,973 A | 3/1998 | Morales et al. |
| 5,919,447 A | 7/1999 | Marrone et al. |
| 5,994,117 A | 11/1999 | Bacon et al. |
| 6,072,107 A | 6/2000 | Latch et al. |
| 6,077,505 A | 6/2000 | Parke et al. |
| 6,337,431 B1 | 1/2002 | Tricoli et al. |
| 6,495,133 B1 | 12/2002 | Xue |
| 6,602,500 B1 | 8/2003 | Kharbanda et al. |
| 6,681,186 B1 | 1/2004 | Denisov et al. |
| 6,689,880 B2 | 2/2004 | Chen et al. |
| 6,823,623 B2 | 11/2004 | Minato et al. |
| 7,037,879 B2 | 5/2006 | Imada et al. |
| 7,084,331 B2 | 8/2006 | Isawa et al. |
| 7,335,816 B2 | 2/2008 | Kraus et al. |
| 7,341,868 B2 | 3/2008 | Chopade et al. |
| 7,485,451 B2 | 2/2009 | VanderGheynst et al. |
| 7,555,990 B2 | 7/2009 | Beaujot |
| 7,632,985 B2 | 12/2009 | Malven et al. |
| 7,763,420 B2 | 7/2010 | Stritzker et al. |
| 7,906,313 B2 | 3/2011 | Henson et al. |
| 7,977,550 B2 | 7/2011 | West et al. |
| 8,143,045 B2 | 3/2012 | Miasnikov et al. |
| 8,455,198 B2 | 6/2013 | Gao et al. |
| 8,455,395 B2 | 6/2013 | Miller et al. |
| 8,465,963 B2 | 6/2013 | Rolston et al. |
| 8,728,459 B2 | 5/2014 | Isawa et al. |
| 8,975,489 B2 | 3/2015 | Craven |
| 9,049,814 B2 | 6/2015 | Marx et al. |

(Continued)

FOREIGN PATENT DOCUMENTS

| | | |
|---|---|---|
| CA | 1041788 A | 11/1978 |
| CA | 1229497 A | 11/1987 |

(Continued)

OTHER PUBLICATIONS

Misk, Azza, and Christopher Franco. "Biocontrol of chickpea root rot using endophytic actinobacteria." BioControl 56.5 (2011): 811-822. (Year: 2011).*

Conn, V. M., "Effect of Microbial Inoculants on the Indigenous Actinobacterial Endophyte Population in the Roots of Wheats as Determined by Terminal Restriction Fragment Length Polymorphism," Applied and Environmental Microbiology, 2004, pp. 6407-6413, vol. 70, No. 11.

Darsonval, A., et al., "Adhesion and Fitness in the Bean Phyllosphere and Transmission to Seed of *Xanthomonas fuscans* subsp. *fuscans*," Molecular Plant-Microbe Interactions, 2009, pp. 747-757, vol. 22, No. 6.

(Continued)

*Primary Examiner* — Weihua Fan
(74) *Attorney, Agent, or Firm* — Goodwin Procter LLP

(57) ABSTRACT

The present invention relates to methods for enhancing at least one growth parameter of a leguminous plant via co-inoculation of a leguminous plant with at least one rhizobial microorganism together with at least one actinobacterial microorganism. In further aspects, the present invention also relates to leguminous plants co-inoculated with at least one rhizobial microorganism together with at least one actinobacterial microorganism, as well as specific actinobacterial strains and inoculant compositions which are useful in accordance with the present invention.

27 Claims, 9 Drawing Sheets

Specification includes a Sequence Listing.

(56) References Cited

U.S. PATENT DOCUMENTS

| | | |
|---|---|---|
| 9,113,636 B2 | 8/2015 | von Maltzahn et al. |
| 9,277,751 B2 | 3/2016 | Sword |
| 9,288,995 B2 | 3/2016 | von Maltzahn et al. |
| 9,295,263 B2 | 3/2016 | von Maltzahn et al. |
| 9,364,005 B2 | 6/2016 | Mitter et al. |
| 9,408,394 B2 | 8/2016 | von Maltzahn et al. |
| 9,532,572 B2 | 1/2017 | von Maltzahn et al. |
| 9,532,573 B2 | 1/2017 | von Maltzahn et al. |
| 9,545,111 B2 | 1/2017 | Sword |
| 9,622,485 B2 | 4/2017 | von Maltzahn et al. |
| 9,652,840 B1 | 5/2017 | Shriver et al. |
| 9,687,001 B2 | 6/2017 | Vujanovic et al. |
| 9,756,865 B2 | 9/2017 | Sword |
| 10,058,101 B2 | 8/2018 | von Maltzahn et al. |
| 10,076,120 B2 | 9/2018 | von Maltzahn et al. |
| 10,104,862 B2 | 10/2018 | Vujanovic et al. |
| 10,136,646 B2 | 11/2018 | Von Maltzahn et al. |
| 10,212,912 B2 | 2/2019 | Vujanovic et al. |
| 10,306,890 B2 | 6/2019 | Mitter et al. |
| 10,362,787 B2 | 7/2019 | Mitter et al. |
| 10,499,652 B2 | 12/2019 | von Maltzahn et al. |
| 10,499,653 B2 | 12/2019 | von Maltzahn et al. |
| 10,499,654 B2 | 12/2019 | von Maltzahn et al. |
| 10,667,523 B2 | 6/2020 | Ambrose et al. |
| 11,151,379 B2 | 10/2021 | Freitag et al. |
| 2002/0142917 A1 | 10/2002 | Triplett et al. |
| 2005/0070435 A1 | 3/2005 | Chopade et al. |
| 2005/0072047 A1 | 4/2005 | Conkling et al. |
| 2006/0046246 A1 | 3/2006 | Zeng et al. |
| 2006/0178269 A1 | 8/2006 | Medina-Vega |
| 2006/0185207 A1 | 8/2006 | Mitcheltree |
| 2007/0028318 A1 | 2/2007 | Livore et al. |
| 2007/0055456 A1 | 3/2007 | Raftery et al. |
| 2007/0142226 A1 | 6/2007 | Franco |
| 2007/0292953 A1 | 12/2007 | Mankin et al. |
| 2008/0229441 A1 | 9/2008 | Young et al. |
| 2008/0289060 A1 | 11/2008 | De Beuckeleer et al. |
| 2009/0155214 A1 | 6/2009 | Isawa et al. |
| 2009/0300781 A1 | 12/2009 | Bancroft et al. |
| 2010/0064392 A1 | 3/2010 | Yang et al. |
| 2010/0095396 A1 | 4/2010 | Voeste et al. |
| 2010/0205690 A1 | 8/2010 | Biasing et al. |
| 2010/0227357 A1 | 9/2010 | Redman et al. |
| 2011/0182862 A1 | 7/2011 | Green et al. |
| 2011/0195406 A1 | 8/2011 | Sorenson et al. |
| 2012/0108431 A1 | 5/2012 | Williams et al. |
| 2012/0131696 A1 | 5/2012 | Aayal et al. |
| 2012/0144533 A1 | 6/2012 | Craven |
| 2012/0149571 A1 | 6/2012 | Kloepper et al. |
| 2012/0178624 A1 | 7/2012 | Kaminskyj et al. |
| 2012/0324599 A1 | 12/2012 | Kerns et al. |
| 2013/0031673 A1 | 1/2013 | Grandlic et al. |
| 2013/0071425 A1 | 3/2013 | Vidal et al. |
| 2013/0079225 A1 | 3/2013 | Smith et al. |
| 2013/0150240 A1 | 6/2013 | Newman et al. |
| 2013/0233501 A1 | 9/2013 | Van Zyl et al. |
| 2014/0020136 A1 | 1/2014 | Van Der Wolf et al. |
| 2014/0109249 A1 | 4/2014 | Turner et al. |
| 2014/0115731 A1 | 4/2014 | Turner et al. |
| 2014/0134629 A1 | 5/2014 | Turner et al. |
| 2014/0147425 A1 | 5/2014 | Henn et al. |
| 2014/0342905 A1 | 11/2014 | Bullis et al. |
| 2015/0020239 A1 | 1/2015 | von Maltzahn et al. |
| 2015/0033420 A1 | 1/2015 | Rodriguez et al. |
| 2015/0126365 A1 | 5/2015 | Sword |
| 2015/0230478 A1 | 8/2015 | Vujanovic et al. |
| 2015/0242970 A1 | 8/2015 | Avey et al. |
| 2015/0320050 A1 | 11/2015 | von Maltzahn et al. |
| 2015/0335029 A1 | 11/2015 | Mitter et al. |
| 2015/0366217 A1 | 12/2015 | Vujanovic et al. |
| 2015/0368607 A1 | 12/2015 | Arnold et al. |
| 2015/0370935 A1 | 12/2015 | Starr |
| 2015/0373993 A1 | 12/2015 | von Maltzahn et al. |
| 2016/0021891 A1 | 1/2016 | von Maltzahn et al. |
| 2016/0150796 A1 | 6/2016 | von Maltzahn et al. |
| 2016/0174570 A1 | 6/2016 | Vujanovic et al. |
| 2016/0192662 A1 | 7/2016 | Sword |
| 2016/0205947 A1 | 7/2016 | Sword |
| 2016/0235074 A1 | 8/2016 | von Maltzahn et al. |
| 2016/0255844 A1 | 9/2016 | Mitter et al. |
| 2016/0260021 A1 | 9/2016 | Marek |
| 2016/0286821 A1 | 10/2016 | Sword |
| 2016/0290918 A1 | 10/2016 | Xu et al. |
| 2016/0316760 A1 | 11/2016 | Ambrose et al. |
| 2016/0316763 A1 | 11/2016 | Sword |
| 2016/0330976 A1 | 11/2016 | Mitter et al. |
| 2016/0338360 A1 | 11/2016 | Mitter et al. |
| 2016/0366892 A1 | 12/2016 | Ambrose et al. |
| 2017/0020138 A1 | 1/2017 | Von Maltzahn et al. |
| 2017/0161560 A1 | 6/2017 | Itzhaky et al. |
| 2017/0164619 A1 | 6/2017 | von Maltzahn et al. |
| 2017/0164620 A1 | 6/2017 | von Maltzahn et al. |
| 2017/0215358 A1 | 8/2017 | Franco et al. |
| 2017/0223967 A1 | 8/2017 | Mitter et al. |
| 2018/0020677 A1 | 1/2018 | Ambrose et al. |
| 2018/0092365 A1 | 4/2018 | Sword |
| 2018/0153174 A1 | 6/2018 | Riley et al. |
| 2018/0177196 A1 | 6/2018 | Sword |
| 2018/0189564 A1 | 7/2018 | Freitag et al. |
| 2018/0213800 A1 | 8/2018 | Djonovic et al. |
| 2018/0249716 A1 | 9/2018 | Riley |
| 2018/0251776 A1 | 9/2018 | Riley |
| 2019/0130999 A1 | 5/2019 | Oppenheim et al. |
| 2021/0372997 A1 | 12/2021 | Von Maltzahn et al. |

FOREIGN PATENT DOCUMENTS

| | | |
|---|---|---|
| CA | 2562175 A1 | 4/2008 |
| CA | 2916678 A1 | 12/2014 |
| CA | 2960032 A1 | 3/2015 |
| CA | 2935218 A1 | 7/2015 |
| CA | 2953466 A1 | 12/2015 |
| CA | 2953697 A1 | 12/2015 |
| CN | 1604732 A | 4/2005 |
| CN | 1948459 A | 4/2007 |
| CN | 101311262 A | 11/2008 |
| CN | 101423810 A | 5/2009 |
| CN | 101570738 A | 11/2009 |
| CN | 101693881 A | 4/2010 |
| CN | 102010835 A | 4/2011 |
| CN | 102123596 A | 7/2011 |
| CN | 102168022 A | 8/2011 |
| CN | 102352327 A | 2/2012 |
| CN | 102533601 A | 7/2012 |
| CN | 103642725 A | 3/2014 |
| CN | 103865837 | 6/2014 |
| CN | 104250616 A | 12/2014 |
| CN | 104388356 A | 3/2015 |
| CN | 104560742 A | 4/2015 |
| CN | 105886428 | 8/2016 |
| CN | 106434493 | 2/2017 |
| EP | 0192342 A2 | 8/1986 |
| EP | 0223662 A1 | 5/1987 |
| EP | 0378000 A2 | 7/1990 |
| EP | 0494802 A1 | 7/1992 |
| EP | 0818135 A1 | 1/1998 |
| EP | 1621632 A1 | 2/2006 |
| EP | 1935245 A1 | 6/2008 |
| EP | 2676536 A1 | 12/2013 |
| JP | 2003300804 A | 10/2003 |
| JP | 2009/072168 A | 4/2009 |
| KR | 20050039979 | 5/2005 |
| KR | 20100114806 A | 10/2010 |
| KR | 101066283 | 9/2011 |
| KR | 101091151 B1 | 12/2011 |
| KR | 20130023491 A | 3/2013 |
| RU | 2043028 C1 | 9/1995 |
| WO | 1988/009114 | 1/1988 |
| WO | 1994/016076 | 7/1994 |
| WO | 98/35017 | 8/1998 |
| WO | 99/59412 | 11/1999 |
| WO | 2000/029607 A1 | 5/2000 |
| WO | 2001/083697 A2 | 11/2001 |
| WO | 2001/083818 A2 | 11/2001 |

(56) References Cited

FOREIGN PATENT DOCUMENTS

| | | |
|---|---|---|
| WO | 2002/065836 A2 | 8/2002 |
| WO | 2004/046357 A1 | 6/2004 |
| WO | 2005/003328 A1 | 1/2005 |
| WO | 2007/021200 A1 | 2/2007 |
| WO | 2007/107000 A1 | 9/2007 |
| WO | 2008/103422 A2 | 8/2008 |
| WO | 2009/012480 A2 | 1/2009 |
| WO | 2009/078710 A1 | 6/2009 |
| WO | 2009/126473 A1 | 10/2009 |
| WO | 2010/109436 A1 | 9/2010 |
| WO | 2010/115156 A2 | 10/2010 |
| WO | 2011/001127 A1 | 1/2011 |
| WO | 2011/011627 A1 | 1/2011 |
| WO | 2011/082455 A1 | 7/2011 |
| WO | 2011/112781 A2 | 9/2011 |
| WO | 2011/117351 A1 | 9/2011 |
| WO | 2012/016140 | 2/2012 |
| WO | 2012/034996 A1 | 3/2012 |
| WO | 2013/016361 A2 | 1/2013 |
| WO | 2013/029112 A1 | 3/2013 |
| WO | 2013/090628 A1 | 6/2013 |
| WO | 2013/122473 A1 | 8/2013 |
| WO | 2013/177615 A1 | 12/2013 |
| WO | 2013/190082 A1 | 12/2013 |
| WO | 2014/046553 A1 | 3/2014 |
| WO | 2014/082950 A1 | 6/2014 |
| WO | 2014/121366 A1 | 8/2014 |
| WO | 2014/206953 A1 | 12/2014 |
| WO | 2014/210372 A1 | 12/2014 |
| WO | 2015/035099 A1 | 3/2015 |
| WO | 2015/069938 A1 | 5/2015 |
| WO | 2015/100431 A2 | 7/2015 |
| WO | 2015/100432 A2 | 7/2015 |
| WO | 2015/114552 | 8/2015 |
| WO | 2015/192172 A1 | 12/2015 |
| WO | 2015/200852 A2 | 12/2015 |
| WO | 2015/200902 A2 | 12/2015 |
| WO | 2016/057991 A1 | 4/2016 |
| WO | 2016/090212 A1 | 6/2016 |
| WO | 2016/109758 A2 | 7/2016 |
| WO | 2016/179046 A1 | 11/2016 |
| WO | 2016/179047 A1 | 11/2016 |
| WO | 2016/200987 A1 | 12/2016 |
| WO | 2018094027 | 5/2018 |
| WO | 2018102733 A1 | 6/2018 |
| WO | 2018160244 A1 | 9/2018 |
| WO | 2018160245 A1 | 9/2018 |
| WO | 2019/046909 | 3/2019 |
| WO | 2019084380 | 5/2019 |
| WO | 2019113468 | 6/2019 |

OTHER PUBLICATIONS

Edgar, R. C., "UPARSE: Highly Accurate OTU Sequences From Microbial Amplicon Reads," Nat. Methods, 2013, pp. 996-998, vol. 10, No. 10.

Gu, O., et al., "*Glycomyces sambucus* sp. nov., an endophytic actinomycete islolated from the stem of Sambucus adnata Wall," International Journal of Systematic and Evolutionary Microbiology, 2007, pp. 1995-1998, vol. 57.

Hardoim, P.R., et al., "Dynamics of Seed-Borne Rice Endophytes on Early Plant Growth Stages," PLoS ONE, 2012, vol. 7, No. 2, 13 Pages.

Kasana, R. C., et al., "A Rapid and Easy Method for the Detection of Microbial Cellulases on Agar Plates Using Gram's Iodine," Curr Microbiol., 2008, pp. 503-507, vol. 57.

Lundberg, D.S., et al., "Defining the Core *Arabidopsis thaliana* Root Microbiome," Nature, 2012, pp. 86-90, vol. 488, No. 7409.

Hanshew, A., et al., "Characterization of Actinobacteria Associated with Three Ant-Plant Mutualisms", Microbiol Ecology, Aug. 6, 2014, vol. 69, No. 1, pp. 192-203.

Langille, M.G.I. et al., "Predictive functional profiling of microbial communities using 16S rRNA marker; gene sequences," Nature Biotechnology, 2013, vol. 31, No. 9, pp. 814-821.

Li, M., et al., "ATP Modulates the Growth of Specific Microbial Strains", Current Microbiology, May 30, 2010, vol. 62, No. 1, pp. 84-89.

PCT Invitation to Pay Additional Fees, PCT Application No. PCT/US2017/064351, dated Feb. 9, 2018, 18 Pages.

PCT International Search Report and Written Opinion, PCT Application No. PCT/US2017/064351, dated Apr. 9, 2018, 25 Pages.

PCT Invitation to Pay Additional Fees, PCT Application No. PCT/US2017/064361, dated Mar. 7, 2018, 18 Pages.

European Patent Office, Supplementary European Search Report for European Patent Application No. 15810847.2, dated Feb. 28, 2018, 19 Pages.

European Patent Office, Extended European Search Report, European Patent Application No. EP 15812324.0, dated Feb. 21, 2018, 23 Pages.

European Patent Office, Extended European Search Report, European Patent Application No. EP 15809264.3, dated Mar. 12, 2018, 14 Pages.

NCBI GenBank: CP000653.1 "*Enterobacter* sp. 638, complete genome" ASM1632v1, Apr. 18, 2007, 2 Pages, Can be retrieved at <URL:https://www.ncbi.nlm.nih.gov/assembly/GCA000016325.1>.

NCBI GenBank: EBI accession No. EM STD:JQ759988, "*Dothideomycetes* sp. genotype 226 isolate FL0175 internal transcribed spacer 1, partial sequence; 5.8S ribosomal RNA gene and internal transcribed spacer 2, complete sequence; and 28S ribosomal RNA gene, partial sequence," May 17, 2012, 2 Pages.

GenBank: JN210900.1, "*Enterobacter* sp. WS05 16S ribosomal RNA gene, partial sequence," NCBI, Sep. 24, 2012, 1 Page, can be retrieved at<URL:https://www.ncbi.nlm.nih.gov/nuccore/jn210900>.

PCT International Search Report and Written Opinion for PCT/US2017/064361, dated May 11, 2018, 22 Pages.

PCT International Search Report and Written Opinion, PCT Application No. PCT/US2017/064292, dated May 11, 2018, 20 Pages.

European Patent Office, Extended European Search Report, European Patent Application No. EP 15876324.3, dated Jun. 12, 2018, 9 Pages.

Vujanovic, V., et al., "A comparative study of endophytic mycobiota in leaves of Acer saccharum in eastern North America," Mycological Progress, May 2002, pp. 147-154, vol. 1, Issue 2.

United States Patent Office, Non-Final Office Action, U.S. Appl. No. 14/766,065, filed Oct. 27, 2017, 11 Pages.

Cha, C., et al., "Production of Acyl-Homoserine Lactone Quorum-Sensing Signals by Gram-Negative Plant Associated Bacteria," Mol Plant Microbe Interact., 1998, pp. 1119-1129, vol. 11, No. 11.

Chernin, L. S., et al., "Chitinolytic Activity in Chromobacterium violaceum: Substrate Analysis and Regulation by Quorum Sensing," J Bacteriol, 1998, pp. 4435-4441, vol. 180, No. 17.

Hain, T., et al., "Chitinolytic transgenes from Streptomyces albidoflavus as phytochemicals defences against herbivorous insects, use in transgenic plants and effect in plant development", International Journal of Systematic Bacteriology, Jan. 1997, vol. 47, No. 1, pp. 202-206.

Johnston-Monje, D., "Microbial Ecology of Endophytic Bacteria in Zea Species as Influenced by Plant Genotype, Seed Origin, and Soil Environment," Thesis, University of Guelph, 2011, 230 Pages.

Orakçi Ge et al, "Selection of antagonistic actinomycete isolates as biocontrol agents against root-rot fungi", Fresenius Environmental Bulletin, 2010, 19:417-424 & GenBank Accession No. GQ475299, Oct. 5, 2009.

R Core Team, "R: A Language and Environment for Statistical Computing," R Foundation for Statistical Computing, Vienna, Austria, May 2013, ISBN: 3-900051-07-0. Available online at http://www.R-25project.org/, 3604 Pages.

NCBI, GenBankAccession No. KX641980.1, Jul. 29, 2017, Scott, M., et al., "*Dothideomycetes* sp. isolate FT14-6 internal transcribed spacer 1, partial sequence; 5.8S ribosomal RNA gene and internal transcribed spacer 2, complete sequence; and large subunit ribosomal RNA gene, partial sequence," 2 Pages, Can be retrieved at<URL:https://www.ncbi.nlm.nih.gov/nuccore/KX641980>.

(56) References Cited

OTHER PUBLICATIONS

Weaver, P.F., et al., "Characterization of Rhodopseudomonas capsulata," Arch Microbiol., 1975, pp. 207-216, vol. 105.

Redman, R. S., et al.,"Thermotolerance Generated by Plant/Fungal Symbiosis," Science, Nov. 2002, vol. 298, 1 Page (with 4 pages of supplemental material).

You, Y., et al., "Analysis of Genomic Diversity of Endophytic Fungal Strains Isolated from the Roots of Suaeda japonica and S. maritima for the Restoration of Ecosystems in Buan Salt Marsh," Korean Journal of Microbiology and Biotechnology, 2012, pp. 287-295, vol. 40, No. 4. (with English Abstract).

Invitation to Pay Additional Fees, PCT Application No. PCT/CA2013/000091, dated Mar. 27, 2013, 2 Pages.

International Search Report and Written Opinion for PCT/EP2013/062976, dated Dec. 22, 2014, 9 Pages.

International Search Report and Written Opinion, Application No. PCT/US2014/054160, dated Dec. 9, 2014, 21 Pages.

Invitation to Pay Additional Fees, PCT Application No. PCT/US2014/064411, dated Feb. 5, 2015, 2 Pages.

International Search Report and Written Opinion, International Application No. PCT/US2014/064411, dated Mar. 27, 2015, 15 Pages.

International Search Report and Written Opinion, International Application No. PCT/US2014/072399, dated Jun. 26, 2015, 22 Pages.

Invitation to Pay Additional Fees, PCT Application No. PCT/US2014/072400, dated Apr. 16, 2015, 6 Pages.

International Search Report and Written Opinion, Application No. PCT/US2014/072400, dated Jul. 8, 2015, 38 Pages.

Abarenkov, K., et al., "PlutoF—A Web Based Workbench for Ecological and Taxonomic Research, with an Online Implementation for Fungal ITS Sequences," Evol Bioinform Online, 2010, pp. 189-196, vol. 6.

Castillo, D., et al., "Fungal Endophytes: Plant Protective Agents Against Herbivores," Power Point Presentation dated Aug. 4, 2013.

Hiatt, E.E., et al., "Tall Fescue Endophyte Detection: Commerical Immunoblot Test Kit Compared with Microscopic Analysis," Crop Science, 1999, pp. 796-799, vol. 39.

Johnston-Monje, D., et al., "Conservation and Diversity of Seed Associated Endophytes in *Zea* Across Boundaries of Evolution, Ethnography and Ecology," PLoS ONE, 2011, vol. 6, No. 6, 22 Pages.

Pedraza, R.O., et al., "Azospirillum inoculation and nitrogen fertilization effect on grain yield and on the diversity of endophytic bacteria in the phyllosphere of rice rainfed crop," European Journal of Soil Biology, 2009, pp. 36-43, vol. 45.

Welty, R.E., et al., "Influence of Moisture Content, Temperature, and Length of Storage onSeed Germination and Survival of Endophytic Fungi in Seeds of Tall Fescue and Perennial Ryegrass," Phytopathyol., 1987, pp. 893-900, vol. 77, No. 6.

Xue, Q.Y., et al., "Evaluation of the Strains of Acinetobacter and Enterobacter as potential Biocontrol Agents Against Ralstonia Wilt of Tomato," Biological Control, 2009, vol. 48, pp. 252-258.

Li, Q., "Agrobacterium tumefaciens Strain TA-AT-10 16S Ribosomal RNA Gene, Partial Sequence: GenBank: KF673157.1," Submitted Dec. 16, 2013.

PCT International Search Report and Written Opinion for PCT/AU2018/050387, dated Jul. 12, 2018, 8 pages.

PCT International Search Report and Written Opinionfor PCT/US2018/051467, dated Mar. 25, 2019 26 pages.

Al-Askar AA, "Microbiological studies on the in vitro inhibitory effect of Streptomyces collinus albescens against some phytopathogenic fungi", African Journal of Microbiology Research, 2012, 6: 3277-3283 & GenBank Accession No. AB184101, May 20, 2008.

Ardakani, M.R. et al., "Absorption of N, P, K thorugh triple inoculation of wheat (*Triticum aestivum* L.) by *Azospirillurr brasilense*, *Streptomyces* sp., Glomus intraradices and manure application," Physiol Mol Biol Plants, 2011, vol. 17, No. 2, pp. 181-192.

Barnett, S., et al., "Selection of microbes for control of Rhizoctonia root rot on wheat using a high throughput pathosystem". Biological Control, Jul. 6, 2017, 113: 45-57.

Bashan, Yoav Ed, et al., "Inoculants of plant growth-promoting bacteria for use in agriculture," Biotechnology Advances, Elsevier Publishing, Barking, GB, vol. 16, No. 4, Jul. 1, 1998, pp. 729-770, XP004123985.

Bashan, Yoav E., et al., "Alginate Beads as Synthetic Inoculant Carriers for Slow Release of Bacteria that Affect Plant Growth," Applied and Environmental Microbiology, pp. 1089-1098, May 1986.

Shenhua Li, et al., "Change in deep soil microbial communities due to long-term fertilization," Soil Biology and Biochemistry, vol. 75, Mar. 5, 2014, pp. 264-272, XP055530941.

Cheow, W.S., et al., "Biofilm-like Lactobacillus rhamnosus Probiotices Encapsulated in Algiinate and Carrageenan Microcapsules Exhibiting Enhanced Thermotolerance and Freeze-drying Resistance," Biomacromolecules 2013, vol. 14(9):3214-3222.

De Santi, M. et al., "A combined morphologic and molecular approach for characterizing fungal microflora from a traditional Italian cheese (Fossa cheese)," Inter: Dairy J., 2010, vol. 10, No. 7, pp. 465-471.

Fatima Z et al, "Antifungal activity of plant growth-promoting rhizobacteria isolates against Rhizoctonia solani in wheat", African Journal of Biotechnology, 2009, 8:219-225.

GenBank Accession No. KY643705, Feb. 27, 2017.
GenBank Accession No. KF951483, Jan. 5, 2014.
GenBank Accession No. KJ152029, May 6, 2015.
GenBank Accession No. KJ162248, Apr. 8, 2014.

Govindarajan, M. et al., "Effects of the Inoculation of Burkholderia vietnamensis and Related Endophytic Diaztrophic Bacteria on Grain Yield of Rice", Microbiol Ecology, Apr. 4, 2007, 17 Pages.

Iverson, C., et al, "The taxonomy of Enterobacter sakazakii: proposal of a new genus *Cronobacter* gen. nov. and descriptions of *Cronobacter sakazakii* comb. nov. *Cronobacter sakazakii* subsp. *sakazakii*, comb, nov., *Cronobacter sakazakii* subsp. *malonaticus* subsp. nov., *Cronobacter turicensis* sp. nov., *Cronobacter muytjensii* sp. nov., *Cronobacter dublinensis* sp. nov. and *Cronobacter* genomospecies I", BMC Evolutionary Biology 2007, Apr. 17, 2017, 11 pages.

Joe, M.M. et al., "Development of alginate-based aggregate inoculants of *Methylobacterium* sp. And Azospirillum prasilense tested under in vitro conditions to promote plant growth," Journal of Applied Microbiology 2013, 116 (2):408-423, XP055225426, Nov. 22, 2013.

Manoharan, M. J. et al., "Survival of flocculated cells in alginate and its inoculatin effect on growth and yield of naize underwater deficit conditions," EP J of Soil Biology, Gauthier-Villars, Montrouge, FR, vol. 50, Mar. 7, 2012, pp. 198-206, XP028421147.

Murali, Gopal, et al., "Microbiome Selection Could Spur Next-Generation Plant Breeding Strategies," Frontiers in Microbiology, vol. 7, Dec. 7, 2016, XP055531064.

United States Patent Office, Non-Final Office Action, U.S. Appl. No. 14/964,429, filed Aug. 9, 2016, 6 Pages.

United States Patent Office, Final Office Action, U.S. Appl. No. 14/964,429, filed May 31, 2017, 9 Pages.

United States Patent Office, Non-Final Office Action, U.S. Appl. No. 15/212,038, filed Sep. 21, 2016, 10 Pages.

United States Patent Office, Non-Final Office Action, U.S. Appl. No. 15/063,350, filed Nov. 10, 2016, 18 Pages.

United States Patent Office, Final Office Action, U.S. Appl. No. 14/614,193, filed Dec. 22, 2016, 13 Pages.

United States Patent Office, Final Office Action, U.S. Appl. No. 14/614,193, filed Jul. 18, 2017, 14 Pages.

United States Patent Office, Final Office Action, U.S. Appl. No. 14/614,193, filed May 3, 2018, 10 Pages.

United States Patent Office, Non-Final Office Action, U.S. Appl. No. 15/107,973, filed Apr. 10, 2017, 39 Pages.

United States Patent Office, Final Office Action, U.S. Appl. No. 15/107,973, filed Jan. 26, 2018, 20 Pages.

United States Patent Office, Final Office Action, U.S. Appl. No. 14/410,537, filed May 5, 2017, 9 Pages.

United States Patent Office, Non-Final Office Action, U.S. Appl. No. 15/034,862, filed May 19, 2017, 8 Pages.

(56) References Cited

OTHER PUBLICATIONS

United States Patent Office, Final Office Action, U.S. Appl. No. 15/034,862, filed Jan. 12, 2018, 14 Pages.
United States Patent Office, Non-Final Office Action, U.S. Appl. No. 14/916,514, filed Sep. 20, 2017, 31 Pages.
United States Patent Office, Non-Final Office Action, U.S. Appl. No. 15/143,398, filed Sep. 22, 2017, 17 Pages.
United States Patent Office, Non-Final Office Action, U.S. Appl. No. 15/143,394, filed Sep. 25, 2017, 15 Pages.
United States Patent Office, Non-Final Office Action, U.S. Appl. No. 15/107,965, filed Jun. 21, 2018, 27 Pages.
Wang, L. et al. Application of Bioorganic Fertilizer Significantly Increased Apple Yields and Shaped Bacterial Community Structure in Orchard Soil.
Whelehan, et al., "Microencapsulation using vibrating technology," Journal of Microencapsulation 2011, vol. 28(8), pp. 669-688.
Zhao, Jun, et al., "Effects of organic-inorganic compound fertilizer with reduced chemical fertilizer application on crop yields, soil biological activity and bacterial community structure in a rice-wheat cropping system," Applied Soil Ecology, vol. 99, Nov. 28, 2015, pp. 1-12, XP055530937.
PCT Invitation to Pay Additional Fees, PCT Application No. PCT/CA2013/000091, dated Mar. 27, 2013, 2 Pages.
PCT International Search Report and Written Opinion for PCT/CA2013/000091, dated Sep. 20, 2013, 17 Pages.
PCT International Search Report and Written Opinion for PCT/EP2013/062976, dated Dec. 22, 2014, 9 Pages.
PCT International Search Report, Application No. PCT/US2014/044427, dated Dec. 3, 2014, 9 Pages.
PCT International Search Report and Written Opinion, Application No. PCT/US2014/054160, dated Dec. 9, 2014, 21 Pages.
PCT Invitation to Pay Additional Fees, PCT Application No. PCT/US2014/064411, dated Feb. 5, 2015, 2 Pages.
PCT International Search Report and Written Opinion, International Application No. PCT/US2014/064411, dated Mar. 27, 2015, 15 Pages.
PCT Invitation to Pay Additional Fees, PCT Application No. PCT/US2014/072399, dated Apr. 14, 2015, 2 Pages.
PCT International Search Report and Written Opinion, International Application No. PCT/US2014/072399, dated Jun. 26, 2015, 22 Pages.
PCT Invitation to Pay Additional Fees, PCT Application No. PCT/US2014/072400, dated Apr. 16, 2015, 6 Pages.
PCT International Search Report and Written Opinion, Application No. PCT/US2014/072400, dated Jul. 8, 2015, 38 Pages.
Invitation to Pay Additional Fees, PCT Application No. PCT/US2015/038110, dated Sep. 22, 2015, 8 Pages.
NCBI GenBank: Accession No. XP55670271, "*Enterobacter* sp. MLB05 16S ribosomal RNA gene, partial sequence—Nucleotide", Jun. 9, 2012, 1 Page, can be retreived at URL:https//www.ncbi.nlm.nih gov/nuccore/J Q765415.1/.
NCBI GenBank: Accession No. XP55670274, "*Enterobacter* sp. CR 6-3 16S ribosomal RNA gene, partial sequence—Nucleotide", Mar. 27, 2013, 1 Page, can be retreived at URL:https://www.ncbi nlm. nih.gov/nuccore/K C355340.
NCBI GenBank: Accession No. XP55670279, "Uncultured bacterium clone bb2s4 16S ribosomal RNA gene, partial seque—Nucleotide", May 6, 2005, 1 Page, can be retreived at URL:https://www.ncbi.nlm.nih.gov/nuccore/D Q068880.
European Patent Office, Communication Pursuant to Article 94(3) EPC for European Patent Application No. EP 14777213.1, dated Jun. 18, 2018, 4 Pages.
De Melo Pereira, G. V., et al. "A Multiphasic Approach for the Identification of Endophytic Bacterial in Strawberry Fruit and their Potential for Plant Growth Promotion," Microb. Ecology, 2012, pp. 405-417, vol. 63, No. 2.
Result 11 from a search in the GenEmbl database, GenEmbl Record No. EU 977189, Smith et al., "Bioactive endophytes warrant intensified exploration and conservation," PLoS One 3(8):E3052, 2008.

Result 3 from a search in the GenEmbl database, GenEmbl Record No. KF011597, Paenibacillus strain No. HA13, Park et al., "Isolation and characterization of humic substances-degrading bacteria from the subarctic Alaska grasslands," J Basic Microbiol, 2013.
PCT International Search Report and Written Opinion for PCT/US2018/051467, dated Feb. 4, 2019, 22 pages.
Chaves, J., et al., "Identification and Phylogeny of Streptomyces Based on Gene Sequences", Research Journal of Microbiology, vol. 13, No. 1, Dec. 15, 2017, pp. 13-20, XP055675917.
Girard, G., et al., "A novel taxonomic marker that discriminates between morphologically complex actinomycetes", Open Biology, vol. 3, No. 10, Oct. 2013, p. 130073,XP055675916.
Guo, Y., et al. "A multi locus phylogeny of the Streptomyces griseus 16S rRNA gene clade: use of multilocus sequence analysis for streptomycete systematics", International Journal of Systematic and Evolutionary Microbiology, vol. 58, No. 1, 2008, pp. 149-159, XP055675936.
PCT Invitation to Pay Additional Fees, PCT Application No. PCT/US2017/064292, dated Mar. 6, 2018, 15 Pages.
PCT International Search Report and Written Opinion, PCT Application No. PCT/US2017/068255, Mar. 19, 2018, 14 Pages.
PCT International Search Report and Written Opinion PCT/AU2018/050387, dated Jul. 12, 2018 (Filing date is Apr. 27, 2018).
PCT International Search Report and Written Opinion for PCT/US2017/064292, dated May 11, 2018, 20 Pages.
Bentley, S.D., et al., Complete genome sequence of the model actinomycete Streptomyces coelicolor A3(2), Nature. May 9, 2002;417(6885):141-7. (Year: 2002).
Gabor, J., et al., "Mycorrhizal fungi effects on nutrient composition and yield of soybean seeds," Journal of Plant Nutrition, 20:4-5, 581-591, 1997.
Gopalakrishnan, S. et al., "Plant growth-promoting activities of *Streptomyces* spp. In sorghum and rice", SpringerPlus, 2/1/574, pp. 1-8, http://www.springerplus com/content/2/1/574, 2013.
Groppe, K., et al., "Interaction between the endophytic fungus Epichloë bromicola and the grass *Bromus erectus* effects of endophyte infection, fungal concentration and environment on grass growth and flowering," Mol Ecol., 8:1827-1835, 1999.
Hubbard, M., "Fungal Endophytes that Confer Heat and Drought Tolerance to Wheat," Doctoral dissertation, University of Saskatchewan, 2012.
Ikeda, H., et al., "Complete genome sequence and comparative analysis of the industrial microorganism Streptomyces avermitilis," Nat Biotechnol. May 2003;21 (5) :526-31. Epub Apr. 14, 2003. (Year: 2003).
Lee, J., et al., "*Streptomyces koyangensis* sp. nov., a novel actinomycete that produces 4-phenyl-3-butenoic acid," Int J Syst Evol Microbial. Jan. 2005;55(Pt 1):257-62 (Year: 2005).
Lind, A., et al., "Drivers of genetic diversity in secondary metabolic gene clusters within a fungal species", PLOS Biology, Nov. 17, 2017, 26 pages.
Pacovsky, R., "Carbohydrate, protein and amino acid status of Glycine-Glomus-Bradyrhizobium symbioses," Physiologia Pantarium; 75:346-354, 1989).
Sha, T. et al., "Genetic diversity of the endemic gourmet mushroom Thelephora ganbajun from southwestern China", Microbiology (2008), 154, 3460-3468.
Sugita, T. et al., "Intraspecies Diversity of Cryptococcus laurentii as Revealed by Sequences of Internal Transcribed Spacer Regions and 28S rRNA Gene and Taxonomic Position of C. laurentii Clinical Isolates", Journal of Clinical Microbiology, Apr. 2000, p. 1468-1471.
Wiebold, M., et al., "Agriculture Experiment Station, College of Agriculture, Food & Natural Resources, University of Missouri, Special Report 589, pp. 1-124).".
Le, X.H., et al., "Effects of endophytic Streptomyces on the lucerne (*Medicago sativa* L.) symbiosis at different levels of nitrogen," 17th Australian Nitrogen Fixation Conference 2014 Proceedings, Sep. 29, 2014, ed. Gupta, V.V.S.R., Unkovich, M. and Kaiser, B. N., ASNF, University of Adelaide, pp. 66-67.
Alvarez-Perez, S., et al., "Zooming-in on floral nectar: a first exploration of nectar-associated bacteria in wild plant communities," FEMS Microbiol. Ecol., 2012, vol. 80, No. 3, pp. 591-602.

(56) References Cited

OTHER PUBLICATIONS

European Patent Office, Supplementary European Search Report, European Patent Application No. 13874703.5, dated Jun. 21, 2016, 3 Pages.
Invitation to Pay Additional Fees, PCT Application No. PCT/US2015/038187, dated Oct. 14, 2015, 5 Pages.
Coombs, J. T., et al., "Isolation and Identification of Actinobacteria from Surface-Sterilized Wheat Roots," Applied and Environmental Microbiolog,, 2003, pp. 5603-5608, vol. 69, No. 9.
Laus, M. C., et al., "Role of Cellulose Fibrils and Exopolysaccharides of Rhizobium leguminosarum in Attachment to and Infection of Vicia sativa Root Hairs," Mol Plant Microbe Internet., 2005, pp. 533-538, vol. 16, No. 6.
United States Patent Office, Non-Final Office Action, U.S. Appl. No. 15/143,398, filed Sep. 22, 2017, 16 Pages.
PCT International Search Report and Wlitten Opinion, PCT Application No. PCT/US2015/068206, dated Jun. 27, 2016, 20 Pages.
PCT International Search Report and Wrrtten Opinion, PCT Application No. PCT/US2016/030292, dated Aug. 12, 2016, 20 Pages.
PCT International Search Report and Wrrtten Opinion, PCT Application No. PCT/US2016/030293, dated Aug. 11, 2016, 23 Pages.
PCT International Search Report and Wlitten Opinion, PCT Application No. PCT/US2016/036504, dated Nov. 4, 2016, 18 Pages.
GenEmbl Database, GenEmbl Record No. JN872548.1, 2 Pages.
Soe, K.M, et al, "Evaluation of effective Myanmar Bradyrhizobium strains isolated from Myanmar soybean and effects of coinoculation with Streptomyces griseoglavus P4 for nitrogen fixation", Soil science and plant nutrition 59.3 (2013): 361-370 (Year: 2013).
Ngom, A et al., "A novel symbiotic nitrogen-fixing member of the Ochrobactrum clade isolated from root nodues of Acacia mangium" J. Gen. Appl. Microbiol. (2004) 50: 17-27.
Trujillo, M.E et al., "Nodulation of Lupinus albus by strins of *Ochrobactrum lupini* sp. nov." Appl. Environ Microbiol Mar. 2005; 71(3): 1318-1327.
Bal, H.B et al., "Isolation of ACC deaminase producting PGPR from rice rhizosphere and evaluating their plant growth promoting activity under salt stress" Plant Soil (2013) 366: 93-105 doi: 10/1007/s11104-012-1402-5.
Chakraborty et al., "Evaluation of Ochrobactrum anthropi TRS-2 and its talcbased formulation for enhancement of growth of tea plants and management of brown root rot disease." Journal of Applied Microbiology, 2009, 107 (2):625-634 DOI:10.1111/j.1365-2672.2009.04242.x <https://doi.org/10.1111/j.1365-2672.2009.04242.x.
Gitaitis, R., et al., "The Epidemiology and Management of Seedborne Bacterial Diseases," Annu Rev Phytopathol., 2007, pp. 371-397, vol. 45.
Grondona, I., et al., "TUSAL®, a commercial biocontrol formulation based on Trichoderma," Bulletin OILB/SROP, 2004, pp. 285-288, vol. 27, No. 8.
Haake, V., et al., "Transcription Factor CBF4 is a Regulator of Drought Adaptation in *Arabidopsis*," Plant Physiol., 2002, pp. 639-648, vol. 130.
Haas, D., et al., "R Factor Variants with Enhanced Sex Factor Activity in Pseudomonas aeruginosa," Mol Gen Genet., 1976, pp. 243-251, vol. 144.
Hahm, M-S., et al., "Biological Control and Plant Growth Promoting Capacity of Rhizobacteria and Pepper Under Greenhouse and Field Conditions," The Journal of Microbiology, The Microbiological Society of Korea, Heidelberg, Jun. 30, 2012, pp. 380-385, vol. 50, No. 3.
Hallman, J., et al., "Bacterial Endophytes in Agricultural Crops," Canadian J Microbiol., 1997, pp. 895-914, vol. 43.
Hanson, L.E., "Reduction of Verticillium Wilt Symptoms in Cotton Following Seed Treatment with Trichoderma virens," The Journal of Cotton Science, 2000, pp. 224-231, vol. 4, No. 4.
Hanson, LE., "Reduction of Verticillium Wilt Symptoms in Cotton Following Seed Treatment with Trichoderma virens," Proceedings Beltwide Cotton Conferences, 2000, vol. 1. (Abstract), 1 Page.
Hardegree, S. P. et al., "Effect of Polyethylene Glycol Exclusion on the Water Potential of Solution-Saturated Filter Paper," Plant Physiol., 1990, pp. 462-466, vol. 92.
Hardoim, P. R., et al., "Assessment of Rice Root Endophytes and Their Potential for Plant Growth Promotion," In: Hardoim, P.R., Bacterial Endophytes of Rice—Their Diversity, Characteristics and Perspectives, Groningen, 2011, pp. 77-100.
Harman, G.E., et al., "Symposium: biocontrol and biotechnological methods for controlling cotton pests," Proceedings of the Beltwide Cotton Production Research Conf., 1989, Memphis, Tennessee, USA, pp. 15-20. (Abstract).
Hepler, P. K., et al., "Polarized Cell Growth in Higher Plants," Annu Rev Cell Dev Biol., 2001, pp. 159-187, vol. 17.
Hibbett, D.S., et al., "A Higher-Level Phylogenetic Classification of the Fungi," Mycol Res., 2007, pp. 509-547, vol. 111.
Hill, N. S., et al., "Endophyte Survival during Seed Storage: Endophyte-Host Interactions and Heritability," Crop Sci., 2009, pp. 1425-1430, vol. 49.
Hill N. S., et al., "Endophyte Survival during Seed Storage: Endophyte-Host Interactions and Heritability," PowerPoint, Dept. Crop Soil Sciences, University of Georgia, Nov. 16, 2012, 3 Pages.
Hinton, D. M., et al., "Enterobacter cloacae is an endophytic symbiont of corn," Mycopathologia, 1995, pp. 117-125, vol. 129.
Howell, C.R., et al., "Induction of Terpenoid Synthesis in Cotton Roots and Control of Rhizoctonia solani by Seed Treatment with Trichoderma virens," Phytopathology, 2000, pp. 248-252, vol. 90, No. 3.
Hubbard, M., et al., "Fungal Endophytes Improve Wheat Seed Germination Under Heat and Drought Stress," Botany, 2012, pp. 137-149, vol. 90.
Humann, J., et al., "Complete genome of the onion pathogen Enterobacter cloacae EcWSU1 ," Standard in Genomic Sciences, Dec. 31, 2011, vol. 5, No. 3, pp. 279-286.
Hung, P.Q., et al., "Isolation and Characterization of Endophytic Bacteria in Soybean (*Glycine* SP.)," Omonrice, 2004, pp. 92-101, vol. 12.
Idris, A., et al., "Efficacy of Rhizobacteria for Growth Promotion in Sorghum Under Greenhouse Conditions and Selected Modes of Action Studies," J Agr Sci., 2009, pp. 17-30, vol. 147.
Ikeda, S., et al., "The Genotype of The Calcium/Calmodulin-Dependent Protein Kinase Gene (CCaMK) Determines Bacterial Community Diversity in Rice Roots Under Paddy And Upland Field Conditions," Applied and Environmental Microbiology, 2011, pp. 4399-4405, vol. 77, No. 13.
Imoto, K., et al., "Comprehensive Approach to Genes Involved in Cell Wall Modifications in *Arabidopsis thaliana*," Plant Mol Biol., 2005, pp. 177-192, vol. 58.
Jalgaonwala, R., et al., "A Review on Microbiol Endophytes from Plants: A Treasure Search for Biologically Active Metabolites," Global Journal of Research on Medicinal Plants & Indigenous Medicine, 2014, pp. 263-277, vol. 3, No. 6.
Janda, J.M., et al., "16S rRNA Gene Sequencing for Bacterial Identification in the Diagnostic Laboratory: Pluses, Perils, and Pitfalls," Journal of Clinical Microbiology, 2007, pp. 2761-2764, vol. 45, No. 9.
Johnston-Monje, D., et al., "Plant and Endophyte Relationships: Nutrient Management," Comprehensive Biotechnol., 2011, pp. 713-727, vol. 4.
Jones, K.L., "Fresh Isolates of Actinomycetes in which the Presence of Sporogenous Aerial Mycelia is a Fluctuating Characteristic," J Bacteriol., 1949, pp. 141-145, vol. 57, No. 2.
Kaga, H., et al., "Rice Seeds as Sources of Endophytic Bacteria," Microbes Environ., 2009, pp. 154-162, vol. 24, No. 2.
Kalns, L., et al., "The Effects of Cotton Fungal Endophytes in the Field on Arthropod Community Structure," Power Point Presentation dated Jan. 7, 2013, 17 Pages.
Kang, B. H., et al., "Members of the *Arabidopsis* Dynamin-Like Gene Family, ADL1, are Essential for Plant Cytokinesis and Polarized Cell Growth," Plant Cell, 2003, pp. 899-913, vol. 15.
Khan, A.L., et al., "Salinity Stress Resistance Offered by Endophytic Fungal Interaction Between Penicillium minioluteum LHL09 and *Glycine max.* L," J. Microbiol. Biotechnol., 2011, pp. 893-902, vol. 21, No. 9.

(56) References Cited

OTHER PUBLICATIONS

Kruger, M., et al., "DNA-Based Species Level Detection of Glomeromycota: One PCR Primer Set for All Arbuscular Mycorrhizal Fungi," New Phytol., 2009, pp. 212-223, vol. 183.

Kuklinsky-Sobral, J., et al., "Isolation and Characterization of Endophytic Bacteria from Soybean (*Glycine max*) Grown in Soil Treated with Glyphosate Herbicide," Plant and Soil, 2005, pp. 91-99, vol. 273.

Kuklinsky-Sobral, J., et al., "Isolation and characterization of soybean-associated bacteria and their potential for plant growth promotion," Environmental Microbiology, 2004, pp. 1244-1251, vol. 6, No. 12.

Kumar, S., et al., "MEGA7: Molecular Evolutionary Genetics Analysis version 7.0 for bigger datasets," Molecular Biology and Evolution, Mar. 22, 2016, vol. 33, pp. 1870-1874.

Labeda, D.P., et al., "Phylogenetic study of the species within the family Streptomycetaceae," Antonie van Leeuwenhoek, 2012, vol. 101, pp. 73-104, Springer.

Lanver, D., et al., "Sho1 and Msb2-Related Proteins Regulate Appressorium Development in the Smut Fungus Ustilago aydis," Plant Cell, 2010, pp. 2085-2101, vol. 22.

Le, X.H., et al., "Isolation and characterisation of endophytic actinobacteria and their effect on the early growth and nodulation of lucerne (*Medicago sativa* L.)," 17th Australian Nitrogen Fixation Conference 2014 Proceedings, Sep. 29, 2014, ed. Gupta, V.V.S.R., Unkovich, M. and Kaiser, B. N., ASNF, University of Adelaide, pp. 134-136.

Lehman, S.G., "Treat Cotton Seed," Review of Applied Mycology, 1945, 24, 369, 16 Pages.

Lehman, S.G., "Treat Cotton Seed," Research and Farming III, Progr. Rept., 1945, 3, 5, 16 Pages.

Leonard, C. A., et al., "Random Mutagenesis of the Aspergillus oryzae Genome Results in Fungal Antibacterial Activity," Int J Microbiol., 2013, vol. 2013, Article ID 901697, 6 Pages.

Li, H. M., et al., "Expression of a Novel Chitinase by the Fungal Endophyte in Poa ampla," Mycologia, 2004, pp. 526-536, vol. 96, No. 3.

Li, H., et al., "Endophytes and their role in phytoremediation," Fungal Diversity, 2012, pp. 11-18, vol. 54.

Liu, M., et al., "A Novel Screening Method for Isolating Exopolysaccharide-Deficient Mutants," Appl Environ Microbiol., 1998, pp. 4600-4602, vol. 64, No. 11.

Liu, Y., et al., "Investigation on Diversity and Population Succession Dynamics of Endophytic Bacteria from Seeds of Maize (*Zea mays* L., Nongda108) at Different Growth Stages," Ann Microbiol., 2013, pp. 71-79, vol. 63.

Liu, D., et al., "Osmotin Overexpression in Potato Delays Development of Disease Symptoms," Proc Natl Acad Sci USA, 1994, pp. 1888-1892, vol. 91.

Liu, Y., et al., "Study on Diversity of Endophytic Bacterial Communities in Seeds of Hybrid Maize and their Parental Lines," Arch Microbiol., 2012, pp. 1001-1012, vol. 194.

Long, H. H., et al., "The Structure of the Culturable Root Bacterial Endophyte Community of Nicotiana attenuata is Organized by Soil Composition and Host Plant Ethylene Production and Perception," New Phytol., 2010, pp. 554-567, vol. 185.

Lopez-Lopez, A., et al., "Phaseolus vulgaris Seed-Borne Endophytic Community with Novel Bacterial Species such as *Rhizobium endophyticum* sp. nov.," Systematic Appl Microbiol., 2010, pp. 322-327, vol. 33.

Lorck, H., "Production of Hydrocyanic Acid by Bacteria," Physiol Plant, 1948, pp. 142-146, vol. 1.

Riken, GI No. GMFL01-01-D03, 2 Pages, [online] [Retrieved on Dec. 18, 2017] Retrieved from the internet <URL:http://spectra.psc.riken.jp/menta.cgi/rsoy/datail?id=GMFL01-01-D03>.

Rodriguez, H., et al., "Expression of a Mineral Phosphate Solubilizing Gene From Erwinia herbicola in Two Rhizobacterial Strains," J Biotechnol., 2001, pp. 155-161, vol. 84.

Rodriguez, R.J., et al., "Stress Tolerance in Plants via Habitat-Adapted Symbiosis," ISME J., 2008, pp. 404-416, vol. 2.

Rodriguez-Navarro, D., et al., "Soybean Interactions with Soil Microbes, Agronomical and Molecular Aspects," Agronomy for Sustainable Development, 2011, pp. 173-190, vol. 31, No. 1.

Roessner, U., et al., "Metabolic Profiling Allows Comprehensive Phenotyping of Genetically or Environmentally Modified Plant Systems," Plant Cell, 2001, pp. 11-29, vol. 13.

Rosado, A. S., et al., "Phenotypic and Genetic Diversity of Paenibacillus azotofixans Strains Isolated from the Rhizoplane or Rhizosphere Soil of Different Grasses," J App Microbiol., 1998, pp. 216-226, vol. 84.

Rosenblueth, A., et al., "Seed Bacterial Endophytes: Common Genera, Seed-to-Seed Variability and Their Possible Role in Plants," Acta Hort., 2012, pp. 39-48, vol. 938.

Rosenblueth, M., et al., "Bacterial Endophytes and Their Interactions With Host," Molecular Plant-Microbe Interactions, 2006, pp. 827-837, vol. 19, No. 8.

Ross, P.L., et al., "Multiplexed Protein Quantitation in *Saccharomyces cerevisiae* Using Amine-Reactive Isobaric Tagging Reagents," Mol Cell Proteomics, 2004, pp. 1154-1169, vol. 3, No. 12.

Saleem, M., et al., "Perspective of Plant Growth Promoting Rhizobacteria (PGPR) Containing ACC Deaminase in Stress Agriculture," J Ind Microbiol Biotechnol., Oct. 2007, pp. 635-648, vol. 34.

Samac, D.A., et al., "Recent Advances in Legume-Microbe Interactions: Recognition, Defense Response, and Symbiosis from a Genomic Perspective," Plant Physiol., 2007, pp. 582-587, vol. 144.

Sardi, P., et al., "Isolation of Endophytic Streptomyces Strains from Surface Sterilized Roots," Applied and Environmental Microbiology, 1992, pp. 2691-2693, vol. 58, No. 8.

Sarwar, M., et al., "Tryptophan Dependent Biosynthesis of Auxins in Soil," Plant Soil, 1992, pp. 207-215, vol. 147.

Schmieder, R., et al., "Quality Control and Preprocessing of Metagenomic Datasets," Bioinformatics, 2011, pp. 863-864, vol. 27, No. 6.

Schoch, C. L., et al., "Nuclear Ribosomal Internal Transcribed Spacer (ITS) Region as a Universal DNA Barcode Marker for Fungi," Proc Natl Acad Sci USA, 2012, pp. 6241-6246, vol. 109, No. 16.

Schwyn, B. et al., "Universal Chemical Assay for the Detection and Determination of Siderophores," Analytical Biochemistry, 1987, pp. 47-56, vol. 160.

Senthilkumar, M., et al., "Biocontrol Potential of Soybean Bacterial Endophytes Against Charcoal Rot Fungus, Rhizoctonia batatiola," Current Microbiology, 2009, vol. 58, pp. 288-293.

Sessitsch, A., et al., "*Burkholderia phytofirmans* sp. Nov., a novel plant-associated bacterium with plant-beneficial properties," International Journal of Systematic and Evoluntary Microbiology, 2005, pp. 1187-1192, vol. 55.

Shapiro-Ilan, D.I., et al., "The Potential for Enhanced Fungicide Resistance in Beauveria Bassiana Through Strain Discovery and Artificial Selection," Journal of Invertebrate Pathology, 2002, pp. 86-93, vol. 81.

Shankar, M., et al.,"Root colonization of a rice growth promoting strain of Enterobacter cloacae," Journal of Basic Microbiology, 2011, pp. 523-530, vol. 51.

Singh, A K., et al., "Uncultured *Actinomyces* sp. Clone EMLACT 80 IV (New) 16S Ribosomal RNA Gene, Partial Sequence," NCBI GenBank Accession No. JQ285908. Submitted Dec. 13, 2011, 1 page.

Soares, M. M. C. N., et al., "Screening of Bacterial Strains for Pectinolytic Activity: Characterization of the Polygalacturonase Produced by *Bacillus* SP," Revista de Microbiolgia, 1999, pp. 299-303, vol. 30.

Soe, K.M., et al., "Effects of endophytic actinomycetes and Bradyrhizobium japonicum strains on growth, nodulation, nitrogen fixation and seed weight of different soybean varieties," Soil Science and Plant Nutrition, 2012, pp. 319-325, vol. 58, No. 3.

Soe, K.M., et al., "Low-Density Co-Inoculation of Myanmar Bradyrhizobium yuanmingense MAS34 and Streptomyces griseoflavus P4 to Enhance Symbiosis and Seed Yield in Soybean Varieties," American Journal of Plant Sciences, 2013, pp. 1879-1892, vol. 4.

(56) References Cited

OTHER PUBLICATIONS

Sogonov, M.V., et al.,"The hyphomycete *Teberdinia hygrophila* gen. nov., sp. nov. and related anamorphs of *Pseudeurotium* species," Mycologia, May 2005, pp. 695-709, vol. 97, No. 3.

Song, M., et al., "Effects of Neotyphodium Endophyte on Genmination of Hordeum brevisubulatum under Temperature and Water Stress Conditions," Acta Agrestia Sinica, 2010, pp. 834-837, vol. 18, No. 6. (English Abstract).

Souleimanov, A., et al., "The Major Nod Factor of Bradyrhizobium japonicum Promotes Early Growth of Soybean and Corn," J. Exp. Bot., 2002, pp. 1929-1934, vol. 53, No. 376.

Spiekermann, P., et al., "A Sensitive, Viable-Colony Staining Method Using Nile Red for Direct Screening of Bacteria that Accumulate Polyhydroxyalkanoic Acids and Other Lipid Storage Compounds," Arch Microbiol., 1999, pp. 73-80, vol. 171.

Staudt, A. K., et al., "Variations in Exopolysaccharide Production by Rhizobium tropici," Arch Microbiol., 2012, pp. 197-206, vol. 194.

Strobel, G. A., "Endophytes as Sources of Bioactive Products," Microbes and Infection, 2003, pp. 535-544, vol. 5.

Sturz, A. V., et al., "Weeds as a Source of Plant Growth Promoting Rhizobacteria in Agricultural Soils," Can J Microbiol., 2001, pp. 1013-1024, vol. 47, No. 11.

Surertte, M.A., et al. "Bacterial Endophytes in Processing Carrots (*Daucus carota* L. var. sativus): Their Localization, Population Density, Biodiversity and Their Effects on Plant Growth," Plant and Soil, 2003, pp. 381-390, vol. 253, No. 2.

Suto, M., et al., "Endophytes as Producers of Xylanase," J Biosci Bioeng., 2002, pp. 88-90, vol. 93, No. 1.

Sword, G., "Manipulating Fungal Endophytes to Protect Plants from Insects and Nematodes," Power Point Presentation dated Aug. 7, 2013, 48 Pages.

Sword, G., et al., "Manipulating Fungal Endophytes for the Protection of Cotton in the Field," Power Point Presentation dated Jan. 7, 2013.

Sword, G., et al., "Field Trials of Potentially Beneficial Fungal Endophytes in Cotton," Power Point Presentation dated Jan. 7, 2013, 17 Pages.

Sword, G., "Fungal Endophytes to Protect Cotton from Insects and Nematodes," Power Point Presentation dated Dec. 7, 2012, 20 Pages.

Sword, G., "Natural Enemies—The Forgotten Basis of IPM?," Power Point Presentation dated Sep. 6, 2013, 33 Pages.

Taghavi, S., et al., "Genome Survey and Characterization of Endophytic Bacteria Exhibiting a Beneficial Effect on Growth and Development of Poplar Trees," Applied and Environmental Microbiology, 2009, pp. 748-757, vol. 75, No. 3.

Taghavi, S., et al., "Genome Sequence of the Plant Growth promoting Endophytic Bacterium *Enterobacter* sp. 638", PLoS Genet., May 2010, vol. 6, Issue 5, e1000943, pp. 1-15.

Tamura, K., et al., "Estimation of the number of nucleotide substitutions in the control region of mitochondrial DNA in humans and chimpanzees," Molecular Biology and Evolution, 1993, vol. 10, No. 3, pp. 512-526.

Taylor, A.G., et al., "Concepts and Technologies of Selected Seed Treatments," Annu. Rev. Phytopathol., 1990, pp. 321-339, vol. 28.

Teather, R. M., et al., "Use of Congo Red-Polysaccharide Interactions in Enumeration and Characterization of Cellulolytic Bacteria from the Bovine Rumen," Appl Environ Microbiol., 1982, pp. 777-780, vol. 43, No. 4.

Thakur, A., et al., "Detrimental effects of endophytic fungus *Nigrospora* sp. on survival and development of Spodoptera litura," Biocontrol Science and Technology, Feb. 1, 2012, pp. 151-161, vol. 22, No. 2.

Thakur, A., et al., "Enhanced Resistance to Spodoptera litura in Endophyte Infected Cauliflower Plants," Environmental Entomology, Apr. 1, 2013, pp. 240-246, vol. 42, No. 2.

Thakur, A., et al., "Suppression of Cellular Immune Response in Spodoptera litura (Lepidoptera: Noctuidae) Larvae by Endophytic Fungi Nigrospora oryzae and Cladosporium uredinicola,", Annals of the Entomological Society of America, May 1, 2014, pp. 674-679, vol. 107, No. 3.

Theis, K. R., et al., "Uncultured Bacterium Clone GM2GI8201A64RC 16S Ribosomal RNA Gene, Partial Sequence," NCBI GenBank Accession No. JX051943, Submitted May 14, 2012, 1 Page.

Thomas, L., et al., "Development of Resistance to Chlorhexidine Diacetate in Pseudomonas aeruginosa and the Effect of a "Residual" Concentration," J Hosp Infect., 2000, pp. 297-303, vol. 46.

Thomashow, M. F., "So What's New in the Field of Plant Cold Acclimation? Lots!," Plant Physiol., 2001, pp. 89-93, vol. 125.

Tokala, R. T., et al., "Novel Plant-Microbe Rhizosphere Interaction Involving Streptomyces Lydicus WYEC108 and the Pea Plant (*Pisum sativum*)," Applied and Environmental Microbiology, May 2002, pp. 2161-2171, vol. 68, No. 5.

Compant, S., et al., "Endophytic colonization of *Vitis vinfera* L. by Burkholderia phytofirmans strain PsJN: from the rhizosphere to inflorescence tissues," FEMS Microbiol Ecol, 2008, pp. 84-93, vol. 63.

NCBI GenBank: CP000653.1 "*Enterobacter* sp. 638, complete genome" Jan. 28, 2014, 5 Pages, Can be retrieved at<URL:https://www.ncbi.nlm.nih.gov/nuccore/CP000653.1>.

NCBI GenBank: EU340965.1 "*Enterobacter* sp. 638 16S ribosomal RNA gene, partial sequence" Jan. 30, 2009, 1 Page, Can be retrieved at <URL:https://www.ncbi.nlm nih.gov/nuccore/EU340965.1>.

NCBI GenBank: EBI accession No. EM STD:GU055658, "Uncultured Periconia clone NG R 806 18S ribosomal RNA gene, partial sequence; internal transcribed spacer 1, 5.8S ribosomal RNA gene, and internal transcribed spacer 2, complete sequence; and 28S ribosomal RNA gene, partial sequence," Oct. 27, 2009, 2 Pages.

Database EMBL [Online] Oct. 1, 2001, 2 Pages, "Setosphaeria monoceras 28S ribosomal RNA gene, partial sequence," XP002777918, retrieved from EBI accession No. EM_STD:AY016368 Database accession; No. AY016368 sequence.

Hamayun, M., et al., "Cladosporium sphaerospermum as a new plant growth-promoting endophyte from the roots of *Glycine max* (L.) Merr," World Journal of Microbiology and Biotechnology, Kluwer Academic Publishers, DO, vol. 25, No. 4, Feb. 15, 2009 (Feb. 15, 2009), pp. 627-632.

Hoffman, M., et al., "Diverse Bacteria Inhabit Living Hyphae of Phylogenetically Diverse Fungal Endophytes," Applied and Environmental Microbiology, Jun. 2010, p. 4063-4075, vol. 76, No. 12.

Hoffman, M., et al., "Endohyphal Bacterium Enhances Production of Indole-3-Acetic Acid by a Foliar Fungal Endophyte," PLOS One, Sep. 24, 2013, pp. 1-8, vol. 8, Issue 9, e73132.

Hubbard, M., et al., 2011. "Agricultural Potential of Fungal Endophytes of Grasses, Cereals and Wheat," In: Wheat Genetics, Crops and Food Production. Nova Science Publishers Hauppauge, pp. 333-345.

Impullitti, A.E., et al., "Fungal endophyte diversity in soybean", Journal of Applied Microbiolog, vol. 114, No. 5, May 1, 2013, pp. 1500-1506.

Jung, C., et al., "The Effects of Endohyphal Bacteria on Anti-Cancer and Anti-Malaria Metabolites of Endophytic Fungi," Honors Thesis, University of Arizona, May 2012, 15 Pages.

Kim, M., et al., "Towards a taxonomic coherence between average nucleotide identity and 16S rRNA gene sequence similarity for species demarcation of prokaryotes", Int J Systematic Evolutionary Microbiol., 2014, vol. 64, pp. 346-351.

Klaubauf, S., et al., "Molecular diversity of fungal conmunities in agricultural soils from Lower Austria," Fungal Diversity, Aug. 13, 2010, pp. 65-75, vol. 44, No. 1.

Knapp, D., et al., "Inter- and intraspecific functional diversity of fungal root endophytes of semiarid sandy grasslands," Acta Microbiologica et Immunologica Hungarica, Nov. 2017, vol. 64, Issue Supplement 1, pp. 1-101.

Kumar, A., et al., "Bio-control potential of *Cladosporium* sp. (MCPL-461), against a noxious weed *Parthenium hsterophorus* L.," J Environ Biol., Mar. 2009, pp. 307-312, vol. 30, Issue 2.

Kusari, S., et al. "Chemical ecology of endophytic fungi: origins of secondary metabolites," Cell Press, Chem & Biol, vol. 19, pp. 792-798, 2012.

Liu, Y., et al., "Phylogenetic relationships among ascomycetes: evidence from an RNA polymerase II subunit," Mol. Biol. Evol. 1999. vol. 16, No. 12, pp. 1799-1808.

(56) References Cited

OTHER PUBLICATIONS

Mandyam, K., et al., "Mutualism-parasitism paradigm synthesized from results of root-endophyte models", Frontiers in Microbiology, vol. 5, Jan. 12, 2015, pp. 1-14.
Miyoshi-Akiyama, T., et al., "Multilocus Sequence Typing (MLST) for Characterization of Enterobacter cloacae," PLoS ONE, 2013, vol. 8, No. 6, 10 Pages, e66358.
Nassar, A., et al., "Promotion of plant growth by an auxin-producing isolate of the yeast *Williopsis satumus* endophytic in maize (*Zea mays* L.) roots", Biology and Fertility of Soils; Cooperating Journal of International Society of Soil Science, Springer, Berlin, DE, vol. 42, No. 2, Nov. 1, 2005, pp. 97-108.
O'Hanlon, K., et al., "Exploring the potential of symbiotic fungal endophytes in cereal disease suppression", Biological Control, vol. 63, No. 2, Sep. 2012, pp. 69-78.
Rae, R., et al., "A subset of naturally isolated Bacillus strains show extreme virulence to the free-living nematodes Caenorhabditis elegans and Pristionchus pacificus", Environmental Microbiology, vol. 12, No. 11, 2010, pp. 3007-3021.
Riess, K., et al., "High genetic diversity at the regional scale and possible speciation in Sebacina epigaea and S. incrustans," BMC Evolutionary Biology, 2013, vol. 13, No. 102, 17 Pages.
Samways, M.J., et al., "Assessment of the Fungus Cladosporium Oxyspoum (BERK. And CURT.) As a Potential BioControl Agent Against Certain Homoptera," Elsevier Science Publishers B.V., Jan. 1, 1986, pp. 231-239.
Sarkar, S., et al., "New report of additional enterobacterial species causing wilt in West Bengal, India," Canadian Journal of Microbiology, 2015, vol. 61, No. 7, pp. 477-486.
Saunders, M., et al., "Host-Synthesized Secondary Compounds Influence the In Vitro Interactions between Fungal Endophytes of Maize", Applied and Environmental Microbiology, Nov. 9, 2007, pp. 136-142, vol. 74, No. 1.
Schneider, C., et al., "Endophytes for plant protection: the state of the art Proceedings," DPG Spectrum Phytomedizin, Proceedings of the 5th International Symposium on Plant Protection and Plant Health in Europe, May 26-29, 2013, 347 Pages.
Shiraishi, A., et al., "Nodulation in black locust by the ammaproteobacteria *Pseudomonas* sp. and the Betaproteobacteria *Burkholderia* sp", Systematic and Applied Microbiology, vol. 33, No. 5, Aug. 2010, pp. 269-274.
Simola, L., et al., "The Effect of Some Protein and Non-Protein Amino Acids on the Growth of Cladosporium herbarum and Trichotheeium roseum," Effect of Amino Acids on Fungi, Physiologia Plantarum, 1979, vol. 46, pp. 381-387.
Stielow, J.B., et al., "One fungus, which genes? Development and assessment of universal primers for potential secondary fungal DNA barcodes," Persoonia: Molecular Phylogeny and Evolution of Fungi, 2015, vol. 35, pp. 242-263.
U'Ren, J.M., et al., "Host and geographic structure of endophytic and endolichenic fungi at the continental scale," American Journal of Botany, May 1, 2012, pp. 898-914, vol. 99, No. 5.
Valencia, E., et al., "Mini-review: Brazilian fungi diversity for biomass degradation," Fungal Genetics and Biology, 2013, pp. 9-18, vol. 60.
Vujanovic, V., et al., "Viability Testing of Orchid Seed and the Promotion of Colouration and Germination," Annals of Botany, Mar. 17, 2000, pp. 79-86, vol. 86.
Vujanovic, V., et al., "Endophytic hyphal compartmentalization is required for successful mycobiont-wheat interaction as revealed by confocal laser microscopy," The proceedings of the Soils and Crops conference in Saskatoon (2008) published 2009, 7 Pages.
Vujanovic, V., et al.,"Orchid seed viability testing by fungal bioassays and molecular phylogeny," Floriculture, ornamental and plant biotechnology, 2006, vol. 63, pp. 563-569.
Vujanovic, V., et al., "Mycovitality—a new concept of plant biotechnology," Canadian Journal Plant Pathol. 2007, vol. 29, p. 451.
Vujanovic, V., et al., "19th International Conference on *Arabidopsis*. Research Proceedings—ICAR13," Jul. 23-27, 2008, 264 Pages, Montreal, QC, Canada.
Vujanovic, V., et al., "Mycovitality and mycoheterotrophy: where lies dormancy in terrestrial orchid and plants with minute seeds?" Symbiosis, 2007, vol. 44, pp. 93-99.
Vujanovic, V., et al., "Seed endosymbiosis: a vital relationship in providing prenatal care to plants," Can. J. Plant Sci, NRC Research Press, Feb. 6, 2017, pp. 972-981, vol. 97.
Vujanovic, V., et al: "Fungal communities associated with durum wheat production system: A characterization by growth stage, plant organ and preceding crop", Crop Protection, Elsevier Science, GB, vol. 37, Feb. 19, 2012, pp. 26-34.
Yennamalli, R., et al., "Endoglucanases: insights into thermostability for biofuel applications", Biotech Biofuels, 2013, vol. 6, Issue 136, pp. 1-9.
Youssef, Y.A., et al., "Production of Plant Growth Substances by Rhizosphere Myoflora of Broad Bean and Cotton," Biologia Plantarum, 1975, pp. 175-181, vol. 17, No. 3.
Zhang, Y., et al., "BcGsl, a glycoprotein from Botrytis cinerea, elicits defence response and improves disease resistance in host plants. Biochemical and biophysical research communications," Biochemical and Biophysical Research Communications, 2015, vol. 457, No. 4, pp. 627-634.
Zhang, W., et al., Host range of Exserohilum monoceras, a potential bioherbicide for the control of *Echinochloa* species, Canadian Journal of Botany/ Journal Canadien De Botan, National Research Council, Ottawa, CA, vol. 75, Jan. 1, 1997, pp. 685-692.
Zhu et al., "*Helminthosporium velutinum* and *H. aquaticum* sp. nov. from aquatic habitats in Yunnan Province, China." Phytotaxa, 2016, vol. 253, No. 3, pp. 179-190.
Amatuzzi, R.F., et al., "Potential of endophytic fungi as biocontrol agents of Duponchelia fovealis (Zeller) (Lepidoptera:Crambidae," Brazilian Journal of Biology, Nov. 9, 2017, 7 Pages.
Artursson, V., et al., "Interactions between arbuscular mycorrhizal fungi and bacteria and their potential for stimulating plant growth", Environmental Microbiology, vol. 8, No. 1, Jan. 1, 2006, pp. 1-10.
Bing, LA, et al., "Suppression of Ostrinia nubilalis (Hübner) (Lepidoptera: Pyralidae) by endophytic Beauveria bassiana (Balsamo) Vuillemin", Environmental Entomol, Entomological Society of America, College Park, MD, US, vol. 20, Jan. 1, 1991, pp. 1207-1211.
NCBI GenBank: Accession No. JX880250.1, "Enterobacteriaceae bacterium Clero1 16S ribosomal RNA gene, partial sequence," NIH, Jun. 24, 2015, 2 Pages, can be retrieved at <URL:https://www.ncbi.nlm.nih.gov/nucleotideIJX880250.1?report=genbank&logs=nuclalign&blast_rank=80 &RID=KWUPBV08015>.
PCT International Search Report and Written Opinion, PCT Application No. PCT/US2015/038110, dated Dec. 11, 2015, 36 Pages.
Sulistiyani, et al., "Population and Diversity of Endophytic Bacteria Associated with Medicinal Plan Curumma zedoaria ", Microbiology Indonesia 8.2 (2014):4.
Bevivino, A., et al., "Characerization of free-living maize rhizosphere populatin of Burkholderia cepacia: effect of seed treatment on disease suppresssion and growth promotion of maize", FEMS Microbiology Ecology 27 (1998) 225-237.
Ciccillo, F., et al., Effects of two different application methods of Burkholderia ambifaria MCI 7 on plant growth and rhizospheric bacterial diversity.
Estrada, P., et al., "A N2-fixing endophytic *Burkholderia* sp. associated with maize plants culitvated in Mexico", Canadian Journal of Microbiology (2002), vol. 48(4), pp. 528-536.
Sharma, V.K., et al., "Enhancement of verticillium wilt resistance in tomato transplants by in vitro co-culture of seedlings with a plant growth promoting rhizobacterium (*Pseudomonas* sp. strain PsJN)", Canadian Journal of Microbiology (1998), vol. 44(6), pp. 285-294.
Grady, E., et al., "Current knowledge and perspectives of Paenibacillus: a review" Microb Cell Fact (2016) 15:203.
Li, J., et al., "Antitumour and antimicrobial activities of endophytic stretomycetes from pharmaceutical plants in rainforest", Lett Appl Microbiol. Dec. 2008; 47(6): 574-80. (Year: 2008).
Hamayun, M., et al., "Gibberellin production and plant growth promotion from pure cultures of *Cladosporium* sp. MH-6 isolated from cucumber (*Cucumis sativus* L.)", Mycologia, 102 (5), 2010, pp. 989-995.

(56) References Cited

OTHER PUBLICATIONS

Shupeng, T., et al. "Advances in Study of Interactions between Mycorrhizal Fungi and Bacteria", Journal of Qingdao Agricultural University (Natural Science Edition), vol. 30, Issue 4, pp. 240-246, Dec. 31, 2013.
Kim, S., et al., "Physiological and proteomic analyses of Korean F1 maize (Zea mays L.) hybrids under water-deficit stress during flowering", Appl. Biol. Chem. (2019) 62:32.
Halligan, B., et al., "Cloning of the murine cDNA encoding VDJP, a protein homologous to the large subunit of replication factor C and bacterial DNA ligases", GENE (1995) 217-222.
Arend, J., et al., "Hydroquinone: O-glucosytransferase from cultivated Rauvolfia cells: enrichment and partial amino acid sequences", Phytochemistry (2000) 53:187-193.
Enchev, R., et al., "Protein neddylation: beyond cullin-RING ligases", (Nature Reviews: Molecular Cell Biology (2015) 16:30-44.
Bais, H., et al., "The Role of Root Exudates in Rhizosphere Interactions with Plants and Other Organisms", Annual Review. Plant Biol. (2006) 57:233-266.
Goepfert, S., et al., "Molecular Identification and Characterization of the Arabidopsis D3,5, D2,4- Dienoyl-Coenzyme A Isomerase, a Peroxisomal Enzyme Participating in the b-Oxidation Cycle of Unsaturated Fatty Acids1", Plant Physiology (2005) 138:1947-1956.
Thomas, P., et al: "Endophytic Bacteria Associated with Growing Shoot Tips of Banana (Musa sp.) cv. Grand Naine and the Affinity of Endophytes to the Host", Microbial Ecology, Springer-Verlag, NE, vol. 58, No. 4, Jul. 25, 2009 (Jul. 25, 2009), pp. 952-964, XP019757395, ISSN: 1432-184X, DOI: 10.1007/S00248-009-9559-Z.
DATABASE Geneseq [Online] Sep. 30, 2010 (Sep. 30, 2010), "Cellulomonas fermentans 16s rRNA gene SEQ ID:39.", retrieved from EBI accession No. GSN:AWL84299 Database accession No. AWL84299; & JP 2009 072168 A (Univ of Occupational & Environ) Apr. 9, 2009 (Apr. 9, 2009).
European Patent Office, Partial European Search Report, European Patent Application No. 20171870.7, Nov. 20, 2020, 18 Pages.
European Patent Office, European Search Report, European Patent Application No. 20171870.7, dated Mar. 1, 2021, 15 Pages.
GenBank Accession NR_041978, dated Aug. 8, 2011. (Year: 2011).
GenBank Accession AF394537, dated Jul. 2, 2002. (Year: 2002).
Andreolli, M., et al., "Endophytic Burkholderia fungorum DBT1 can improve phytoremediation efficiency of polycyclic aromatic hyrocarbons", Chemosphere, Pergamon Press, Oxford, GB, vol. 92, No. 6, May 21, 2013, pp. 688-694.
Extended European Search Report for EP 20202875.9, 16 pages.
Douglas, G., et al., "PICRUSt2 for prediction of metagenome functions", Nature Biotechnology, vol. 38, No. 6, Jun. 1, 2020, pp. 685-688.
Kemp, N., et al., "Sarocladium zeae is a systemic endophyte of wheat and an effective biocontrol agent against Fusarium head blight", Biological Control, vol. 149, Publication No. 104329, 10 pages (2020).
Wicklow, D., et al., "A protective endophyte of maize: Acremonium zeae antibiotics inhibitory to Aspergillus flavus and Fasanum verticillioides", Mycol. Res. 109 (5):610-618 (May 2005).
Pan, J., et al., "Effects of host plant environment and Ustilago maydis infection on the fungal endophyte community of maize (Zea mays)", New Phytologist, vol. 178, pp. 147-156 (2008).
Wicklow, D., et al., "Occurrence of pyrrocidine and dihydroresorcylide production among Acremonium zeae populations from maize grown in different regions", Canadian Journal of Plant Pathology, vol. 30, pp. 425-433 (2008).
European Patent Office, Partial European Search Report, European Patent Application No. 18791606.9, dated Jul. 26, 2021, 16 Pages.
Abaid-Ullah, M., et al., "Plant Growth Promoting Rhizobacteria: An Alternate Way to Improve Yield and Quality of Wheat (Triticum aestivum)", International Journal of Agriculture and Biology, vol. 17, No. 1, Jan. 1, 2015, pp. 51-60.
Colla, G., et al., "Coating seeds with endophytic fungi enhances growth, nutrient uptake, yield and grain quality of winter wheat", International Journal of Plant Production, vol. 9, No. 2, Apr. 1, 2015, pp. 171-190.
Larran, S., et al., "Endophytes from wheat as biocontrol agents against tan spot disease", Biological Control, vol. 92, Sep. 11, 2015, pp. 17-23.
European Patent Office, Search Report, European Patent Application No. 17825317.5, Oct. 12, 2021, 9 Pages.
Yuan, J., et al., "Roots from distinct plant developmental stages are capable of rapidly selecting their own microbiome without the influence of environmental and soil edaphic factors", Soil Biology and Biochemistry 89 (2015): 206-209.
Bing, L., et al., Suppression of Ostrinia nubilalis (Hübner) (Lepidoptera: Pyralidae) by Endophytic Beauveria bassiana (Balsamo) Vuillemin, Environ. Entomol. 20(4): 1207-1211 (1991).
Frichot, E., et al., "Testing for Associations between loci and environmental gradients using latent factor mixed models", Mol. Biol. Evol. 30:7 1687-1699 (Year: 2013).
Bicego, M., et al., "Investigating Topic Models' Capabilities in Expression Microarray Data Classification", IEEE/transactions on computational biology and bioinformatics, 9:8 1831-1836 (Year: 2012).
Gerber, G., et al., "Inferring Dynamic Signatures of Microbes in Complex Host Ecosystems", PLOS Computational Biology 8:8 e1002624, 14 pages (Year: 2012).
Holmes, I., et al., "Dirichlet Multinomial Mixtures: Generative Models for Microbial Metagenomics", PLoSONE 7:2, e30126, 15 pages (Year: 2012).
Kim, Y., et al., "Deciphering the human microbiome using next-generation sequencing data and bioinformatics approaches", Methods 79-80, p. 52-59 (Year: 2015).
Anesi, A., et al., "Towards a scientific interpretation of the terrior concept: platicisity of the grape berry metabolome", BMP plant biology 15:191, 17 pages (Year: 2015).
Hill, S.T., The pursuit of hoppiness: propelling hop into the genomic era. Thesis, Oregon State University, 80 pages) (Year: 2016).
Li, M., et al., "Persistent homology and the branching topologies of plants", American Journal of Botany, 104:3, 349-353 (Year: 2017).
Trichoderma definition, 2016, 6 Pages, [online] [Retrieved on Sep. 16, 2016,] Retrieved from the Internet <URL: https://en.wikipedia.org/wiki/Trichoderma>.
Trotel-Aziz, P., et al., "Characterization of New Bacterial Biocontrol Agents Acinetobacter, Bacillus, Pantoea and Pseudomonas spp. Mediating Grapevine Resistance Against Botrytis cinerea," Environmental and Experimental Botany, 2008, pp. 21-32, vol. 64.
Truyens, S., et al., "Changes in the Population of Seed Bacteria of Transgenerationally Cd-Exposed Arabidopsis thaliana," Plant Biol., 2013, pp. 971-981, vol. 15.
Usadel, B., et al., "The Plant Transcriptome—From Integrating Observations to Models," Front Plant Sci., 2013, pp. 1-3, vol. 4., Article 48, 3 Pages.
Vacheron, J., et al., "Plant Growth-Promoting Rhizobacteria and Root System Functioning," Frontiers Plant Sci., 2013, vol. 4, Article 356, 19 Pages.
Valencia, C. U., et al., "Endophytic Establishment as an Unintended Consequence of Biocontrol with Fungal Entomopathogens," Power Point Presentation dated Jan. 7, 2013, 10 Pages.
Van Der Lelie, D., et al., "Poplar and its Bacterial Endophytes: Coexistence and Harmony," Critical Rev Plant Sci., 2009, pp. 346-358, vol. 28.
Verkley, G., et al., "Paraconiothyrium, a new genus to accommodate the mycoparasite Coniothyrium minitans, anamorphs of Paraphaeosphaeria, and four new species," Studies in Mycology, 2004,; pp. 323-335, vol. 50.
Vining, K., et al., "Methylome Reorganization During in vitro Dedifferentiation and Regeneration of Populus trichocarpa," BMC Plant Biol., 2013, vol. 13, No. 92, 15 Pages.
Viruel, E., et al., "Pseudomonas thiveralensis Strain IEHa 16S Ribosomal RNA Gene, Partial Sequence," NCBI GenBankAccession No. GQ169380.1, Submitted May 15, 2009, 1 Page.
Visagie, C.M., et al., "Identification and nomenclature of the genus Penicillium," Studies in Mycology, Jun. 2014, pp. 343-371, vol. 78.

(56) References Cited

OTHER PUBLICATIONS

Waller, F., et al., "The Endophytic Fungus Piriformospora indica Reprograms Barley to Salt-Stress Tolerance, Disease Resistance, and Higher Yield," PNAS, 2005, pp. 13386-13391, vol. 102, No. 38.
Wang, B., et al., "Fungal endophytes of native *Gossypium* species in Australia," Mycological Research, 2007, pp. 347-354, vol. 111, No. 3.
Wang, K., et al., "Monitoring in Planta Bacterial Infection at Both Cellular and Whole-Plant Levels Using the Green Fluorescent Protein Variant GFPuv," New Phytol., 2007, pp. 212-223, vol. 174.
Wang, Q., et al., "Naive Bayesian Classifier for Rapid Assignment of rRNA Sequences into the New Bacterial Taxonomy," Appl. Environ. Microbiol., 2007, pp. 5261-5267, vol. 73, No. 16.
Waqas, M., et al., "Endophytic Fungi Produce Gibberellins and Indoleacetic Acid and Promotes Host-Plant Growth during Stress," Molecules, 2012, pp. 10754-10773, vol. 17.
Weindling, R., "Relation of dosage to control of cotton seedling diseases by seed treatment," Plant Disease Reporter, 1943, 27, pp. 68-70.
White, J. F., et al., "A Proposed Mechanism for Nitrogen Acquisition by Grass Seedlings Through Oxidation of Symbiotic Bacteria," Symbiosis, 2012, pp. 161-171, vol. 57.
Wiegand, I., et al., "Agar and Broth Dilution Methods to Determine the Minimal Inhibitory Concentration (MIC) of AntiMicrobiol Substances," Nature Protocols, 2008, pp. 163-175, vol. 3, No. 2.
Xu, M., et al., "Bacterial Community Compositions of Tomato (*Lycopersicum esculentum* Mill.) Seeds and Plant Growth Promoting Activity of ACC Deaminase Producing Bacillus subtilis (HYT-12-1) on Tomato Seedlings" Worid J Microbiol Biotechnol., 2014, pp. 835-845, vol. 30.
Xu, Y., et al., "Biosynthesis of the Cyclooligomer Despipeptide bassianolide, an Insecticidal Virulence Factor of Beauveria bassiana," Fungal Genetics and Biology, 2009, pp. 353-364, vol. 46.
Yandigeri, M. S., et al., "Drought-tolerant endophytic actinobacteria promote growth of wheat (*Triticum aestivum*) under water stress conditions," Plant Growth Regulation, 2012, pp. 411-420, vol. 68.
Yezerski, A., et al.,"The Effects of the Presence of Stored Product Pests on the Microfauna of a Flour Community," Journal of Applied Microbiology, 2005, pp. 507-515, vol. 98.
Zhang, J., et al. "Isolation and Characterization of Plant Growth-Promoting Rhizobacteria from Wheat Roots by Wheat Germ Agglutinin Labeled with Fluorescein Isothiocyanate", The Journal Of Microbiology, Apr. 27, 2012, vol. 50, No. 2, pp. 191-198, GenBank Accession No. JN210900.
Zhao, J.H., et al., "Bioactive secondary metabolites from *Nigrospora* sp. LLGLM003, an endophytic fungus of the medicinal plant *Moringa oleifera* Lam." World Journal of Microbiology and Biotechnology, Kluwer Academic Publishers, Feb. 12, 2012, pp. 2107-2112, vol. 28, No. 5.
Zhou, W., et al., "Effects of the Fungal Endophyte *Paecilomyces* sp. in Cotton on the Roo-Knot Nematode Meloidogyne incognita," poster dated Jan. 7, 2013.
Zimmerman, N.B., et al., "Fungal Endophyte Communities Reflect Environmental Structuring Across a Hawaiian Landscape," Proc Natl Acad Sci USA, 2012, pp. 13022-13027, vol. 109, No. 32.
Zuniga, A., et al., "Quorum Sensing and Indole-3-Acetic Acid Degradation Play a Role in Colonization and Plant Growth Promotion of *Arabidopsis thaliana* by Burkholderia phytofirmans PsJN," Mol Plant Microbe Interact., 2013, pp. 546-553, vol. 26, No. 5.
Abello, J., et al., "Agrobacterium-mediated transformation of the endophytic fungus Acremonium implicatum associated with Brachiaria grasses", Mycological Research, pp. 407-413, vol. 112, Pt 3.
Antony-Badu, S., et al., "Multiple Streptomyces species with distinct secondary metabolomes have identical 16S rRNA gene sequences." Scientific Reports 7.1, Sep. 2017, No. 7, 11089, pp. 1-8.
Bandara, WM.M.S., et al., "Interactions among endophytic bacteria and fungi: effects and potentials" Journal of Biosciences, Dec. 2006, vol. 31, No. 5, pp. 645-650.
Bragantia, et al, "Identificaqao E Avaliaqao De Rizobacterias Isoladas De Raizes De Milho," Jan. 1, 2010, pp. 905-911, Retrieved from the Internet: URL:http://www.scielo.br/pdf/brag/v69n4/v69n4a17.pdf (With English Abstract).
De Medeiros, L., et al., "Evaluation of Herbicidal Potential of Depsides from Cladosporium uredinicola an Endophytic Fungus found in Guava Fruit," J Braz. Chem. Soc , 2012, vol. 23, No. 8, p. 1551-1557.
Fox, G., et al., "How close is close: 16S rRNA sequence identity may not be sufficient to guarantee species identity." International Journal of Systematic and Evolutionary Microbiology 42.1, 1992, pp. 166-170.
NCBI, GenBankAccession No. XP_002568042, Aug. 14, 2009, 4 Pages, Berg, V.D., et al., "Genome sequencing and analysis of the filamentous fungus," Nat. Biotechnol. 26 (10), 1161-1168 (2008).
Goudjal, Y., et al., "Biocontrol of Rhizoctonia solani damping-off and promotion of tomato plant growth by endophytic actinomycetes isolated from native plants of Algerian Sahara", Microbiological Research, 2014, vol. 169, No. 1, pp. 59-65.
Guo, X., et al., "Red Soils Harbor Diverse Culturable Actinomycetes That Are Promising Sources of Novel Secondary Metabolites", Applied and Environmental Microbiology, Feb. 27, 2015, vol. 81, No. 9, pp. 3086-3103.
Hjort, K., et al., "Chitinase genes revealed and compared in bacterial isolates, DNA extracts and a metagenomic library from a phytopathogen-suppressive soil", FEMS Microbiology Ecology, Feb. 2010, vol. 71, No. 2, pp. 197-207.
Kanbar, A., et al., "Relationship between Root and Yield Morphological Characters in Rainfed Low Land Rice (*Oryza sativa* L.)," Cereal Research Communications, 2009, vol. 37, No. 2, pp. 261-268.
Ogbo, F., et al., "Some Characteristics of a Plant Growth Promoting; i*Enterobacter*/isp. Isolated from the Roots of Maize", Advances in Microbiology, Jan. 1, 2012, vol. 02, No. 03, pp. 368-374.
Partida-Martinez, L.P., et al., "Endosymbiont-Dependent Host Reproduction Maintains Bacterial-Fungal Mutualism", Current Biology, May 1, 2007, vol. 17, No. 9, pp. 773-777.
"Sequence Alignment of JQ047949 with Instant SEQ ID No. 2," Search conducted on Jan. 2, 2019, 2 pages.
Sharma et al., "Detection and identification of bacteria intimately associated with fungi of the order Sebacinales", Cellular Microbiology, Aug. 5, 2008, pp. 2235-2246, vol. 10, No. 11.
Yashiro et al., "Effect of Streptomycin Treatment on Bacterial Community Structure in the Apple Phyllosphere," Plos One, May 21, 2012, vol. 7, No. 5, 10 pages.
Abdellatif, L., et al., "Characterization of virulence and PCR-DGGE profiles of Fusarium avenaceum from western Canadian Prairie Ecozone of Saskatchewan," Canadian Journal of Plant Pathology, 2010, pp. 468-480.
Abou-Shanab, R.A., et al: "Characterization of Ni-resistant bacteria in the rhizosphere of the hyperaccumulator Myssum murale by 16S rRNA gene sequence analysis", World Journal of Microbiology and Biotechnology, vol. 26, No. 1, Aug. 15, 2009, pp. 101-108.
Amatuzzi, R.F., et al., "Universidade Federal Do Parana," Jan. 1, 2014, 52 Pages. (With English Abstract).
Aveskamp, M., et al., "DNA phylogeny reveals polyphyly of Phoma section Peyronellaea and multiple taxonomic novelties," Mycologia, 2009, vol. 101, No. 3, pp. 363-382.
Azcon, R., et al., "Selective interactions between different species of mycorrhizal fungi and Rhizobium meliloti strains, and their effects on growth, N2-fixation (15N) and nutrition of *Medicago sativa* L.," NewPhytol., 1991, vol. 117, pp. 399-404.
Bethlenfalvay, G., et al., "Mycorrhizal fungi effects on nutrient composition and yield of soybean seeds", Journal of Plant Nutrition, vol. 20, pp. 4-5, Apr. 1, 1997, pp. 581-591.
PCT International Search Report and Written Opinion, Application No. PCT/AU2015/000360, dated Aug. 5, 2015, 12 Pages.
PCT Invitation to Pay Additional Fees, PCT Application No. PCT/US2015/038110, dated Sep. 22, 2015, 8 Pages.
PCT Invitation to Pay Additional Fees, PCT Application No. PCT/US2015/038187, dated Oct. 14, 2015, 5 Pages.
PCT International Search Report and Written Opinion, PCT Application No. PCT/US2015/038187, dated Jan. 22, 2016, 36 Pages.

(56) References Cited

OTHER PUBLICATIONS

PCT Invitation to Pay Additional Fees, PCT Application No. PCT/US2015/068206, dated Apr. 12, 2016, 5 Pages.
PCT International Search Report and Written Opinion, PCT Application No. PCT/US2015/068206, dated Jun. 27, 2016, 20 Pages.
PCT International Search Report and Written Opinion, PCT Application No. PCT/US2016/030292, dated Aug. 12, 2016, 20 Pages.
PCT International Preliminary Reporton Patentability, PCT Application No. PCT/US2016/030292, dated Aug. 2, 2017, 23 Pages.
PCT International Search Report and Written Opinion, PCT Application No. PCT/US2016/030293, dated Aug. 11, 2016, 23 Pages.
PCT International Search Report and Written Opinion, PCT Application No. PCT/US2016/036504, dated Nov. 4, 2016, 18 Pages.
PCT International Search Report and Written Opinion, PCT Application No. PCT/US2016/039191, dated Nov. 29, 2016, 20 Pages.
PCT International Search Report and Written Opinion, PCT Application No. PCT/US2016/068144, dated May 18, 2017, 30 Pages.
Djordjevic, D., et al., "Microtiter Plate Assay for Assessment of Listeria monocytogenes Biofilm Formation," Annl Environ Microbiol., 2002, pp. 2950-2958, vol. 68, No. 6.
European Patent Office, Supplementary Partial European Search Report, European Patent Application No. 13874703.5, dated Jun. 21, 2016, 3 Pages.
European Patent Office, Supplementary European Search Report, European Patent Application No. 13874703.5, dated Oct. 21, 2016, 16 Pages.
European Patent Office, Communication Pursuant to Article 94(3) EPC for European Patent Application No. 13874703.5, dated Jan. 5, 2018, 4 Pages.
European Patent Office, Supplementary European Search Report, European Patent Application No. 14860187.5, dated May 24, 2017, 9 Pages.
European Patent Office, Supplementary European Search Report, European Patent Application No. 14874589.6, dated Jul. 11, 2017, 9 Pages.
European Patent Office, Communication Pursuant to Article 94(3) EPC for European Patent Application No. EP 14748326.7, dated Feb. 15, 2018, 7 Pages.
European Patent Office, Examination Report, European Patent Application No. 14748326.7, dated Jul. 19, 2017, 4 Pages.
European Patent Office, Examination Report for European Patent Application No. EP 14777213.1, dated Oct. 20, 2017, 12 Pages.
European Patent Office, Supplementary European Search Report, European Patent Application No. EP 15809264.3, dated Dec. 4, 2017, 16 Pages.
European Patent Office, Communication Pursuant to Article 94(3) EPC for European Patent Application No. 15810847.2, dated Nov. 17, 2017, 17 Pages.
European Patent Office, Supplementary European Search Report, European Patent Application No. EP 15812324.0, dated Nov. 2, 2017, 19 Pages.
United States Patent Office, Non-Final Office Action, U.S. Appl. No. 15/436,592, filed Aug. 30, 2017, 17 Pages.
United States Patent Office, Non-Final Office Action, U.S. Appl. No. 15/436,609, filed Aug. 30, 2017, 21 Pages.
Abarenkov, K., et al., "The UNITE Database for Molecular Identification of Fungi-Recent Updates and Future Perspectives," New Phvtol., 2010, pp. 281-285, vol. 186.
Abdellatif, L., et al., "Endophytic hyphal compartmentalization is required for successful symbiotic Ascomycota association with root cells," Mycological Research, 2009, pp. 782-791, vol. 113.
Abdou, R., et al., "Botryorhodines A-D, antifungal and cytotoxic depsidones from Botryosphaeria rhodina, an endophyte of the medicinal plant Bidens pilosa," Phytochemistry, 2010, vol. 71, pp. 110-116.
Adhikari, M., et al., "A New Record of Pseudeurotium bakeri from Crop Field Soil in Korea," The Korean Journal of Mycology, 2016, pp. 145-149, vol. 44.

Ahmad, F., et al., "Screening of Free-Living Rhizospheric Bacteria for Their Multiple Plant Growth Promotinq Activities," Microbiol Res., 2008, pp. 173-181, vol. 163.
Amann, R., et al., "The Identification of Microorganisms by Fluorescence in Situ Hybridisation," Curr Opin Biotechnol., 2001, pp. 231-236, vol. 12.
Apel, K., et al., "Reactive Oxygen Species: Metabolism, Oxidative Stress, and Signal Transduction," Annu Rev Plant Biol., 2004, pp. 373-399, vol. 55.
Arendt, K. R., et al., "Isolation of endohyphal bacteria from foliar Ascomycota and in vitro establishment of their symbiotic associations," Appl Environ. Microbiol., 2016, pp. 2943-2949, vol. 82, No. 10.
Ashrafuzzaman, M., et al., "Efficiency of plant growth-promoting rhizobacteria (PGPR) for the enhancement of rice growth," African Journal of Biotechnology, 2009, pp. 1247-1252, vol. 8, No. 7.
Bacon, C. W, et al., "Isolation, In Planta Detection, and Uses of Endophytic Bacteria for Plant Protection," Manual of Environmental Microbiology, 2007, pp. 638-647.
Baker, K. F., et al., "Dynamics of Seed Transmission of Plant Pathogens," Annu Rev. Phytopathol., 1966, pp. 311-334, vol. 4.
Baltruschat, H., et al., "Salt tolerance of bariey induced by the root endophyte Piriformospora indica is associated with a strong increase in antioxidants," New Phytologist., 2008, pp. 501-510, vol. 180.
Bensch, K., et al., "Species and ecological diversity within the *Cladosporium cladosporioides* complex Davidiellaceae, Capnodiales)," Studies in Mycology, 2010, pp. 1-94, vol. 67.
Block, C. C., et al., "Seed Transmission of Pantoea stewartii in Field and Sweet Corn," Plant Disease, 1998, pp. 775-780, vol. 82.
Brinkmeyer, R., et al., "Uncultured Bacterium Clone ARKMP-100 16S Ribosomal RNA Gene, Partial Sequence," NCBI GenBank Accession No. AF468334, Submitted Jan. 14, 2002.
Brodie, E.L., et al., "Uncultured Bacterium Clone BANW722 16S Ribosomal RNA Gene, Partial Sequence," NCBI GenBank Accession No. DQ264636, Submitted Oct. 25, 2005, 1 Page.
Bulgarelli, D., et al., "Structure and Functions of the Bacterial Microbiota of Plants," Annu Rev Plant Biol., 2013, pp. 807-838, vol. 64.
Büttner, D., et al., "Regulation and secretion of Xanthomonas virulence factors," FEMS Microbiology Reviews, 2010, pp. 107-133, vol. 34, No. 2.
Caporaso, J.G., et al., "Ultra-High-Throughput Microbiol Community Analysis on the Illumina HiSeq and MiSeq Platforms," ISME J., 2012, pp. 1621-1624, vol. 6.
Castillo, D., et al., "Fungal Entomopathogenic Endophytes: Negative Effects on Cotton Aphid Reproduction in Greenhouse and Field Conditions," Power Point Presentation dated Mar. 23, 2013, 21 Pages.
Cavalier-Smith, T., "A Revised Six-Kingdom System of Life," Biol Rev Camb Philos Soc., 1998, pp. 203-266, vol. 73.
Chagas, F., et al., "A Mixed Culture of Endophytic Fungi Increases Production of Antifungal Polyketides," J. Chem Ecol., Oct. 2013, pp. 1335-1342, vol. 39.
Clark, E. M., et al., "Improved Histochemical Techniques for the Detection of Acremonium coenophilum in Tall Fescue and Methods of in vitro Culture of the Fungus," J Microbiol Methods, 1983, pp. 149-155, vol. 1.
Clarridge, J., "Impact of 16S rRNA Gene Sequence Analysis for Identification of Bacteria on Clinical Microbiology and Infectious Diseases," Clinical Microbiology Reviews, Oct. 2004, pp. 840-862, vol. 17, No. 4.
Lugtenberg, B., et al., "Plant-Growth-Promoting Rhizobacteria," Ann. Rev. Microbiol., 2009, pp. 541-556, vol. 53.
Lundberg, D.S., et al., "Practical Innovations for High-Throughput Amplicon Sequencing," Nat Methods, 2013, pp. 999-1002, vol. 10, No. 10.
Ma, Y., et al., "Plant Growth Promoting Rhizobacteria and Endophytes Accelerate Phytoremediation of Metalliferous Soils," Biotechnology Advances, 2011, pp. 248-258, vol. 29.
Madi, L. et al., "Aggregation in Azospirillum brasilense Cd: Conditions and Factors Involved in Cell-to-Cell Adhesion," Plant Soil, 1989, pp. 89-98, vol. 115.

(56) References Cited

OTHER PUBLICATIONS

Mannisto, M.K., et al., "Characterization of Psychrotolerant Heterotrophic Bacteria From Finnish Lapland," Syst Appl Microbiol., 2006, pp. 229-243, vol. 29.

Mano, H., et al., "Culturable Surface and Endophytic Bacterial Flora of the Maturing Seeds of Rice Plants (Oryza saliva) Cultivated in a Paddy Field," Microbes Environ., 2006, vol. 21, No. 2.

Manter, D. K., et al., "Use of the ITS Primers, ITSIF and ITS4, to Characterize Fungal Abundance and Diversity in Mixed-Template Samples by qPCR and Length Heterogeneity Analysis," J Microbiol Methods, 2007, pp. 7-14, vol. 71.

Mao, W., et al., "Seed Treatment with a Fungal or a Bacterial Antagonist for Reducing Corn Damping-off Caused by Species of *Pythium* and *Fusarium*," Plant Disease, 1997, pp. 450-454, vol. 81, No. 5.

Marasco, R., et al., "A Drought Resistance-Promoting Microbiome is Selected by Root System Under Desert Farming," PLoS ONE, 2012, vol. 7, No. 10, 14 Pages.

Marquez, L. M., et al., "A Virus in a Fungus in a Plant: Three-Way Symbiosis Required for Thermal Tolerance," Science, 2007, pp. 513-515, vol. 315.

Mastretta, C., et al., "Endophytic Bacteria from Seeds of *Nicotiana tabacum* Can Reduce Cadmium Phytotoxicity," Intl J Phytoremediation, 2009, pp. 251-267, vol. 11.

Mateos, P. F., et al., "Cell-Associated Pectinolytic and Cellulolytic Enzymes in Rhizobium leguminosarum biovartrifolii," Appl Environ Microbiol., 1992, pp. 816-1822, vol. 58, No. 6.

McDonald, D., et al., "An Improved Greengenes Taxonomy with Explicit Ranks for Ecological and Evolutionary Analyses of Bacteria and Archaea," ISME J., 2012, pp. 610-618, vol. 6.

McGuire, K.L., et al., "Digging the New York City Skyline: Soil Fungal Communities in Green Roofs and City Parks," PloS One, 2013, vol. 8, No. 3, 13 Pages.

Medina, P., et al., "Rapid Identification of Gelatin and Casein Hydrolysis Using TCA," J Microbiol Methods, 2007, pp. 391-393, vol. 69.

Mehnaz, S., et al., "Growth Promoting Effects of Corn (*Zea mays*) Bacterial Isolates Under Greenhouse and Field Conditions," Soil Biology and Biochemistry, 2010, pp. 1848-1856, vol. 42.

Mehnaz, S., et al., "Isolation and 16S rRNA sequence analysis of the beneficial bacteria from the rhizosphere of rice," Canada Journal of Microbiology, 2001, pp. 110-117, vol. 47, No. 2.

Mei, C., et al., "The Use of Beneficial Microbial Endophytes for Plant Biomass and Stress Tolerance Improvement," Recent Patents on Biotechnology, 2010, pp. 81-95, vol. 4.

Michel, B. E., et al., "The Osmotic Potential of Polyethylene Glycol 6000," Plant Physiol., 1973, pp. 914-916, vol. 51.

Misk, A., et al., "Biocontrol of chickpea root rot using endophytic actinobacteria", Biocontrol, vol. 56, No. 5, Mar. 12, 2011, pp. 811-822, XP036215297.

Moe, L. A., "Amino Acids in the Rhizosphere: From Plants to Microbes," American Journal of Botany, 2013, pp. 1692-1705, vol. 100, No. 9.

Mohiddin, F. A., et al., "Tolerance of Fungal and Bacterial Biocontrol Agents to Six Pesticides Commonly Used in the Control of Soil Borne Plant Pathogens," African Journal of Agricultural Research, 2013, pp. 5331-5334, vol. 8, No. 13.

Mousa, W. K., et al., "The Diversity of Anti-Microbial Secondary Metabolites Produced by Fungal Endophytes: An Interdisciplinary Perspective," Front Microbiol., 2013, vol. 4, No. 65, 18 Pages.

Mundt, J.O., et al., "Bacteria Within Ovules and Seeds," Appl Environ Microbiol., 1976, pp. 694-698, vol. 32, No. 5.

Naik, B. S., et al., "Study on the diversity of endophytic communities from rice (*Oryza sativa* L.) and their antagonistic activities in vitro," Microbiological Research, 2009, pp. 290-296, vol. 164.

Naveed, M., "Maize Endophytes—Diversity, Functionality and Application Potential," University of Natural Resources and Life Sciences, 2013, pp. 1-266 and 81-87; Tables 1-3; Figure 2.

Nejad, P. et al., "Endophytic Bacteria Induce Growth Promotion and Wilt Disease Suppression in Oilseed Rape and Tomato," Biological Control, 2000, pp. 208-215, vol. 18.

Neslon, E.B., "Microbial Dynamics and Interactions in the Spermosphere," Ann. Rev. Phytopathol., 2004, pp. 271-309, vol. 42.

Nikolcheva, L.G., et al., "Taxon-Specific Fungal Primers Reveal Unexpectedly High Diversity During Leaf Decomposition in a Stream," Mycological Progress, 2004, pp. 41-49, vol. 3, No. 1.

Nimnoi, P., et al., "Co-Inoculation of Soybean (*Glycin max*) wtth Actinomycetes and Bradyrhizobium Japonicum Enhances Plant Growth, Nitrogenase Activity and Plant Nutrition," Journal of Plant Nutrition, 2014, pp. 432-446, vol. 37.

Nishijima, K.A., et al., "Demonstraling Pathogenicity of Enterobacter cloacae on Macadamia and Identifying Associated Volatiles of Gray Kernel of Macadamia in Hawaii," Plant Disease, Oct. 2007, vol. 91, No. 10, pp. 1221-1228.

Normander, B., et al., "Bacterial Origin and Community Composition in the Barley Phytosphere as a Function of Habitat and Presowing Conditions," Appl Environ Microbiol., Oct. 2000, pp. 4372-4377, vol. 66, No. 10.

Okunishi, S., et al., "Bacterial Flora of Endophytes in the Maturing Seeds of Cultivated Rice (*Oryza sativa*)," Microbes and Environment, 2005, pp. 168-177, vol. 20, No. 3.

Op De Beeck, M., et al., "Comparison and Validation of Some ITS Primer Pairs Useful for Fungal Metabarcoding Studies," Plos One, Jun. 2014, vol. 9, Issue 6, e97629, pp. 1-11.

Orole, O. O., et al., "Bacterial and fungal endophytes associated with grains and roots of maize," Journal of Ecology and the Natural Environment, 2011, pp. 298-303, vol. 3, No. 9.

Partida-Martinez, L.P., et al., "The Microbe-Free Plant: Fact or Artifact?" Front Plant Sci., 2011, vol. 2, No. 100, 16 Pages.

Pearson, W.R., et al., "Rapid and Sensitive Sequence Comparison With FASTP and FASTA," Methods Enzymol., 2011, pp. 63-98, vol. 183.

Perez-Fernandez, M.A., et al., "Simulation of Germination of Pioneer Species Along an Experimental Drought Gradient," J Environ Biol., 2006, pp. 669-685, vol. 27, No. 4.

Perez-Miranda, S., et al., "O-CAS, A Fast and Universal Method for Siderophore Detection," J Microbiol Methods, 2007, pp. 127-131, vol. 70.

Petti, C. A., "Detection and Identification of Microorganisms by Gene Amplification and Sequencing," Clinical Infectious Diseases, 2007, pp. 1108-1114, vol. 44.

Phalip, V., et al., "A Method for Screening Diacetyl and Acetoin-Producing Bacteria on Agar Plates," J Basic Microbiol., 1994, pp. 277-280, vol. 34.

Philippot, L., et al., "Going Back to the Roots: The Microbial Ecology of the Rhizosphere," Nat Rev Microbiol., Nov. 2013, pp. 789-799, vol. 11.

Hilrice Batac, Philippine Rice R&D Highlights, 2012, Area-Based R&D Projects, [online][Retrieved Aug. 11, 2016] Retrieved from the Internet URL:http://www.philrice.gov.ph/2012-rd-highlights/, 52 Pages.

Pillay, V. K., et al., "Inoculum Density, Temperature, and Genotype Effects on in vitro Growth Promotion and Epiphytic and Endophytic Colonization of Tomato (*Lycopersicon esculentum* L.) Seedlings Inoculated with a Pseudomonad Bacterium," Can J Microbiol., 1997, pp. 354-361, vol. 43.

Powell, W. A., et al., "Evidence of Endophytic Beauveria Bassiana in Seed-Treated Tomato Plants Acting as a Systemic Entomopathogen to Larval Helicoverpa zea (Lepidoptera: Noctuidae)," J. Entomol. Sci., 2009, pp. 391-396, vol. 44, No. 4.

Quadt-Hallmann, A, et al., "Bacterial Endophytes in Cotton: Mechanisms of Entering the Plant," Can J Microbiol., 1997, pp. 577-582, vol. 43.

Rasmussen, S., et al., "Grass-endophyte interactions: a note on the role of monosaccharide transport in the Neotyphodium lolii-Lolium perenne symbiosis," New Phytologist, 2012, pp. 7-12, vol. 196.

Ravel, C., et al., "Beneficial effects of Neotyphodium lolii on the growth and the water status in perennial ryegrass cultivated under nitrogen deficiency or drought stress," Agronomie, 1997, pp. 173-181, vol. 17.

(56) References Cited

OTHER PUBLICATIONS

Reiter, B., et al., "Response of Endophytic Bacterial Communities in Potato Plants to Infection with *Erwinia carotovora* subsp *atroseptica*," Appl Environ Microbiol., 2001, pp. 2261-2268, vol. 68, No. 5.

Ren, Y., et al., "Complete Genome Sequence of *Enterobacter cloacae* subsp. *cloacae* Type Strain ATCC 13047," J. Bacteriol. May 2010, vol. 192, No. 9, pp. 2463-2464.

Clough, S. J., et al., "Floral Dip: A Simplified Method for Agrobacterium-mediated Transformation of *Arabidopsis thaliana*," Plant J., 1998, pp. 735-743, vol. 16, No. 6.

Compant, S., et al., "Endophytes of Grapevines Flowers, Berries, and Seeds: Identification of Cultivable Bacteria, Comparison with Other Plant Parts, and Visualization of Niches of Colonization," Microbial Ecology, 2011, pp. 188-197, vol. 62.

Cottyn, B., et al., "Phenotypic and genetic diversity of rice seed-associated bacteria and their role in pathogenicity and biological control," Journal of Applied Microbiology, 2009, pp. 885-897, vol. 107.

Cox, C. D., "Deferration of Laboratory Media and Assays for Ferric and Ferrous Ions," Methods Enzymol., 1994, pp. 315-329, vol. 235.

Craine, J. M., et al., "Global Diversity of Drought Tolerance and Grassland Climate-Change Resilience," Nature Climate Change, 2013, pp. 63-67, vol. 3.

Dalal, J.M., et al., "Utilization of Endophytic Microbes for Induction of Systemic Resistance (ISR) in Soybean (*Glycine max* (L) Merril) Against Challenge Inoculation with R. solani," Journal of Applied Science and Research, 2014, pp. 70-84, vol. 2, No. 5.

Danhorn, T., et al., "Biofilm Formation by Plant-Associated Bacteria," Annu Rev Microbiol., 2007, pp. 401-422, vol. 61.

Daniels, R., et al., "Quorum Signal Molecules as Biosurfactants Affecting Swarming in Rhizobium etli," PNAS, 2006, pp. 14965-14970, vol. 103, No. 40.

Darsonval, A., et al., "The Type III Secretion System of *Xanthomonas fuscans* subsp. *fuscans* is involved in the Phyllosphere Colonization Process and in Transmission to Seeds of Susceptible Beans," Applied and Environmental Microbiology, 2008, pp. 2669-2678, vol. 74, No. 9.

DBGET, "Orthology: K14454," 2005, 2 pages, can be retrieved at <URL:http://www.genome.jp/dbget-bin/www bget?ko:K14454>.

De Freitas, J. R., et al., "Phosphate-Solubifizing Rhizobacteria Enhance the Growth and Yield but not Phosphorus Uptake of Canola (*Brassica napus* L.)," Biol Fertil Soils, 1997, pp. 358-364, vol. 24.

De Lima Favaro, L. C., et al., "Epicoccum nigrum P16, a Sugarcane Endophyte, Produces Antifungal Compounds and Induces Root Growth," PLoS One, 2012, pp. 1-10, vol. 7, No. 6.

De Souza, J. J., et al., "Terpenoids from Endophytic Fungi," Molecules, 2011, pp. 10604-10618, vol. 16, No. 12.

Dennis, C., et al., "Antagonistic Properties of Species Groups of Trichoderma," Trans Brit Mycol Soc, 1971, pp. 25-39, vol. 57, No. 1.

Desiro, A., et al., "Detection of a novel intracellular microbiome hosted in arbuscular mycorhizal fungi," ISME Journal, 2014, pp. 257-270, vol. 8.

Don, R.H., et al., "Properties of Six Pesticide Degradation Plasmids Isolated From Alcaligenes Paradoxus and Alcaligenes eutrophus," J Bacteriol., 1981, pp. 681-686, vol. 145, No. 2.

Dunbar, J, et al., "Uncultured Bacterium Clone NT42a2_20488 16S Ribosomal RNA Gene, Partial Sequence," NCBI GenBank Accession No. JQ378705. Submitted Nov. 8, 2012, 2 Pages.

Eberhard, A., et al., "Structural Identification of Autoinducer of Photobacterium fischeri Luciferase," Biochem., 1981, pp. 2444-2449, vol. 20.

Edgar, R. C., "Search and Clustering Orders of Magnitude Faster than BLAST," Bioinformatics, 2010, pp. 2460-2461, vol. 26, No. 19.

Ek-Ramos, M. J., "Ecology, Distribution and Benefits of Fungal Endophytes Isolated from Cultivated Cotton (*Gossypium hirsutum*) in Texas," Power Point Presentation dated Nov. 7, 2012, 27 Pages.

Ek-Ramos, M. J., et al., "Spatial and Temporal Variation in Fungal Endophyte Communities Isolated from Cultivated Cotton (*Gossypium hirsutum*)," PLoS ONE, 2013, vol. 8, No. 6, 13 Pages, e66049.

Ek-Ramos, M. J., et al., "Spatial and Temporal Variation in Fungal Endophyte Communities Isolated from Cultivated Cotton (*Gossypium hirsutum*)," Power Point Presentation dated Jan. 7, 2013.

El-Shanshoury, A. R., "Growth Promotion of Wheat Seedlings by Streptomyces atroolivaceus," Journal of Agronomy and Crop Science, 1989, pp. 109-114, vol. 163.

Emerson, D., et al., "Identifying and Characterizing Bacteria in an Era of Genomics and Proteomics," BioScience, 2008, pp. 925-936, vol. 58, No. 10.

Endre, G., et al., "A Receptor Kinase Gene Regulating Symbiotic Nodule Development," Nature, 2002, pp. 962-966, vol. 417.

Faria, D. C., et al., "Endophytic Bacteria Isolated from Orchid and Their Potential to Promote Plant Growth," World J Microbiol Biotechnol., 2013, pp. 217-221, vol. 29.

Ferrando, L., et al., "Molecular and Culture-Dependent Analyses Revealed Similarities in the Endophytic Bacterial Community Composition of Leaves from Three Rice (*Oryza sativa*) Varieties," FEMS Microbiol Ecol., 2012, pp. 696-708, vol. 80.

Fiehn, O., et al., "Metabolite Profiling for Plant Functional Genomics," Nature Biotechnol., 2000, pp. 1157-1161, vol. 8.

Fierer, N., et al., "Cross-Biome Metagenomic Analyses of Soil Microbiol Communities and Their Functional Attributes," Proc Natl Acad Sci USA, 2012, pp. 21390-21395, vol. 109, No. 52.

Fincher, G. B., "Molecular and Cellular Biology Associated with Endosperm Mobilization in Germinating Cereal Grains," Annu Rev Plant Physiol Plant Mol Biol., 1989, pp. 305-346, vol. 40.

Fisher, P. J., et al., "Fungal saprobes and pathogens as endophytes of rice (*Oryza sativa* L.)," New Phytol., 1992, pp. 137-143, vol. 120.

Fisher, P.R., et al., "Isolation and Characterization of the Pesticide-Degrading Plasmid pJP1 from Alcaligenes paradoxus," J Bacteriol., 1978, pp. 798-804, vol. 135, No. 3.

Franco, C., et al., "Actinobacterial Endophytes for Improved Crop Performance," Australasian Plant Pathology, 2007, pp. 524-531, vol. 36.

Fulthorpe, R. R., et al., "Distantly Sampled Soils Cany Few Species in Common," ISME J., 2008, pp. 901-910, vol. 2.

Gantner, S., et al., "Novel Primers for 16S rRNA-based Archaeal Community Analyses in Environmental Samples," J Microbiol Methods, 2011, pp. 12-18, vol. 84.

Gao, Z., et al., "Quantitation of Major Human Cutaneous Bacterial and Fungal Populations," J Clin Microbiol., 2010, pp. 3575-3581, vol. 48, No. 10.

Garazzino, S., et al., "Osteomyelitis Caused by Enterobacter cancerogenus Infection following a Traumatic Injury: Case Report and Review of the Literature," J Clin Microbiol., Mar. 2005, vol. 43, No. 3, pp. 1459-1461.

Gasser, I., et al., "Ecology and Characterization of Polyhydroxyalkanoate-Producing Microorganisms on and in Plants," FEMS Microbiol Ecol., 2010, pp. 142-150, vol. 70.

Gavrish, E, et al., "*Lentzea* sp. MS6 16S Ribosomal RNA Gene, Partial Sequence," NCBI GenBank Accession No. EF599958. Submitted May 9, 2007, 1 Page.

Gebhardt, J., et al., "Characterization of a single soybean cDNA encoding cytosolic and glyoxysomal isozymes of aspartate aminostransferase," Plant Molecular Biology, 1998, pp. 99-108, vol. 37.

GenBank: AF034210.1 "Glycine max aspartate aminotransferase glyoxysomal isozyme AAT1 precursor and aspartate aminotransferase cytosolic isozyme AAT2 (AAT) mRNA complete eds," NCBI, May 26, 1998, 2 Pages, can be etrieved at <URL:https://www.ncbi.nlm.nih.gov/nuccore/AF034210>.

GenBank: NP_001237541.1, "aspartate aminotransferase glyoxysomal isozyme AAT1 precursor [Glycine max]," NCBI, Oct. 29, 2016, 2 Pages, can be retrieved at <URL:https://www.ncbi.nlm.nih.gov/protein/NP_001237541.1 >.

GenEmbl Database, GenEmbl Record No. KF673660, Sandberg, et al., "Fungal endophytes of aquatic nacrophytes: diverse host-generalists characterized by tissue preferences and geographic structure," 2013, 35 Pages.

(56) References Cited

OTHER PUBLICATIONS

GenEmbl Database, GenEmbl Record No. KP991588, Huang, et al., "Pervasive effects of wildfire on foliar endophyte communities in montane forest trees," Mar. 2015, 35 Pages.

GenEmbl database, GenEmbl Record No. EU 977189, Jan. 21, 2009, 4 pages, Smith, S.A., et al., "Bioactive endophytes warrant intensified exploration and conservation," PloS One 3(8):E3052, 2008.

GenEmbl database, GenEmbl Record No. KF011597, Paenibacillus strain No. HA 13, Aug. 26, 2013, 5 Pages, Park, H.J., et al., "Isolation and characterization of humic substances-degrading bacteria from the subarctic Alaska grasslands," J Basic Microbiol, 2013.

Database Geneseq Database accession No. BAP97938 "Pantoea dispersa strain KACC91642P 16S rDNA sequence, SEQ ID 1." Aug. 15, 2013, 1 Page.

Gilmour, S. J., et al., "Overexpression of the *Arabidopsis* CBF3 Transcriptional Activator Mimics Multiple Biochemical Changes Associated with Cold Acclimation," Plant Physiol., 2000, pp. 1854-1865, vol. 124.

Giraldo, A., et al., "Phylogeny of Sarocladium (Hypocreales)," Persoonia, 2015, pp. 10-24, vol. 34.

\* cited by examiner

■ Streptomyces  ■ Microbispora
■ Micromonospora  ■ Not yet identified

A

B

FIG. 5A
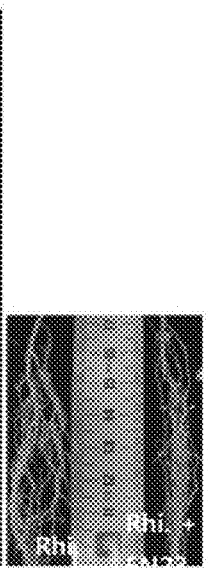
FIG. 5B
FIG. 5C
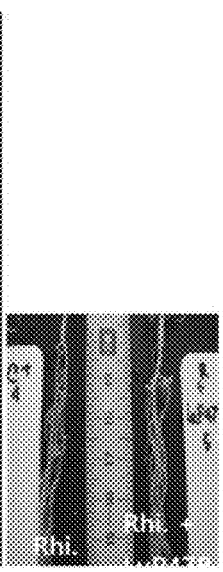
FIG. 5D
FIG. 6
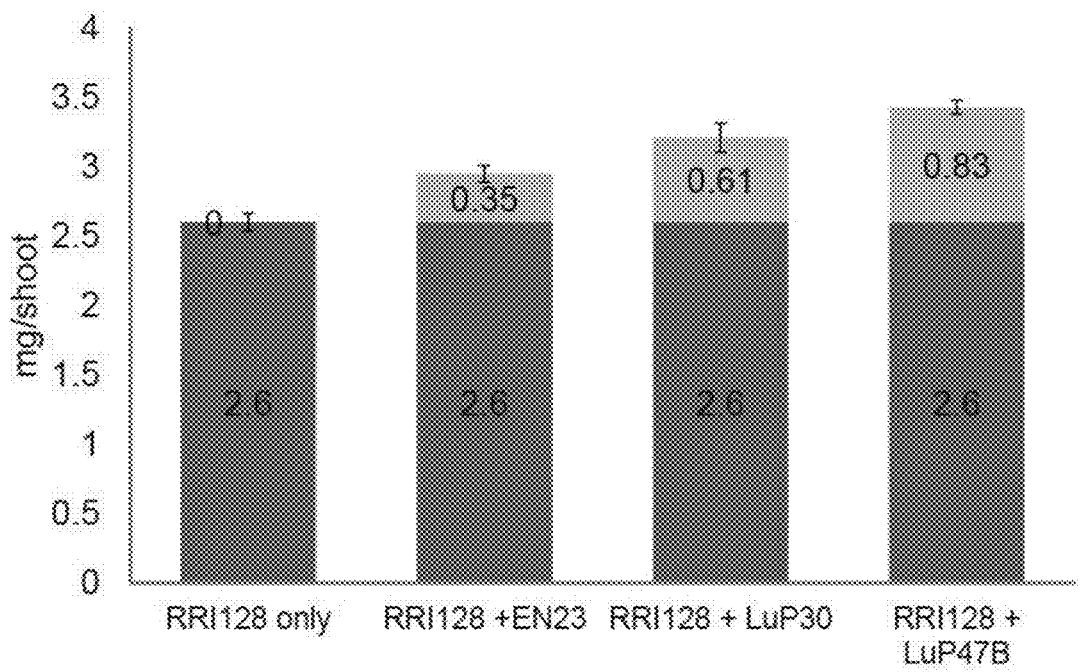

A

B

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
agagtttgat cctggctcag                                              20

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tacggytacc ttgttacgac tt                                           22

<210> SEQ ID NO 3
<211> LENGTH: 1336
<212> TYPE: DNA
<213> ORGANISM: Streptomyces sp.
<220> FEATURE:
<223> OTHER INFORMATION: LuP3

<400> SEQUENCE: 3
gtggattagt ggcgaacggg tgagtaacac gtgggcaatc tgcccttcac tctgggacaa    60
gccctggaaa cggggtctaa taccggataa tactttctcc ctcctgggag aaggttgaaa   120
gctccggcgg tgaaggatga gcccgcggcc tatcagctag ttggtggggt aatggcctac   180
caaggcgacg acgggtagcc ggcctgagag ggcgaccggc cacactggga ctgagacacg   240
gcccagactc ctacgggagg cagcagtggg gaatattgca caatgggcga agcctgatg   300 cagcgacgcc gcgtgaggga tgacggcctt cgggttgtaa acctctttca gcagggaaga   360
agcgaaagtg acggtacctg cagaagaagc gccggctaac tacgtgccag cagccgcggt   420
aatacgtagg gcgcaagcgt tgtccggaat tattgggcgt aaagagctcg taggcggctt   480
gtcacgtcgg ttgtgaaagc ccggggctta accccgggtc tgcagtcgat acgggcaggc   540
tagagtgtgg taggggagat cggaattcct ggtgtagcgg tgaaatgcgc agatatcagg   600
aggaacaccg gtggcgaagg cggatctctg ggccattact gacgctgagg agcgaaagcg   660
tggggagcga acaggattag ataccctggt agtccacgcc gtaaacgttg ggaactaagg   720
tgttggcgac attccacgtc gtcggtgccg cagctaacgc attaagttcc cgcctggggg   780
agtacggccg caaggctaaa ctcaaaggaa ttgacggggg cccgcacaag cagcggagca   840
tgtggcttaa ttcgacgcaa cgcgaagaac cttaccaagg cttgacatac accgaaaagc   900
atcagagatg gtgccccct tgtggtcggt gtacaggtgg tgcatggctg tcgtcagctc    960
gtgtcgtgag atgttgggtt aagtcccgca acgagcgcaa cccttgttct gtgttgccag  1020
catgcccttc ggggtgatgg ggactcacag gagactgccg ggtcaactc ggaggaaggt   1080 ggggacgacg tcaagtcatc atgcccctta tgtcttgggc tgcacacgtg ctacaatggc  1140
cggtacaatg agctgcgatg ccgcgaggcg agcgaatct caaaaagccg gtctcagttc   1200
ggattggggt ctgcaactcg accccatgaa gtcggagttg ctagtaatcg cagatcagca  1260

```
ttgctgcggt gaatacgttc ccgggccttg tacacaccgc ccgtcacgtc acgaaagtcg    1320
gtaacacccg aagccg                                                   1336
```

<210> SEQ ID NO 4
<211> LENGTH: 1366
<212> TYPE: DNA
<213> ORGANISM: Streptomyces sp.
<220> FEATURE:
<223> OTHER INFORMATION: LuP12A

<400> SEQUENCE: 4

```
gatgaaccac ttcggtgggg attagtggcg aacgggtgag taacacgtgg gcaatctgcc      60
cttcactctg gacaagccc tggaaacggg gtctaatacc ggataccact accgcaggca     120
tctgtggtgg ttgaaagctc cggcggtgaa ggatgagccc gcggcctatc aaggttgttg     180
gtgaggtaat ggctcaccaa ggcgacgacg gtagccggc ctgagagggc gaccggccac     240
actgggactg agacacggcc cagactccta cgggaggcag cagtggggaa tattgcacaa    300
tgggcgaaag cctgatgcag cgacgccgcg tgagggatga cggccttcgg ttgtaaacc    360 tctttcagca gggaagaagc gaaagtgacg gtacctgcag aagaagcgcc ggctaactac    420
gtgccagcag ccgcggtaat acgtagggcg caagcgttgt ccggaattat tgggcgtaaa    480
gagctcgtag gcggcttgtc acgtcgggtg tgaaagcccg gggcttaacc ccgggtctgc    540
attcgatacg ggctagctag agtgtggtag gggagatcgg aattcctggt gtagcggtga    600
aatgcgcaga tatcaggagg aacaccggtg gcgaaggcgg atctctgggc cattactgac    660
gctgaggagc gaaagcgtgg ggagcgaaca ggattagata ccctggtagt ccacgccgta    720
aacggtggga actaggtgtt ggcgacattc cacgtcgtcg gtgccgcagc taacgcatta    780
agttccccgc ctggggagta cggccgcaag gctaaaactc aaaggaattg acggggcccc    840
gcacaagcag cggagcatgt ggcttaattc gacgcaacgc gaagaacctt accaaggctt    900
gacatacgcc ggaaagcatc agagacggtg ccccccttgt ggtcggtgta caggtggtgc    960
atggctgtcg tcagctcgtg tcgtgagatg ttgggttaag tcccgcaacg agcgcaaccc   1020
ttgtcctgtg ttgccagcat gcccttcggg gtgatgggga ctcacaggag accgccgggg   1080
tcaactcgga ggaaggtggg gacgacgtca agtcatcatg ccccttatgt cttgggctgc   1140
acacgtgcta caatggcagg tacaatgagc tgcgataccg tgaggtggag cgaatctcaa   1200
aaagcctgtc tcagttcgga ttggggtctg caactcgacc ccatgaagtc ggagttgcta   1260
gtaatcgcag atcagcattg ctgcggtgaa tacgttcccg gccttgtac acaccgcccg   1320 tcacgtcacg aaagtcggta cacccgaag ccggtggcct caaccc                 1366
```

<210> SEQ ID NO 5
<211> LENGTH: 1371
<212> TYPE: DNA
<213> ORGANISM: Streptomyces sp.

<400> SEQUENCE: 5

```
cagtcgaacg atgaacactt cggtgggat tagtggcgaa cgggtgagta acacgtgggc      60
aatctgccct tcactctggg acaagcctg gaaacggggt ctaataccgg ataacacttc     120
cactcgcatg ggtggaggtt aaaagctccg gcggtgaagg atgagcccgc ggcctatcag    180
cttgttggtg aggtaatggc tcaccaaggc gacgacggg agccgcctg agagggcgac    240 cggccacact gggactgaga cacggcccag actcctacgg gaggcagcag tggggaatat    300
```

```
tgcacaatgg gcgaaagcct gatgcagcga cgccgcgtga gggatgacgg ccttcgggtt      360
gtaaacctct ttcagcaggg aagaagcgaa agtgacggta cctgcagaag aagcgccggc      420
taactacgtg ccagcagccg cggtaatacg tagggcgcaa gcgttgtccg gaattattgg      480
gcgtaaagag ctcgtaggcg gtctgtcgcg tcggatgtga agcccggggc ttaaccccg       540 ggtctgcatt cgatacgggc agactagagt gtggtagggg agatcggaat tcctggtgta      600
gcggtgaaat gcgcagatat caggaggaac accgtggcg  aaggcggatc tctgggccat      660
tactgacgct gaggagcgaa agcgtgggga gcgaacagga ttagatacc  tggtagtcca      720 cgccgtaaac ggtgggaact aggtgttggc gacattccac gtcgtcggtg ccgcagctaa      780
cgcattaagt tccccgcctg gggagtacgg ccgcaaggct aaaactcaaa ggaattgacg      840
ggggcccgca caagcagcgg agcatgtggc ttaattcgac gcaacgcgaa gaaccttacc      900
aaggcttgac atacaccgga aacggccaga gatggtcgcc cccttgtggt cggtgtacag      960
gtggtgcatg gctgtcgtca gctcgtgtcg tgagatgttg ggttaagtcc cgcaacgagc     1020
gcaacccttg ttctgtgttg ccagcatgcc cttcggggtg atgggactc  acaggagact     1080 gccggggtca actcggagga aggtggggac gacgtcaagt catcatgccc cttatgtctt     1140
gggctgcaca cgtgctacaa tggccggtac aaagagctgc gaagccgtga ggtggagcga     1200
atctcaaaaa gccggtctca gttcggattg gggtctgcaa ctcgacccca tgaagtcgga     1260
gttgctagta atcgcagatc agcattgctg cggtgaatac gttcccgggc cttgtacaca     1320
ccgcccgtca cgtcacgaaa gtcggtaaca cccgaagccg gtggcccaac c              1371

<210> SEQ ID NO 6
<211> LENGTH: 680
<212> TYPE: DNA
<213> ORGANISM: Streptomyces sp.
<220> FEATURE:
<223> OTHER INFORMATION: LuP47B

<400> SEQUENCE: 6
gtgaggtaat ggctcaccaa ggcgacgacg ggtagccggc ctgagagggc gaccggccac       60
actgggactg agacacggcc cagactccta cgggaggcag cagtggggaa tattgcacaa      120
tgggcgaaag cctgatgcag cgacgccgcg tgagggatga cggccttcgg gttgtaaacc      180
tctttcagca gggaagaagc gaaagtgacg gtacctgcag aagaagcgcc ggctaactac      240
gtgccagcag ccgcggtaat acgtagggcg caagcgttgt ccggaattat tgggcgtaaa      300
gagctcgtag gcggcttgtc acgtcgggtg tgaaagcccg ggcttaacc  ccgggtctgc      360 attcgatacg ggctagctag agtgtggtaa gggagatcgg aattcctggt gtagcggtga      420
aatgcgcaga tatcaggagg aacaccggtg gcgaaggcgg atctctgggc cattactgac      480
gctgaggagc gaaagcgtgg ggagcgaaca ggattagata ccctggtagt ccacgccgta      540
aacggtggga actaaggtgt tggcgacatt ccacgtcgtc ggtgccgcag ctaacgcatt      600
aagttcccgc ccggggggagt acggccgcaa ggctaaaact caaaggaatt gacggggggcc      660 cgcacaagca gcggagcatg                                                  680

<210> SEQ ID NO 7
<211> LENGTH: 1444
<212> TYPE: DNA
<213> ORGANISM: Streptomyces sp.
<220> FEATURE:
<223> OTHER INFORMATION: EN23

<400> SEQUENCE: 7
```

```
acgaacgctg gcggcgtgct taacacatgc aagtcgaacg atgaagccgc ttcggtggtg      60
gattagtggc gaacgggtga gtaacacgtg ggcaatctgc ccttcactct gggacaagcc     120
ctggaaacgg ggtctaatac cggataacac tctgtcccgc atgggacggg gttgaaagct    180
ccggcggtga aggatgagcc cgcggcctat cagcttgttg gtggggtaat ggcctaccaa     240
ggcgacgacg ggtagccggc ctgagagggc gaccggccac actgggactg agacacggcc    300
cagactccta cgggaggcag cagtggggaa tattgcacaa tgggcgaaag cctgatgcag    360
cgacgccgcg tgagggatga cggccttcgg gttgtaaacc tctttcagca gggaagaagc    420
gaaagtgacg gtacctgcag aagaagcgcc ggctaactac gtgccagcag ccgcggtaat    480
acgtagggcg caagcgttgt ccggaattat tgggcgtaaa gagctcgtag gcggcttgtc    540
acgtcggatg tgaaagcccg gggcttaacc ccgggtctgc attcgatacg ggctagctag    600
agtgtggtag gggagatcgg aattcctggt gtagcggtga atgcgcaga tatcaggagg     660
aacaccggtg gcgaaggcgg atctctgggc cattactgac gtctgaggag cgaaagcgtg    720
gggagcgaac aggattagat accctggtag tccacgccgt aaacgttggg aactaggtgt    780
tggcgacatt ccacgtcgtc ggtgccgcag ctaacgcatt aagttccccg cctggggagt    840
acggccgcaa ggctaaaact caaaggaatt gacgggggcc cgcacaagca gcggagcatg    900
tggcttaatt cgacgcaacg cgaagaacct taccaaggct tgacatatac cggaaagcat    960
cagagatggt gcccccttg tggtcggtat acaggtggtg catggctgtc gtcagctcgt   1020
gtcgtgagat gttgggttaa gtcccgcaac gagcgcaacc cttgttctgt gttgccagca   1080
tgcccttcgg ggtgatgggg actcacagga gactgccggg gtcaactcgg aggaaggtgg   1140
ggacgacgtc aagtcatcat gcccccttatg tcttgggctg cacacgtgct acaatggccg   1200
gtacaatgag ctgcgatgcc gcgaggcgga gcgaatctca aaaagccggt ctcagttcgg   1260
attggggtct gcaactcgac cccatgaagt cggagttgct agtaatcgca gatcagcatt   1320
gctgcggtga atacgttccc gggccttgta cacaccgccc gtcacgtcac gaaagtcggt   1380
aacacccgaa gccggtggcc caaccccttgt gggagggagc tgtcgaaggt gggactggcg   1440
attg                                                                 1444
```

<210> SEQ ID NO 8
<211> LENGTH: 1173
<212> TYPE: DNA
<213> ORGANISM: Streptomyces sp.
<220> FEATURE:
<223> OTHER INFORMATION: EN27
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other
<220> FEATURE:
<221> NAME/KEY: modified_base
<222> LOCATION: (30)..(30)
<223> OTHER INFORMATION: a, c, t, g, unknown or other
<220> FEATURE:
<221> NAME/KEY: modified_base
<222> LOCATION: (66)..(66)
<223> OTHER INFORMATION: a, c, t, g, unknown or other
<220> FEATURE:
<221> NAME/KEY: modified_base
<222> LOCATION: (68)..(68)
<223> OTHER INFORMATION: a, c, t, g, unknown or other
<220> FEATURE:

-continued

```
<221> NAME/KEY: modified_base
<222> LOCATION: (133)..(133)
<223> OTHER INFORMATION: a, c, t, g, unknown or other
<220> FEATURE:
<221> NAME/KEY: modified_base
<222> LOCATION: (146)..(146)
<223> OTHER INFORMATION: a, c, t, g, unknown or other
<220> FEATURE:
<221> NAME/KEY: modified_base
<222> LOCATION: (158)..(158)
<223> OTHER INFORMATION: a, c, t, g, unknown or other
<220> FEATURE:
<221> NAME/KEY: modified_base
<222> LOCATION: (190)..(190)
<223> OTHER INFORMATION: a, c, t, g, unknown or other
<220> FEATURE:
<221> NAME/KEY: modified_base
<222> LOCATION: (272)..(272)
<223> OTHER INFORMATION: a, c, t, g, unknown or other
<220> FEATURE:
<221> NAME/KEY: modified_base
<222> LOCATION: (342)..(342)
<223> OTHER INFORMATION: a, c, t, g, unknown or other
<220> FEATURE:
<221> NAME/KEY: modified_base
<222> LOCATION: (366)..(366)
<223> OTHER INFORMATION: a, c, t, g, unknown or other
<220> FEATURE:
<221> NAME/KEY: modified_base
<222> LOCATION: (384)..(384)
<223> OTHER INFORMATION: a, c, t, g, unknown or other
<220> FEATURE:
<221> NAME/KEY: modified_base
<222> LOCATION: (520)..(520)
<223> OTHER INFORMATION: a, c, t, g, unknown or other
<220> FEATURE:
<221> NAME/KEY: modified_base
<222> LOCATION: (523)..(523)
<223> OTHER INFORMATION: a, c, t, g, unknown or other
<220> FEATURE:
<221> NAME/KEY: modified_base
<222> LOCATION: (542)..(542)
<223> OTHER INFORMATION: a, c, t, g, unknown or other
<220> FEATURE:
<221> NAME/KEY: modified_base
<222> LOCATION: (575)..(575)
<223> OTHER INFORMATION: a, c, t, g, unknown or other
<220> FEATURE:
<221> NAME/KEY: modified_base
<222> LOCATION: (596)..(596)
<223> OTHER INFORMATION: a, c, t, g, unknown or other
<220> FEATURE:
<221> NAME/KEY: modified_base
<222> LOCATION: (808)..(808)
<223> OTHER INFORMATION: a, c, t, g, unknown or other
<220> FEATURE:
<221> NAME/KEY: modified_base
<222> LOCATION: (834)..(834)
<223> OTHER INFORMATION: a, c, t, g, unknown or other
<220> FEATURE:
<221> NAME/KEY: modified_base
<222> LOCATION: (860)..(860)
<223> OTHER INFORMATION: a, c, t, g, unknown or other
<220> FEATURE:
<221> NAME/KEY: modified_base
<222> LOCATION: (873)..(873)
<223> OTHER INFORMATION: a, c, t, g, unknown or other
<220> FEATURE:
<221> NAME/KEY: modified_base
<222> LOCATION: (895)..(895)
<223> OTHER INFORMATION: a, c, t, g, unknown or other
<220> FEATURE:
<221> NAME/KEY: modified_base
<222> LOCATION: (964)..(964)
<223> OTHER INFORMATION: a, c, t, g, unknown or other
<220> FEATURE:
<221> NAME/KEY: modified_base
<222> LOCATION: (971)..(971)
<223> OTHER INFORMATION: a, c, t, g, unknown or other
```

```
<220> FEATURE:
<221> NAME/KEY: modified_base
<222> LOCATION: (982)..(982)
<223> OTHER INFORMATION: a, c, t, g, unknown or other
<220> FEATURE:
<221> NAME/KEY: modified_base
<222> LOCATION: (1034)..(1034)
<223> OTHER INFORMATION: a, c, t, g, unknown or other
<220> FEATURE:
<221> NAME/KEY: modified_base
<222> LOCATION: (1042)..(1042)
<223> OTHER INFORMATION: a, c, t, g, unknown or other
<220> FEATURE:
<221> NAME/KEY: modified_base
<222> LOCATION: (1052)..(1052)
<223> OTHER INFORMATION: a, c, t, g, unknown or other
<220> FEATURE:
<221> NAME/KEY: modified_base
<222> LOCATION: (1055)..(1055)
<223> OTHER INFORMATION: a, c, t, g, unknown or other
<220> FEATURE:
<221> NAME/KEY: modified_base
<222> LOCATION: (1070)..(1070)
<223> OTHER INFORMATION: a, c, t, g, unknown or other
<220> FEATURE:
<221> NAME/KEY: modified_base
<222> LOCATION: (1089)..(1089)
<223> OTHER INFORMATION: a, c, t, g, unknown or other
<220> FEATURE:
<221> NAME/KEY: modified_base
<222> LOCATION: (1094)..(1094)
<223> OTHER INFORMATION: a, c, t, g, unknown or other
<220> FEATURE:
<221> NAME/KEY: modified_base
<222> LOCATION: (1112)..(1112)
<223> OTHER INFORMATION: a, c, t, g, unknown or other
<220> FEATURE:
<221> NAME/KEY: modified_base
<222> LOCATION: (1144)..(1144)
<223> OTHER INFORMATION: a, c, t, g, unknown or other

<400> SEQUENCE: 8
ttaanacatg caantcgaac gatgaacccn gtttcggtgg tggattagtg gcgaacggtg     60
agtaanangt gggcaatttg cccttcattt tggacaagcc ctggaaacgg gtttaatacc    120
ggataacatt ttntcccgca tgggangggg ttgaaagntc cggcggtgaa ggatgagccc    180
gcggcctatn agcttgttgg tggggtaatg gcctacccaa gggagacggg tagccggcct    240
gagagggcga ccggccacac tgggaatgag anacggccca gaatcctacg ggaggcagca    300
gtggggaata ttgcacaatg ggcgaaagcc tgatgcagcg angccgcgtg agggatgacg    360
gccttngggt tgtaaacctt tttnagcagg gaagaagcga aagtgacggt acctgcagaa    420
gaagcgccgg ctaaataagt gccagcagcc gcggtaataa gtagggcgca agcgttgtcc    480
ggaattattg ggcgtaaaga gcttgtaggc ggcttgtcan gtnggatgtg aaagcccggg    540
gnttaacccc gggtttgcat ttgatacggg ctagntagag tgtggtaggg gagatnggaa    600
ttcctggtgt agcggtgaaa tgcgcagata tcaggaggaa caccggtggc gaaggcggat    660
ctctgggcca ttactgacgc tgaggagcga aagcgtgggg agcgaacagg attagatacc    720
ctggtagtcc acgccgtaaa cgttgggaac taggtgttgg cgacattcca cgtcgtcggt    780
gccgcagcta acgcattaag ttccccgnct ggggagtacg gccgcaaggc taanactcaa    840
aggaattgac gggggcccgn acaagcagcg gancatgtgg cttaattcga cgcancgcga    900
agaaccttac caaggcttga catataccgg aaagcatcag agatggtgcc cccttgtgg     960 tcgntataca ngtggtgcat gnctgtcgtc acctcgtgtc gtgagatgtt gggttaagtc   1020
ccgcaacgag cgcnacccct tgntctgtgtt gncancatgc ccttcggggn tgatgggac   1080
```

| | |
|---|---:|
| tcacaggana ctgnccgggg tcaactccgg angaaggtgg gtgacgaagt caaggtcatc | 1140 |
| atgnccccett atgtcttggt gctgcacacg tgc | 1173 |

<210> SEQ ID NO 9
<211> LENGTH: 731
<212> TYPE: DNA
<213> ORGANISM: Streptomyces sp.

<400> SEQUENCE: 9

| | |
|---|---:|
| aatgggctaa gttcgaaacg attgaaccac tttcggtggg gattagtggc gaacgggtga | 60 |
| gtaacacgtg ggcaatctgc ccttcactct gggacaagcc ctggaaacgg gtctaatac | 120 |
| cggataccac taccgcaggc atctgtggtg gttgaaagct ccggcggtga aggatgagcc | 180 |
| cgcggcctat cagcttgttg gtgaggtaat ggctcaccaa ggcgacgacg ggtagccggc | 240 |
| ctgagagggc gaccggccac actgggactg agacacggcc cagactccta cgggaggcag | 300 |
| cagtggggaa tattgcacaa tgggcgaaag cctgatgcag cgacgccgcg tgagggatga | 360 |
| cggccttcgg gttgtaaacc tctttcagca gggaagaagc gaaagtgacg gtacctgcag | 420 |
| aagaagcgcc ggctaactac gtgccagcag ccgcggtaat acgtagggcg caagcgttgt | 480 |
| ccggaattat tgggcgtaaa gagctcgtag gcggcttgtc acgtcgggtg tgaaagcccg | 540 |
| gggcttaacc ccgggtctgc attcgatacg gctagctag agtgtggtag gggagatcgg | 600 |
| aattcctggt gtagcggtga atgcgcaga tatcaggagg aacaccggtg gcgaaggcgg | 660 |
| atctctgggc cattactgac gctgaggagc gaaagcgggg ggggcaaaaa agggaacccg | 720 |
| gccggggggg g | 731 |

<210> SEQ ID NO 10
<211> LENGTH: 1353
<212> TYPE: DNA
<213> ORGANISM: Streptomyces sp.

<400> SEQUENCE: 10

| | |
|---|---:|
| tcggtgggga ttagtggcga acgggtgagt aacacgtggg caatctgccc ttcactctgg | 60 |
| gacaagccct ggaaacgggg tctaataccg gataccacta ccgcaggcat ctgtggtggt | 120 |
| tgaaagctcc ggcggtgaag gatgagcccg cggcctatca gcttgttggt gaggtaatgg | 180 |
| ctcaccaagg cgacgacggg tagccggcct gagagggcga ccggccacac tgggactgag | 240 |
| acacggccca gactcctacg ggaggcagca gtggggaata ttgcacaatg ggcgaaagcc | 300 |
| tgatgcagcg acgccgcgtg agggatgacg gccttcgggt tgtaaacctc tttcagcagg | 360 |
| gaagaagcga aagtgacggt acctgcagaa gaagcgccg ctaactacgt gccagcagcc | 420 |
| gcggtaatac gtagggcgca agcgttgtcc ggaattattg ggcgtaaaga gctcgtaggc | 480 |
| ggcttgtcac gtcgggtgtg aaagcccggg gcttaacccc gggtctgcat tcgatacggg | 540 |
| ctagctagag tgtggtaggg gagatcggaa ttcctggtgt agcggtgaaa tgcgcagata | 600 |
| tcaggaggaa caccggtggc gaaggcggat ctctgggcca ttactgacgc tgaggagcga | 660 |
| aagcgtgggg agcgaacagg attagatacc ctggtagtcc acgccgtaaa cggtgggaac | 720 |
| taggtgttgg cgacattcca cgtcgtcggt gccgcagcta acgcattaag ttccccgcct | 780 |
| ggggagtacg gccgcaaggc taaaactcaa aggaattgac gggggcccgc acaagcagcg | 840 |
| gagcatgtgg cttaattcga cgcaacgcga agaaccttac caaggcttga catacgccgg | 900 |
| aaagcatcga gacggggtc cccttgtggg tcggtgtaca ggtggtgcat ggctgtcgtc | 960 |
| agctcgtgtc gtgagatgtt gggttaagtc ccgcaacgag cgcaacccct tgtcctgtgtt | 1020 |

```
gccagcatgc ccttcggggt gatggggact cacaggagac cgccggggtc aactcggagg    1080
aaggtgggga cgacgtcaag tcatcatgcc ccttatgtct tgggctgcac acgtgctaca    1140
atggcaggta caatgagctg cgataccgtg aggtggagcg aatctcaaaa agcctgtctc    1200
agttcggatt ggggtctgca actcgacccc atgaagtcgg agttgctagt aatcgcagat    1260
cagcattgct gcggtgaata cgttcccggg ccttgtacac accgcccgtc acgtcacgaa    1320
agtcggtaac acccgaagcc ggtggcccaa ccc                                 1353
```

INOCULANTS AND METHODS FOR USE THEREOF

PRIORITY CLAIM

This application is a divisional of U.S. application Ser. No. 15/320,301, filed Dec. 19, 2016, which is a National Stage of International Application No. PCT/AU2015/000360, filed on Jun. 19, 2015, published in English under PCT Article 21(2), which claims the benefit of and priority to Australian Patent Application Serial No. 2014902374, filed on Jun. 20, 2014, the contents of which are incorporated by reference in their entirety.

SEQUENCE LISTING

The instant application contains a Sequence Listing with 10 sequences which has been submitted via EFS-Web and is hereby incorporated by reference in its entirety. Said ASCII copy, created on Aug. 15, 2019 named 35212DIV_CRF_sequencelisting.txt, and is 17,111 bytes in size.

FIELD

The present invention relates to methods for enhancing at least one growth parameter of a leguminous plant via co-inoculation of a leguminous plant with at least one rhizobial microorganism together with at least one actinobacterial microorganism. In further aspects, the present invention also relates to leguminous plants co-inoculated with at least one rhizobial microorganism together with at least one actinobacterial microorganism, as well as specific actinobacterial strains and inoculant compositions which are useful in accordance with the present invention.

BACKGROUND

There are around 44 to 66 million tonnes of nitrogen fixed from atmospheric nitrogen by symbiosis of rhizobial microorganisms and legumes every year, which is nearly half of the nitrogen used in agriculture around the world.

The interaction of legume and rhizobia is highly specific and each rhizobial species has a distinct range of leguminous plant hosts for forming nodules and fixing nitrogen. Different steps of the nodulation process requires the exchange of various signals between host legumes and rhizobia.

Actinobacteria are a large group that includes different genera of Gram-positive bacteria with a high G-C content in their DNA. Actinobacteria are widely distributed in terrestrial environments and some, like the nitrogen-fixing symbionts *Frankia*, are known to form associations with plants through symbiotic relationships. Recent studies have also found that endophytic actinobacteria produced plant growth-promoting compounds such as indole-3-acetic acid (IAA) and siderophores.

Effects of actinobacteria on rhizobia and symbiosis with legumes have been noticed but not many studies have investigated this complex combination, although several studies have suggested antagonism occurring between actinobacteria and rhizobia.

For example, Antoun et al. (*Canadian Journal of Microbiology* 24: 558-562, 1978) disclosed antagonism tests between actinobacteria isolated from different soils and effective strains of rhizobia. These data demonstrated that some actinobacteria inhibit the growth of rhizobia in vitro and in planta. Specifically, thirty one percent of the 481 actinobacteria investigated inhibited two efficient rhizobia strains, *Rhizobium meliloti* A2 and S14.

In a further study, Damirgi and Johnson (*Agronomy Journal* 58: 223-224, 1966) disclosed that the number of nodules on soybeans inoculated with *Rhizobium japonicum* strains 122 and 123 in autoclaved soil were reduced by up to 35% and 53%, respectively, by treatment with the actinobacterium E8. They also isolated about 60 actinobacteria from one soil sample where there had been poor nodulation of clovers. However, 20 of 24 actinobacteria isolated from an experimental soybean field did not inhibit eight sensitive *R. japonicum* strains in in vitro tests.

Antagonism was also examined between actinobacteria and 12 strains of rhizobia from five soil samples by Patel (*Plant and Soil* 41: 395-402, 1974). It was reported that about 23-70% of the actinobacteria inhibited the rhizobia strains.

In light of the above, identification of actinobacterial inoculants that are compatible with rhizobial microorganisms and that can enhance the growth and development of leguminous plants would be desirable.

DESCRIPTION

Nucleotide and amino acid sequences are referred to herein by a sequence identifier number (SEQ ID NO:). A summary of the sequence identifiers is provided below:

| Sequence Identifier | Description |
| --- | --- |
| SEQ ID NO: 1 | 27f primer nucleotide sequence |
| SEQ ID NO: 2 | 1465r primer nucleotide sequence |
| SEQ ID NO: 3 | LuP3 16S rRNA gene nucleotide sequence |
| SEQ ID NO: 4 | LuP12A 16S rRNA gene nucleotide sequence |
| SEQ ID NO: 5 | LuP30 16S rRNA gene nucleotide sequence |
| SEQ ID NO: 6 | LuP47B 16S rRNA gene nucleotide sequence |
| SEQ ID NO: 7 | EN23 16S rRNA gene nucleotide sequence |
| SEQ ID NO: 8 | EN27 16S rRNA gene nucleotide sequence |
| SEQ ID NO: 9 | LuP8 16S rRNA gene nucleotide sequence |
| SEQ ID NO: 10 | LuP44 16S rRNA gene nucleotide sequence |

A sequence listing is also provided at the end of the specification.

In a first aspect, the present invention provides a method for enhancing at least one growth parameter of a leguminous plant, the method comprising co-inoculating the leguminous plant with:
  at least one rhizobial microorganism; and
  at least one actinobacterial microorganism;
wherein the co-inoculated leguminous plant has at least one enhanced growth parameter relative to a leguminous plant of the same taxon that has not been co-inoculated.

An "actinobacterial microorganism" as referred to herein should be understood to include any microorganism of the phylum Actinobacteria.

In some embodiments the actinobacterial microorganism is an endophytic actinobacterial microorganism. An "endophytic" actinobacterial organism should be understood to include any actinobacterial organism that is able to live within a plant for at least a part of its lifecycle without causing apparent disease. In some embodiments, an endophyte may also be able to complete its lifecycle in the absence of a plant host, and thus only be an opportunistic endophyte. In some embodiments, an endophytic actinobacterial microorganism refers to an actinobacterial microorganism which may be isolated from surface-sterilised healthy plant tissue. For reference, an example of isolation of actinobacterial endophytes from surface sterilised plant tissue is set out in Coombs & Franco (*Appl. Environ. Micro.* 69(9): 5603-5608, 2003).

In some embodiments, the actinobacterial microorganism is from a genus selected from *Streptomyces, Microbispora* or *Micromonospora*.

In some embodiments, the actinobacterial microorganism is from the genus *Streptomyces*.

In some embodiments, the actinobacterial microorganism is from a species selected from:

*Streptomyces drozdowiczii;*
*Streptomyces ciscaucasicus;*
*Streptomyces canus;*
*Streptomyces rishiriensis;*
*Streptomyces badius*; or
*Streptomyces parvus*

In some embodiments, the actinobacterial microorganism is from a species selected from *Streptomyces ciscaucasicus, Streptomyces canus* or *Streptomyces rishiriensis*.

In some embodiments, the actinobacterial microorganism comprises a 16S rRNA gene nucleotide sequence which is at least 90% identical to one or more of: SEQ ID NO: 3; SEQ ID NO: 4; SEQ ID NO: 5; SEQ ID NO: 6; SEQ ID NO: 7, SEQ ID NO: 8, SEQ ID NO: 9 and/or SEQ ID NO: 10.

In some embodiments, the actinobacterial microorganism comprises a 16S rRNA gene nucleotide sequence which is at least 90% identical to one or more of SEQ ID NO: 5 and/or SEQ ID NO: 6.

In some embodiments the actinobacterial microorganism comprises a 16S rRNA gene nucleotide sequence which is at least 90%, at least 91%, at least 91.5%, at least 92%, at least 92.5%, at least 93%, at least 93.5%, at least 94%, at least 94.5%, at least 95%, at least 95.5%, at least 96%, at least 96.5%, at least 97%, at least 97.5%, at least 98%, at least 98.1%, at least 98.2% at least 98.3%, at least 98.4%, at least 98.5%, at least 98.6%, at least 98.7%, at least 98.8%, at least 98.9%, at least 99%, at least 99.1%, at least 99.2% at least 99.3%, at least 99.4%, at least 99.5%, at least 99.6%, at least 99.7%, at least 99.8% at least 99.9% or 100% sequence identity to a comparison window of one or more of: SEQ ID NO: 3, SEQ ID NO: 4, SEQ ID NO: 5, SEQ ID NO: 6, SEQ ID NO: 7, SEQ ID NO: 8, SEQ ID NO: 9 and/or SEQ ID NO: 10.

When comparing nucleic acid sequences to calculate a percentage identity, the compared nucleic acid sequences should be compared over a comparison window of, for example, at least 100 nucleotide residues, at least 300 nucleotide residues, at least 600 nucleotide residues, at least 1000 nucleotide residues, at least 1100 nucleotide residues, at least 1200 nucleotide residues, at least 1300 nucleotide residues or at least 1400 nucleotide residues. In some embodiments, the comparison window may comprise the region in each of the compared nucleotide sequences between and including the binding sites of the 27f primer (SEQ ID NO: 1) and the 1465r primer (SEQ ID NO: 2) on the compared nucleotide sequences.

The comparison window may comprise additions or deletions (ie. gaps) of about 20% or less as compared to the reference sequence (which does not comprise additions or deletions) for optimal alignment of the two sequences. Optimal alignment of sequences for aligning a comparison window may be conducted by computerized implementations of algorithms such as the BLAST family of programs as, for example, disclosed by Altschul et al. (*Nucl. Acids Res.* 25: 3389-3402, 1997). A detailed discussion of sequence analysis can be found in Unit 19. 3 of Ausubel et al. (*Current Protocols in Molecular Biology*, John Wiley & Sons Inc, 1994-1998, Chapter 15, 1998).

A number of particularly useful actinobacterial microorganisms of the present invention have been deposited in accordance with the provisions of the Budapest Treaty on the International Recognition of the Deposit of Microorganisms for the Purposes of Patent Procedure.

The first deposited microorganism, referred to herein as *Streptomyces* sp. LuP30, has been deposited at the National Measurement Institute (NMI), Australia on 12 Dec. 2013 under accession number V13/030101.

Accordingly, some embodiments, the actinobacterial microorganism is *Streptomyces* sp. LuP30 as deposited with the National Measurement Institute, Australia under accession number V13/030101; or a mutant or derivative of said microorganism that retains the ability to enhance at least one growth parameter of a leguminous plant when the actinobacterial microorganism co-inoculated onto a leguminous plant with with a rhizobial microorganism.

The second deposited microorganism, referred to herein as *Streptomyces* sp. LuP47B, has been deposited at the National Measurement Institute (NMI), Australia on 12 Dec. 2013 under accession number V13/030100.

Accordingly, in some embodiments, the actinobacterial microorganism is *Streptomyces* sp. LuP47B as deposited with the National Measurement Institute, Australia under accession number V13/030100; or a mutant or derivative of said microorganism that retains the ability to enhance at least one growth parameter of a leguminous plant when the actinobacterial microorganism is co-inoculated onto a leguminous plant with a rhizobial microorganism.

In addition, in accordance with the present invention, two previously known organisms were also surprisingly identified to be particularly useful in accordance with the method of the present invention:

In some embodiments the actinobacterial microorganism is *Streptomyces* sp. EN23 as described in PCT publication WO/2005/003328 and deposited as AGAL Deposit No. NM03/35605; or a mutant or derivative of said microorganism that retains the ability to enhance at least one growth parameter of a leguminous plant when the actinobacterial microorganism is co-inoculated onto a leguminous plant with a rhizobial microorganism.

In some embodiments the actinobacterial microorganism is *Streptomyces* sp. EN27 as described in PCT publication WO/2005/003328 and deposited as AGAL Deposit No. NM03/35606; or a mutant or derivative of said microorganism that retains the ability to enhance at least one growth parameter of a leguminous plant when the actinobacterial microorganism is co-inoculated onto a leguminous plant with a rhizobial microorganism.

A "mutant or derivative" of the subject actinobacterial microorganisms should be understood to encompass, for example, any spontaneous or induced mutant, conjugation progeny or genetically modified form of the deposited strains which retains the ability to enhance at least one growth parameter of a leguminous plant when the actinobacterial microorganism is co-inoculated onto a leguminous plant with a rhizobial microorganism.

Mutagenisation techniques that may be used to generate derivatives or mutants include, for example, chemical mutagenesis (eg. EMS mutagenesis), ionising radiation-induced mutagenesis (eg. X-ray mutagenesis, γ-ray mutagenesis and UV mutagenesis), genetic insertion mutagenesis methods (eg. transposon mutagenesis) and the like.

As set out above, the present invention contemplates a method for enhancing at least one growth parameter of a leguminous plant.

A "growth parameter" of a leguminous plant, as referred to herein, can include any measurable characteristic of the leguminous plant.

In some embodiments, the growth parameter is a length and/or mass of a shoot of the leguminous plant.

In some embodiments, the growth parameter is a length and/or mass of a root of the leguminous plant.

In some embodiments, the growth parameter is a number and/or mass of nodules of the leguminous plant.

In some embodiments, the growth parameter is a number and/or mass of seed pods and/or seed produced by the leguminous plant.

In some embodiments, the growth parameter is a concentration and/or amount of a nutrient in the leguminous plant.

In some embodiments, the nutrient is selected from: Boron, Calcium, Copper, Magnesium, Manganese, Phosphorous, Sodium, Sulphur, Nitrogen and/or Zinc.

The concentration and/or amount of the nutrient may be measured using any method known in the art to be suitable for the relevant nutrient. Such methods may include, for example, the methods described by: Kirsten (*Organic Elemental Analysis—Ultramicro, Micro and Traces Methods*. Academic Press, New York, 1984); Horwath (*Instrumental Organic Analylsis*. Academic Press, New York, 1977); Colombo and Giazzi (*American Laboratory* 38-45, 1982); Fraisse and Schmidt (*J. Microchem.* 22: 109-130, 1977); Hegedus (*Microchim. Acta* 441-446, 1977); and Baur and Dirscherl (*Microchim. Acta* 1: 299-244, 1980).

In some embodiments, the nutrient is Nitrogen.

In some embodiments, the growth parameter is a germination rate of a leguminous plant seed. In some embodiments, "germination rate" may refer to the proportion of seeds of a leguminous plant that successfully germinate. In some embodiments "germination rate" may refer to a speed of germination of a leguminous plant seed, and/or a proportion of seeds of a leguminous plant that successfully germinate per unit time, for example the proportion of seeds of a leguminous plant that successfully germinate per 1, 2, 3, 4, 5, 6, 7, 8, 9, 10, 11, 12, 14, 15, 16, 17, 18, 19 or 20 days.

The "germination rate" of a leguminous plant seed may be assessed using any suitable laboratory based or field based method, as would be readily ascertained by those skilled in the art.

As set out above, the present invention contemplates "enhancement" of the one or more growth parameters of the leguminous plant. "Enhancement" of a growth parameter should be understood to include any improvement in a growth parameter in a co-inoculated leguminous plant relative to a leguminous plant of the same taxon that has not been co-inoculated in accordance with the method of the present invention.

In some embodiments, enhancement of a growth parameter will include an increase in the measured value of the growth parameter. For example, an increase in any of:
 a length and/or mass of a shoot;
 a length and/or mass of a root;
 a number and/or mass of nodules;
 a number and/or mass of seed pods and/or seed;
 a concentration and/or amount of a nutrient; or
 a germination rate.
should be considered an enhancement of such growth parameters.

In some embodiments, enhancement of a growth parameter may comprise enhancement within a particular time period. For example, in some embodiments, enhancement of the growth parameter may comprise enhancement over a time period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90 or 100 days.

In some embodiments, an "increase" in a growth parameter may include, for example, a 1%, 5%, 10%, 20%, 30%, 40%, 50%, 60%, 70%, 80%, 90%, 100%, 2-fold, 5-fold, 10-fold, 20 fold, 50-fold, 100-fold increase in the growth parameter in a co-inoculated leguminous plant relative to a leguminous plant of the same taxon that has not been co-inoculated.

In some embodiments, however, "enhancement" of the growth parameter may include a decrease in the measured value of the growth parameter. For example a decrease in the concentration and/or amount of a pathogen, disease symptom and/or toxin in the plant, and or a decrease in the time of germination of a leguminous plant seed, may be considered "enhancement" of such growth parameters.

In some embodiments, an "decrease" in a growth parameter may include, for example, a 1%, 5%, 10%, 20%, 30%, 40%, 50%, 60%, 70%, 80%, 90%, 91%, 92%, 93%, 94%, 95%, 96%, 97%, 98%, 99%, 100% decrease in the growth parameter in a co-inoculated leguminous plant relative to a leguminous plant of the same taxon that has not been co-inoculated.

As set out above, the present invention contemplates co-inoculating the leguminous plant with at least one rhizobial microorganism and at least one actinobacterial microorganism.

A "rhizobial microorganism" as referred to herein may include any microorganism that is capable of fixing nitrogen after becoming established in a root nodule of a leguminous plant.

Rhizobial microorganisms are a paraphyletic group that generally fall into two classes of the proteobacteria, the alpha- and beta-proteobacteria. Most rhizobial microorganisms belong to the order Rhizobiales, but several rhizobia occur in distinct bacterial orders of the proteobacteria.

Examples of rhizobial microorganisms include:
 *Bradyrhizobium* spp., such as *B. canariense, B. elkanii, B. japonicum, B. liaoningense* and *B. yuanmingense;*
 *Ochrobactrum* spp., such as *O. cytisi* and *O. lupini;*
 *Azorhizobium* spp., such as *A. caulinodans* and *A. doebereinerae;*
 *Devosia* spp., such as *D. neptuniae;*
 *Methylobacterium* spp., such as *M. nodulans;*
 *Mesorhizobium* spp., such as *M. albiziae, M. amorphae, M. chacoense, M. cicero, M. huakuii, M. loti, M. mediterraneum, M. plurifarium, M. septentrionale, M. temperatum,* and *M. tianshanense;*
 *Phyllobacterium* spp., such as *P. ifriqiyense, P. leguminum,* and *P. trifoli;*
 *Rhizobium* spp., such as *R. cellulosilyticum, R. daejeonense, R. etli, R. galegae, R. gallicum, R. giardinii, R. hainanense, R. huautlense, R. indigoferae, R. leguminosarum, R. loessense, R. lupini, R. lusitanum, R. mongolense, R. miluonense, R. sullae, R. tropici, R. undicola* and *R. yanglingense;*
 *Sinorhizobium* spp. such as *S. abri, S. adhaerens, S. americanum, S. arboris, S. fredii, S. indiaense, S. kostiense, S. kummerowiae, S. medicae, S. meliloti, S. mexicanus, S. morelense, S. saheli, S. terangae* and *S. xinjiangense;*
 *Ensifer* spp.;

*Burkholderia* spp., such as *B. caribensis, B. dolosa, B. mimosarum, B. phymatum* and *B. tuberum;*

*Cupriavidus* spp., such as *C. taiwanensis;* and

*Herbaspirillum* spp., such as *H. lusitanum.*

In some embodiments, the rhizobial microorganism is a *Rhizobium* spp., a *Sinorhizobium* spp. or *Ensifer* spp., or a *Bradyrhizobium* spp.

In some embodiments, the rhizobial microorganism is of the species *Sinorhizobium meliloti* or *Sinorhizobium medicae*. In some embodiments, the rhizobial microorganism is selected from the list of: *S. meliloti* strain RRI128 (referred to hereafter as 'RRI128'), *Sinorhizobium* strain SRDI736 (referred to hereafter as 'SRDI736') or *S. medicae* strain WSM1115G (referred to hereafter as 'WSM1115G').

In some embodiments, the rhizobial microorganism is of the species *Rhizobium leguminosarum*. In some embodiments, the rhizobial microorganism is selected from the list of: *R. leguminosarum* bv. *viciae* (referred to hereafter as 'WSM1455') or *R. leguminosarum* bv. *trifolii* (referred to hereafter as 'WSM1325').

In some embodiments, the rhizobial microorganism is of the species *Bradyrhizobium* sp. *lupini* or *Bradyrhizobium japonicum*. In some embodiments, the rhizobial microorganism is selected from the list of: *Bradyrhizobium* sp. *lupini* strain WSM471 (referred to hereafter as 'WSM471') or *Bradyrhizobium japonicum* strain CB1809 (referred to hereafter as 'CB1809').

A range of rhizobial microorganisms are available from a range of commercial culture collections, as would be readily ascertained by those skilled in the art. In relation to a range of the rhizobial microorganisms described herein, these organisms can be accessed from the rhizobium culture collection of the South Australian Research & Development Institute (Plant Research Centre, Hartley Grove, Urrbrae SA 5064, Australia; www.sardi.sa.gov.au).

As set out above, the present invention contemplates a method for enhancing at least one growth parameter of a leguminous plant.

A "leguminous plant" as referred to herein should be understood as any member of the Fabaceae (or Leguminosae) that can form nodules when infected with a rhizobial microorganism.

Examples of leguminous plants include:

*Medicago* spp., such as *Medicago sativa* (also referred to as lucerne or alfalfa);

*Pisum* spp., such as *Pisum abyssinicum* (syn. *P. sativum* subsp. *abyssinicum*), *Pisum fulvum, Pisum sativum, Pisum sativum* subsp. *elatius* (syn. *P. elatius, P. syriacum*) and *Pisum sativum* subsp. *sativum;*

*Glycine* spp., such as *Glycine max, Glycine albicans, Glycine aphyonota, Glycine arenaria, Glycine argyrea, Glycine canescens, Glycine clandestine, Glycine curvata, Glycine cyrtoloba, Glycine falcate, Glycine gracei, Glycine hirticaulis, Glycine hirticaulis* subsp. *leptosa, Glycine lactovirens, Glycine latifolia, Glycine latrobeana, Glycine microphylla, Glycine montis-douglas, Glycine peratosa, Glycine pescadrensis, Glycine pindanica, Glycine pullenii, Glycine rubiginosa, Glycine stenophita, Glycine syndetika, Glycine tabacina, Glycine tomentella* and *Glycine soja;*

*Cicer* spp., such as *Cicer arietinum;*

*Vicia* spp., such as *V. faba;*

*Vigna* spp., such as *V. aconitifolia, V. angularis, V. mungo, V. radiate, V. subterranean, V. umbellatta* or *V. unguiculata*

*Lathyrus* spp., such as *Lathyrus sativus* or *Lathyrus tuberosus;*

*Lens* spp., such as *L. culinaris*

*Lablab* spp., such as *L. purpureus;*

*Phaseolus* spp., such as *P. acutifolius, P. coccineus, P. lunatus, P. vulgaris, P. polyanthus* or *P. Dumosus;*

*Psophocarpus* spp., such as *P. tetragonolobus;*

*Cajanus* spp., such as *C. cajan;*

*Stizolobium* spp.;

*Cyamopsis* spp., such as *C. tetragonoloba;*

*Canavalia* spp., such as *C. ensiformis* or *C. gladiata;*

*Macrotyloma* spp., such as *M. uniflorum;*

*Lupinus* spp., such as *L. mutabilis* or *L. albus;* or

*Erythrina* spp., such as *E. herbacea.*

*Trifolium* spp., such as *Trifolium subterraneum*

In some embodiments, the leguminous plant is a *Medicago* spp. plant. In some embodiments, the leguminous plant is a *Medicago sativa*, lucerne or alfalfa plant.

In some embodiments, the leguminous plant is a *Trifolium* sp. In some embodiments, the leguminous plant is a *Trifolium subterraneum* plant.

In some embodiments, the leguminous plant is *Pisum* sp. In some embodiments, the leguminous plant is a *Pisum sativum* plant.

In some embodiments, the leguminous plant is a *Glycine* sp. In some embodiments, the leguminous plant is a *Glycine max* plant.

As set out above, the present invention contemplates co-inoculating a leguminous plant with a rhizobial microorganism and an actinobacterial microorganism. As referred to herein, "co-inoculating" should be understood to include any method or process wherein a leguminous plant (including a leguminous plant seed) is brought into contact with a rhizobial microorganism and an actinobacterial microorganism. In some embodiments co-inoculation may comprise the rhizobial microorganism and/or actinobacterial microorganism being applied to a leguminous plant seed. Examples of leguminous plant seed inoculation are described by Hartley et al. (*Crop and Pasture Science* 63: 858-865, 2012). In some embodiments co-inoculation may comprise the rhizobial microorganism and/or actinobacterial microorganism being applied to soil in which a leguminous plant is growing. In some embodiments, co-inoculation may comprise the rhizobial microorganism and/or actinobacterial microorganism being applied to root and/or shoot tissue of a leguminous plant.

In some embodiments, "co-inoculating" may also comprise where the actinobacterial microorganism or rhizobial microorganism is pre-existing in the environment (eg. soil) into which a leguminous plant is grown. For example, co-inoculation may comprise application of an actinobacterial microorganism to a plant or soil and wherein a natural or pre-existing rhizobial microorganism in the soil co-inoculates the plant.

In some embodiments, the leguminous plant is exposed to a pathogen and, when exposed to the pathogen, the co-inoculated leguminous plant has at least one enhanced growth parameter relative to a leguminous plant of the same taxon that has not been co-inoculated.

In some embodiments, the pathogen is a root pathogen. A "root pathogen" as referred to herein should be understood to include any leguminous plant pathogen that infects and/or damages the roots of the leguminous plant. Examples of root pathogens of leguminous plants include fungal, oomycete, bacterial and/or nematode pathogens.

In some embodiments, the root pathogen is a nematode root pathogen such as a *Pratylenchus* spp., such as *P. neglectus* or *P. thornei*.

In some embodiments, the root pathogen is an oomycete root pathogen such as a *Phytophthora* spp., such as *P. sojae*.

In some embodiments, the pathogen is a fungal pathogen. Leguminous plants may be subject to attack by a range of fungal pathogens, including fungal root pathogens. Examples of such pathogens include *Rhizoctonia* spp., *Pythium* spp. or *Aphanomyces* spp.

In some embodiments, the pathogen is a *Rhizoctonia* sp. In some embodiments, the pathogen is *Rhizoctonia solani*. In some embodiments the pathogen is *Rhizoctonia solani* AG8.

In a second aspect, the present invention provides a leguminous plant, a leguminous plant part or leguminous plant reproductive material, co-inoculated with at least one rhizobial microorganism and at least one actinobacterial microorganism.

The leguminous plant contemplated in the second aspect of the invention may be any leguminous plant as hereinbefore described with reference to the first aspect of the invention.

Reference herein to a plant, plant part or plant reproductive material should be understood to encompass tissues, organs, whole organisms and parts thereof. In some embodiments, the term plant, plant part, or plant reproductive material should also be understood to encompass multicellular aggregations of cultured cells such as colonies, plant calli, suspension cultures and the like.

In some embodiments, the leguminous plant part or plant reproductive material may include a leguminous plant seed. As referred to herein, a plant "seed" should be understood to refer to a mature or immature plant seed. As such, the term "seed" includes, for example, immature seed carried by a maternal plant or seed released from the maternal plant. In some embodiments, the term "seed" may encompass any seed plant sporophyte between the developmental stages of fertilisation and germination.

In some embodiments, the actinobacterial microorganism contemplated in accordance with the second aspect of the invention is an actinobacterial microorganism as hereinbefore described with reference to the first aspect of the invention.

In some embodiments, the rhizobial microorganism contemplated in accordance with the second aspect of the invention is a rhizobial microorganism as hereinbefore described with reference to the first aspect of the invention.

In a third aspect, the present invention provides an isolated actinobacterial microorganism as deposited with the National Measurement Institute, Australia under accession number V13/030101; or a mutant or derivative of said microorganism that retains the ability to enhance at least one growth parameter of a leguminous plant when the actinobacterial microorganism is co-inoculated onto a leguminous plant with a rhizobial microorganism.

In a fourth aspect, the present invention provides an isolated actinobacterial microorganism as deposited with the National Measurement Institute, Australia under accession number V13/030100; or a mutant or derivative of said microorganism that retains the ability to enhance at least one growth parameter of a leguminous plant when the actinobacterial microorganism is co-inoculated onto a leguminous plant with a rhizobial microorganism.

In some embodiments, the present invention provides any of the hereinbefore described isolated actinobacterial microorganisms when used according to the method of the first aspect of the invention.

In a fifth aspect, the present invention also provides an inoculant composition comprising an actinobacterial microorganism.

In some embodiments, the actinobacterial microorganism comprises an actinobacterial microorganism as hereinbefore described with respect to the first aspect of the invention.

In some embodiments, the inoculant composition further comprises a rhizobial microorganism. In some embodiments, the rhizobial microorganism comprises a rhizobial microorganism as hereinbefore described with respect to the first aspect of the invention.

In some embodiments, the inoculant composition comprises a carrier or additive. The carrier or additives used will depend on the nature of the inoculant composition. For example, the inoculant composition may be in the form of a liquid composition, a solid composition (such as a powder, pellet or granular composition) a seed coating or the like.

The inoculant compositions of the present invention may be adapted to be applied to a leguminous plant in any suitable way. For example, the inoculant composition could be adapted to be applied as a seed coating, applied as a solid or liquid composition to the foliage or roots of a plant, or applied as a solid or liquid composition to soil before, during or after sowing of a leguminous plant.

A range of useful carriers or additives would be readily apparent to those of skill in the art and may include, for example: one or more gums (including xanthan gum), clay or peat based carriers, one or more nutrients including carbon or nitrogen sources, one or more antifungal or antibacterial agents, one or more seed coating agents, one or more wetting agents and the like.

In some embodiments, the present invention provides the hereinbefore described inoculant composition when used according to the method of the first aspect of the invention.

The present invention is further described with reference to the following non-limiting examples:

BRIEF DESCRIPTION OF THE FIGURES AND TABLES

Figure 4:
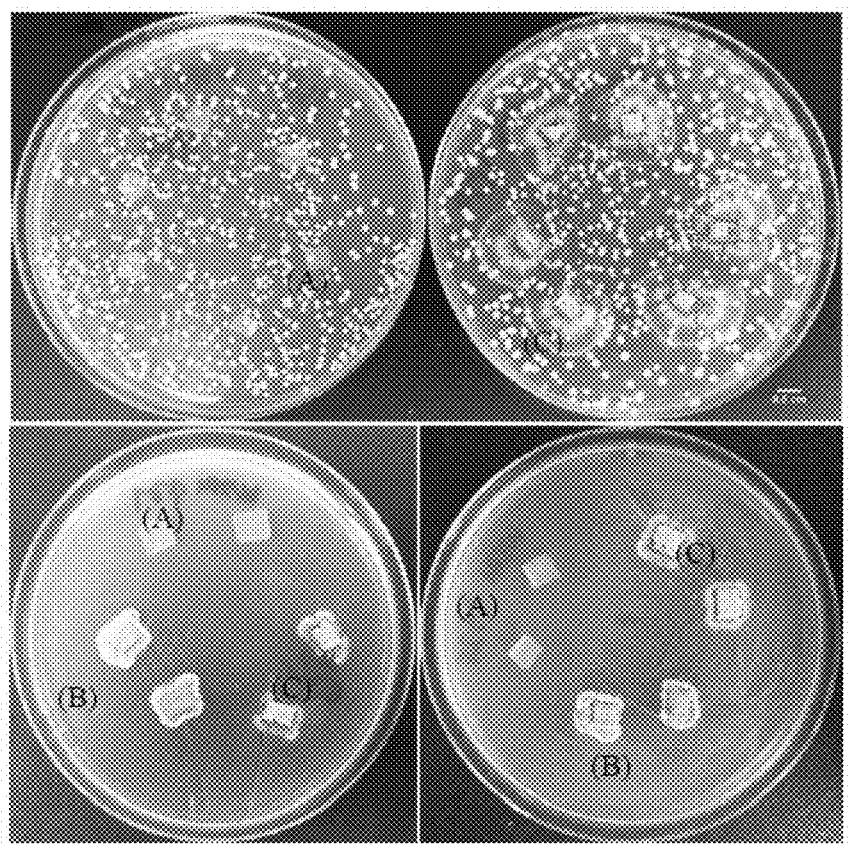
Figure 4:
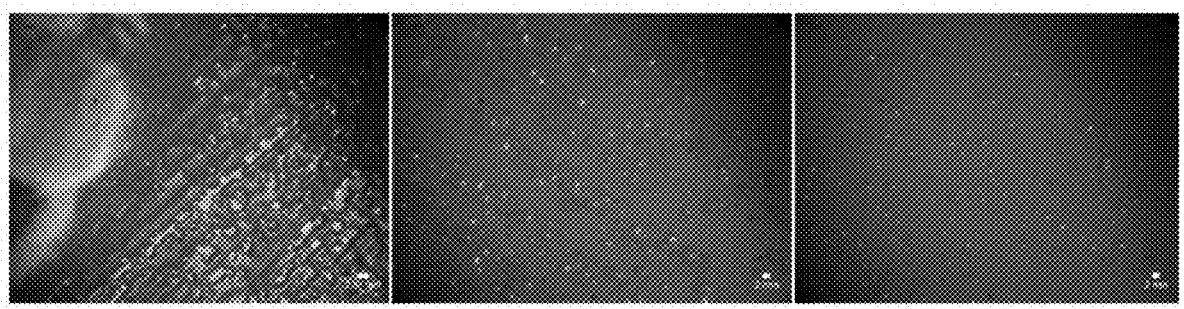

FIG. 4 shows the stimulation of the growth of *Rhizobium leguminosarum* bv. *trifolii* strain WSM 1325 and *Bradyrhizobium lupini* strain WSM 471 by two actinobacteria LuP30 and LuP47B after 5 days growth of the rhizobia on YMA medium at different concentrations of *Rhizobium*. Panel A—From top to bottom and left to right: WSM 1325 at 2 weeks old with $10^3$ CFU per plate; LuP30 plugs on WSM 1325 with bigger colonies; WSM 471 at 7 days old with $10^5$ CFU per plate (A) ISP2 control plugs, (B) LuP47B plugs and (C) LuP30 plugs; WSM 1325 at 7 days old with $10^5$ CFU per plate. Panel B—From right to left images the increase of the growth of two rhizobia when closer to the plug of LuP30 or LuP47B shown under microscopy.

FIGS. 5A-5D shows enhanced plant growth, nodule sizes and nitrogen fixation in lucerne plants co-inoculated with selected endophytic actinobacteria and *S. meliloti* RRI128.

(Rhi.=*Rhizobium* RRI128). FIGS. 5A and 5B show plants and nodules in the seventh week after adding the rhizobia. FIGS. 5C and 5D show plants and nodules in 45 days after adding the rhizobia.

FIG. 6 shows the total nitrogen fixed in the shoots of lucerne inoculated with endophytic actinobacteria EN23, LuP30 and LuP47B together with *Rhizobium* RRI128.

Figure 7:
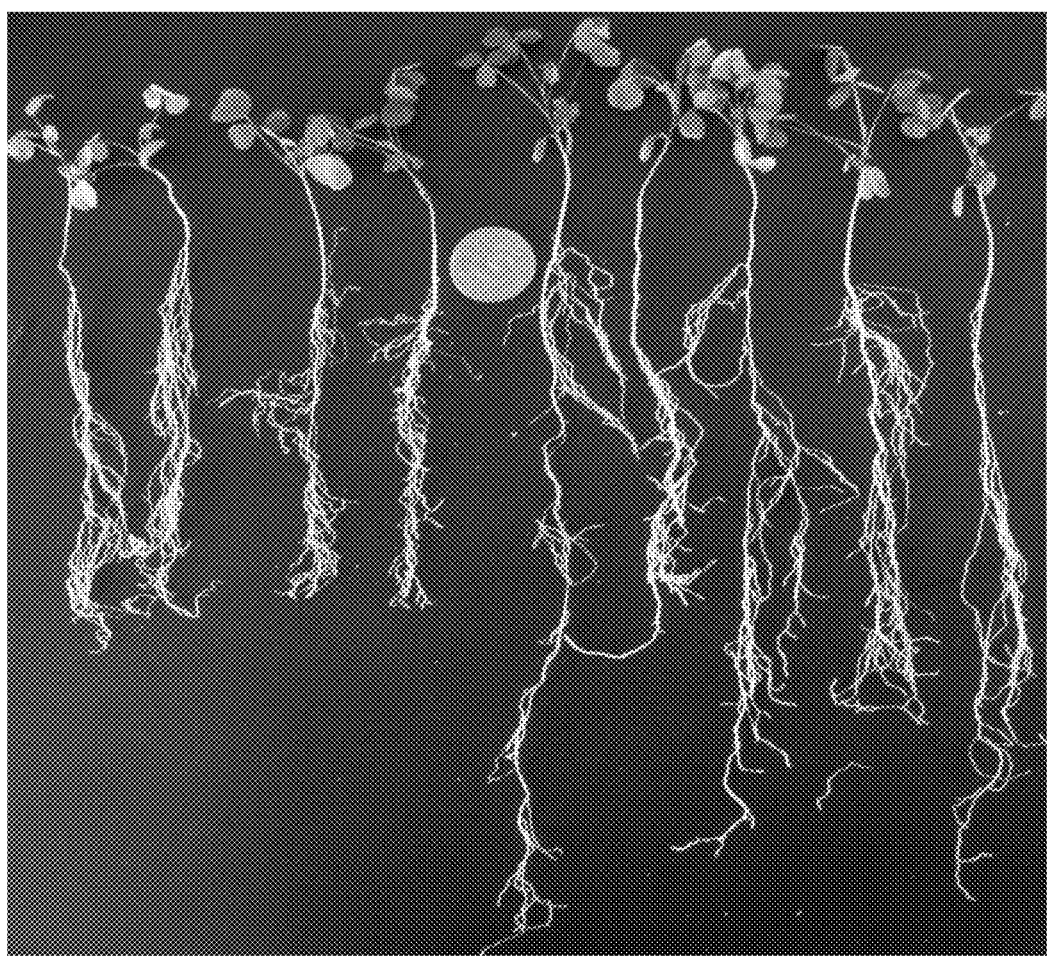

FIG. 7 shows the effect of endophytic actinobacteria on the symbiosis of rhizobia and lucerne under nutrient limited conditions. Two surface sterilised lucerne seeds were sown into 65 g of autoclaved washed sand in a 50 ml tube containing 10 mls of McKnight's+N starter (300 mg for 20 L) was added at day 0 and MQ water as required later. One seedling was kept in each tube with 12 h light and 12 h dark and five replicates for each treatment. One ml (around $10^8$ cfu/ml) of the *S. meliloti* RRI 128 was added into each seedling for treatment plants after 6 days, and the plants were grown up to 7 weeks. Left plants were inoculated with RRI 128 only while right plants were co-applied with LuP5B and RRI 128

Figure 8:
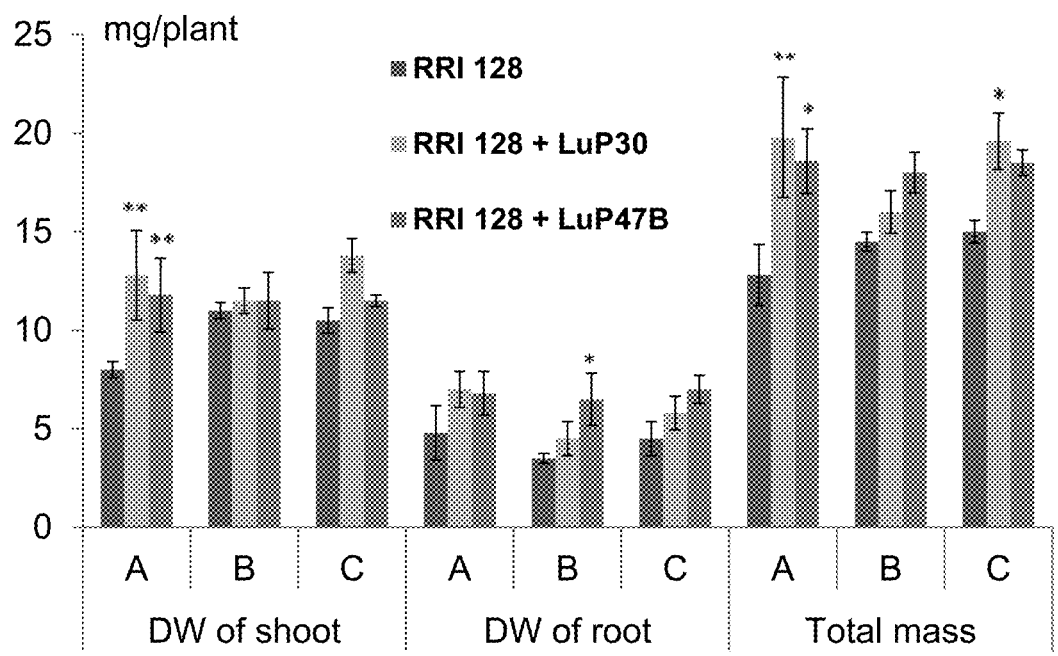
Figure 8:
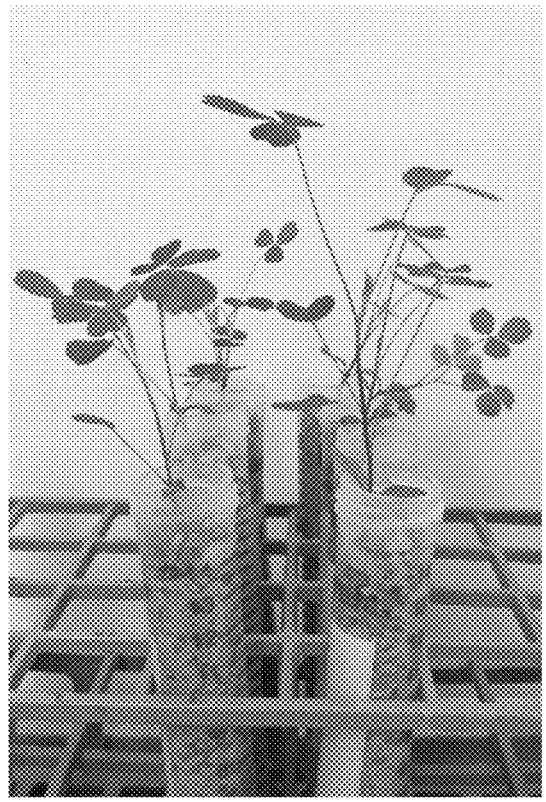

FIG. 8 shows the response of lucerne plants co-inoculated with LuP30 or LuP47B and different concentrations of *S. meliloti* RRI 128. Panel A is a graphical representation showing shoot, root and total plant dry weights after three weeks at three rhizobia concentrations: (A) $5 \times 10^2$, (B) $5 \times 10^4$, (C) $5 \times 10^6$ CFU·ml$^{-1}$. Error bars: Mean±S.E. Panel B is a photograph of representative lucerne plants in tubes three weeks after inoculation with *S. meliloti* RRI 128 at $5 \times 10^2$ CFU·ml$^{-1}$. Left—*S. meliloti* RRI 128 alone; right—*S. meliloti* RRI 128 plus LuP30.

Figure 9:
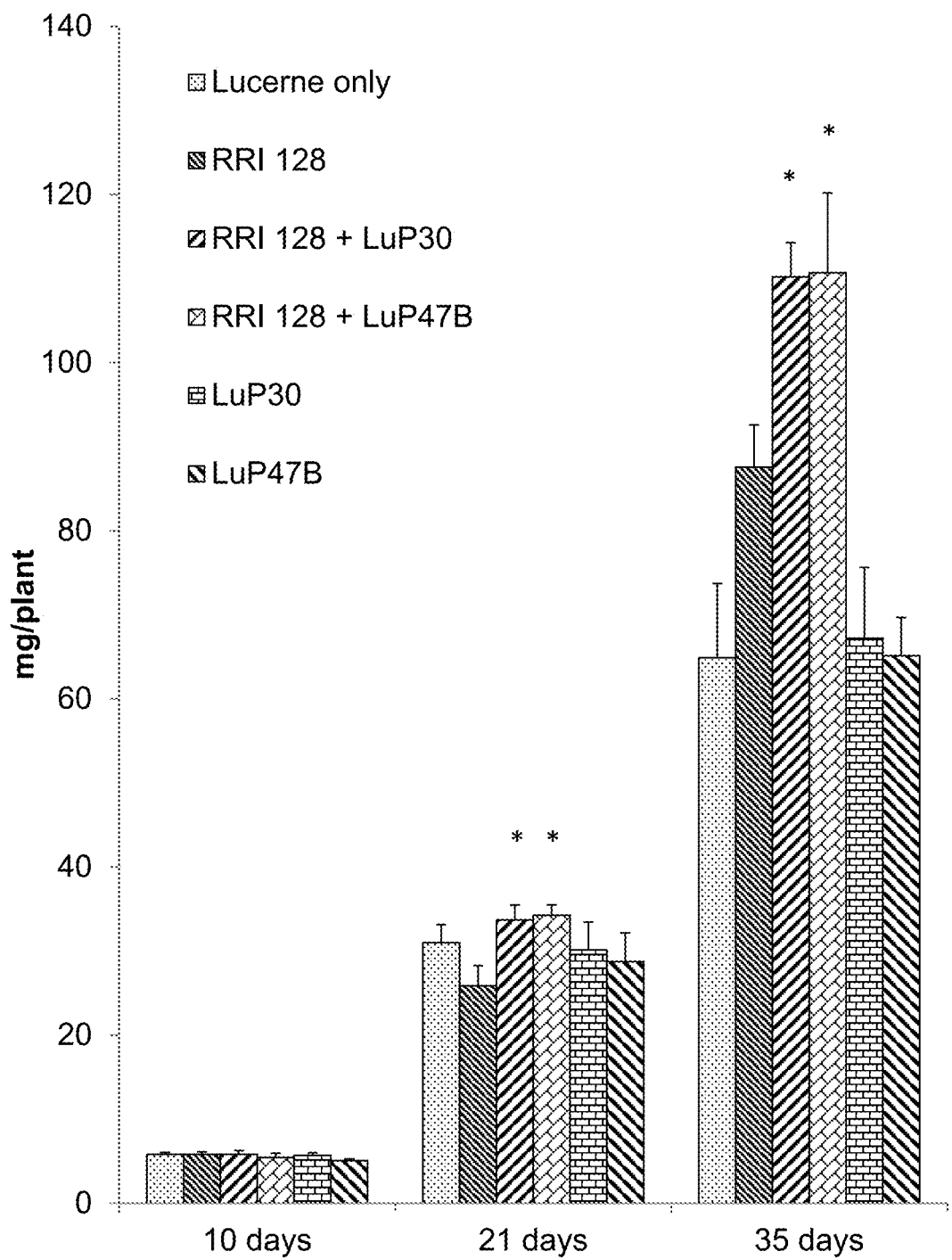

FIG. 9 is a graphical representation showing lucerne shoot dry weight response by impact of LuP30 and LuP47B after 10, 21 and 35 days inoculation with *S. meliloti* RRI 128. Asterisks indicate significant differences at P<0.05 (*) or P<0.01 (**).

Figure 10:
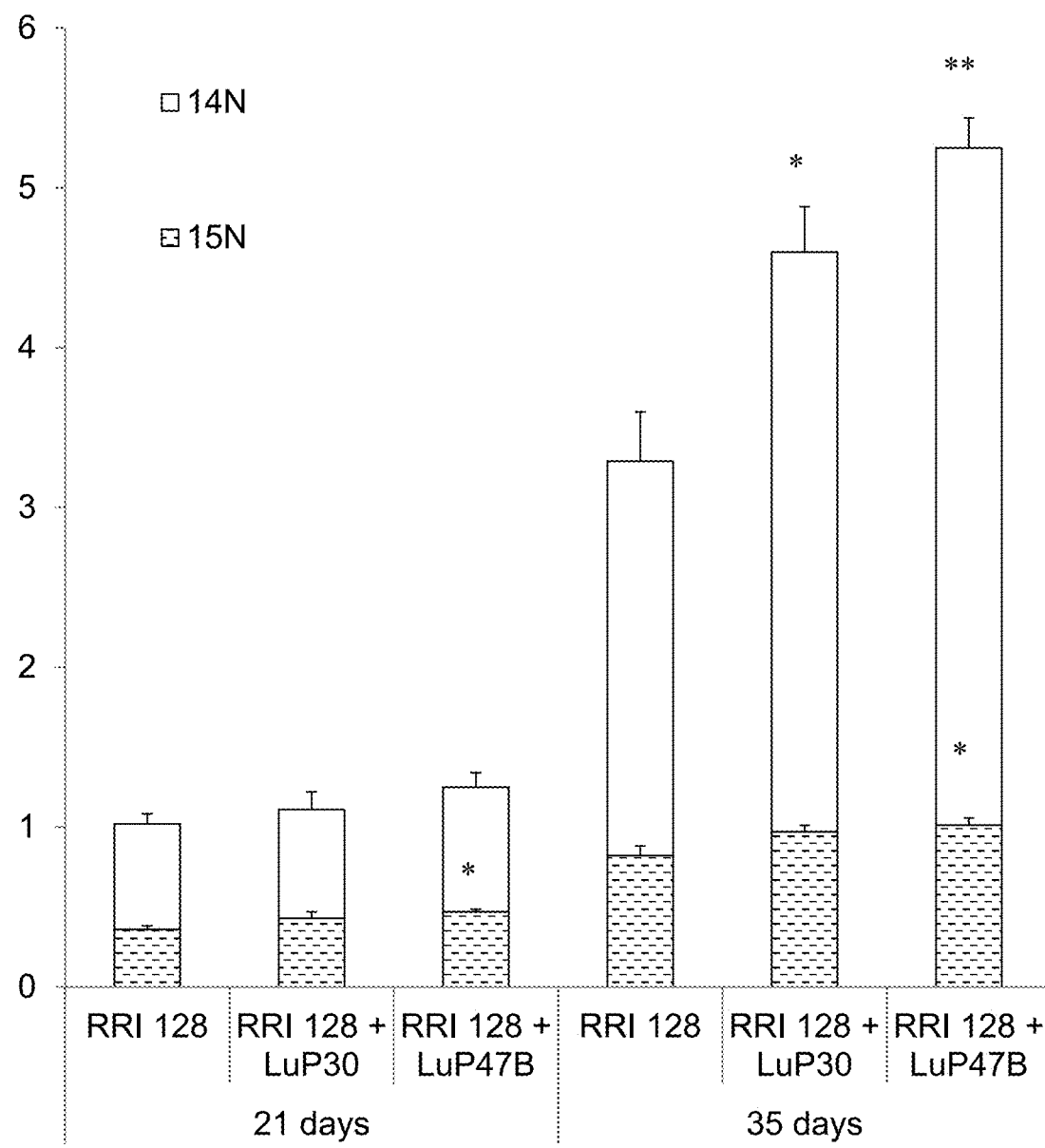

FIG. 10 is a graphical representation showing accumulation of N ($^{14}$N and $^{15}$N) in lucerne plants inoculated with rhizobia and actinobacteria.

Figure 11:
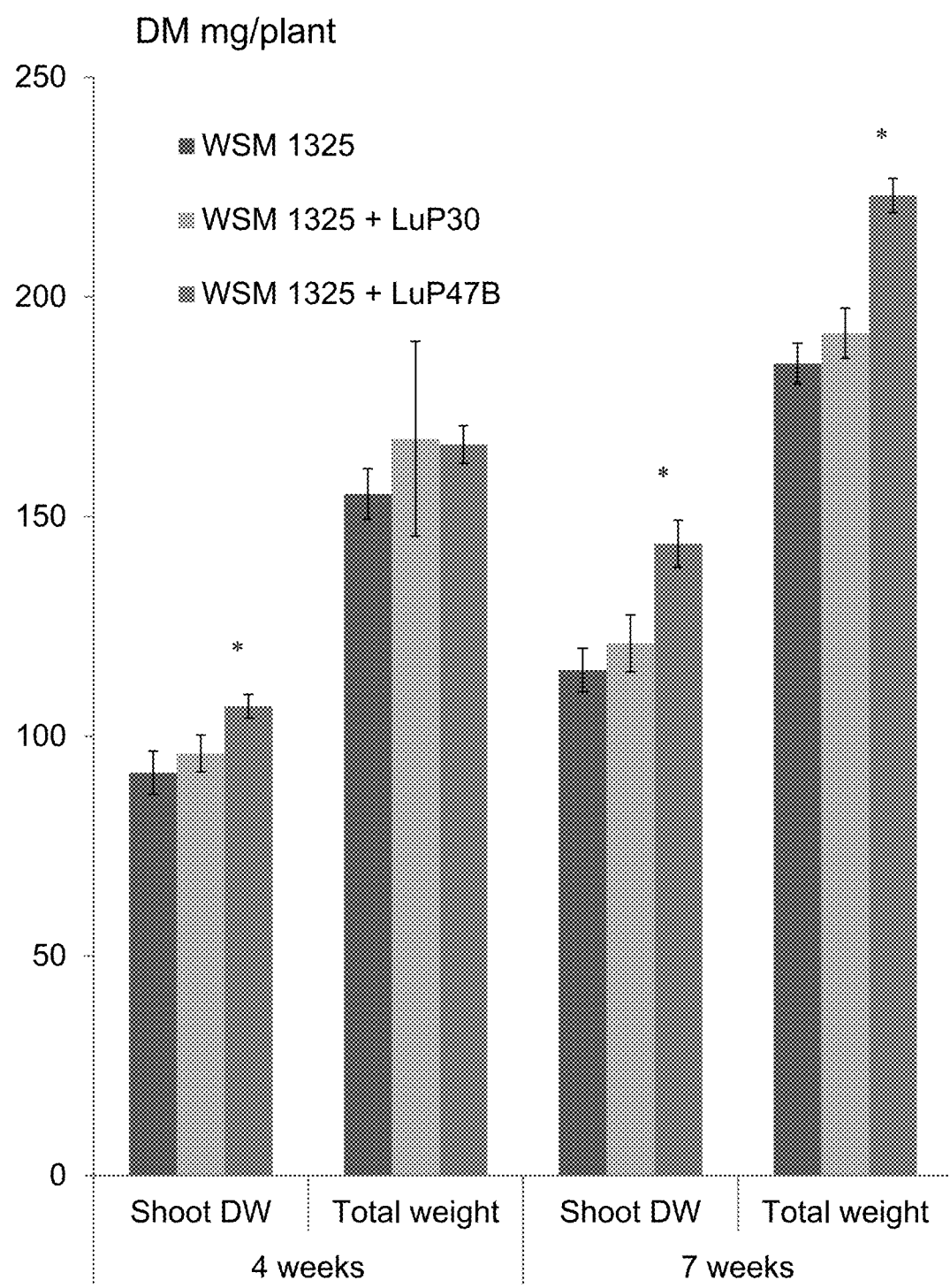

FIG. 11 is a graphical representation showing the effects of LuP30 and LuP47B on growth and nodulation of clover when co-inoculated with *Rhizobium* WSM 1325. Asterisks indicate significant differences at p≤0.05 (*) or p≤0.01 (**).

TABLE 1 shows indole acetic acid production and phosphate solubilising activity of selected endophytic actinobacteria. (+) positive production; (−) no production.

TABLE 2 shows in-vitro interaction assay results between selected endophytic actinobacteria and three different rhizobia at various concentrations. (++) positive effects on growth of the *Rhizobium*; (+) slightly positive effects (0) neutral effect on growth of the *Rhizobium*; (−) slightly negative effects on growth of the *Rhizobium*; (−−) negative effects on growth of the *Rhizobium*.

TABLE 3 shows the effects of six endophytic actinobacteria isolated from healthy wheat roots on the symbiosis of RRI128 and lucerne plants after seven weeks from planting. Seeds were coated with six different actinobacteria in 0.3% xanthan gum one day before planting. Inoculation with the RRI128 strain occurred five days after planting. (n=5 pots, 4 plants per pot).

TABLE 4 shows the effects of endophytic actinobacteria on the symbiosis of rhizobia strain RRI128 and lucerne plants after 45 days from planting. Seeds were coated with six different actinobacteria in 0.3% xanthan gum one day before planting. Inoculation with the RRI128 strain occurred five days after planting. (n=10 pots, 4 plants per pot).

TABLE 5 shows the effects of endophytic actinobacteria, EN23, LuP30 and LuP47B on symbiosis of the rhizobia strain RRI128 and lucerne in terms of nitrogen content and trace elements in lucerne shoots at 45 days old.

TABLE 6 shows the effects of endophytic actinobacteria on symbiosis of RRI128 and lucerne plants after seven weeks from planting in nutrient limited conditions. Seeds were coated with six different actinobacteria in 0.3% xanthan gum one day before planting. Inoculation of the RRI128 strain occurred five days after planting (n=5 tubes, 1 plant per tube).

TABLE 7 shows the effect of actinobacterial and rhizobial coinoculation on *Rhizoctonia* root rot of lucerne plants and growth characteristics of shoot and root dry weights.

TABLE 8 shows 16S rRNA gene sequence identities of selected endophytic actinobacteria using BLASTN on GenBank.

TABLE 9 shows plant responses due to treatment with *Streptomyces* spp. EN23, LuP30 and LuP47B alone or co-inoculation with *S. meliloti* RRI 128 at 7 weeks after planting (n=4). Control[a]: uninoculated plants; Control[b]: plants inoculated only with *S. meliloti* RRI 128; (A)=3 ppm N, (B)=25 ppm N, (C)=50 ppm N; Asterisks indicate significant differences at P<0.05 (*) or P<0.01 (**).

TABLE 10 shows the effect of actinobacteria and soil N on nodule number per lucerne plant at 4 and 7 weeks after inoculated (n=4). Different letters in the same column indicate means are significantly different (P<0.05).

TABLE 11 shows the effects of LuP30 and LuP47B on the number of nodules per Lucerne plant after 3 weeks inoculation with different concentrations of *S. meliloti* RRI 128. (n=4) Means±SE.

TABLE 12 shows lucerne shoot dry weight in response to co-inoculation with LuP30 or LuP47B and *S. meliloti* RRI 128 after 10, 21 and 35 days at 25 ppm N ($^{15}$NH$_4$$^{15}$NO$_3$). Asterisks indicate significant differences at p<0.05.

TABLE 13 shows the accumulation of N ($^{14}$N and $^{15}$N) in the shoot and root of lucerne plants inoculated with rhizobia and actinobacteria (n=4). Different letters in the same column indicate means are significantly different (P<0.05).

TABLE 14 shows the growth and nodulation response of clover to LuP30 and LuP47B after 4 and 7 weeks co-inoculation with *Rhizobium* WSM 1325, (n=4). Different letters in the same column indicate means are significantly different (P<0.05).

TABLE 15 shows the effects of two actinobacteria LuP30 and LuP47B on the growth of two rhizobial strains on agar plates at three concentrations after 7 days. (++) positive effects on rhizobial growth visible as a zone of increased growth around the actinobacterial plug; (+) slightly positive effects, a smaller zone of increased growth around the actinobacterial plug; (0) neutral effect.

TABLE 16 shows the growth and nodulation of soybean (*Glycine max* cv. Djackal) in response to co-inoculation with each of four strains of actinobacteria and *Bradyrhizobium* strain CB 1809, 4 weeks after inoculation.

TABLE 17 shows the effect of actinobacteria on the elemental content of soy shoots (amount per plant).

TABLE 18 shows the effect of endophytic actinobacteria (*Streptomyces* spp. LuP8, LuP3, LuP44 and LuP47B in combination with *Bradyrhizobium* strain CB1809) and 25 mg NH$_4$NO$_3$ per kg soil on soybean growth, nodulation and seeds after 7 weeks inoculation with the rhizobia (n=4). Different letters in the same column indicate means are significantly different (P<0.05). Rhi=*Bradyrhizobium* sp. CB1809.

TABLE 19 shows nodule number, nodule weight, pod number and total plant biomass in pea plants grown in field trials at three sites (Riverton SA, Hart SA and Pimpinio Vic).

EXAMPLE 1—MATERIALS AND METHODS

Isolation and Identification of Endophytic Actinobacteria

Four different legumes including lucerne, pea, clover and medics were collected from different places and picked randomly at various stages of growth around South Australia. Different media used for isolation of endophytic actinobacteria were Humic acid Vitamin B agar (HV; Masayuki and Hideo, *Journal of Fermentation Technology* 65(5): 501-509, 1987), yeast extract-casein hydrolysate agar (YECD), tryptic soy agar (TSA) (Oxoid Limited, UK), tap water yeast extract agar (TWYE), all at pH of 7.2±0.2. Benomyl (DuPont Qualicon, Wilmington, Del. USA) was added to each agar medium at a final concentration of 50 μg·ml$^{-1}$ to control fungal growth.

The plants were washed under running tap water to remove dust and soil attached to the roots and nodules. The roots and nodules were separated from the plants and air-dried overnight at room temperature. The dry roots and nodules were surface sterilized following the method of Coombs and Franco (*Applied and Environmental Microbiology*, Vol. 69: 5603-5608, 2003). The surface sterilization process started by washing with absolute ethanol for 1 minute, followed by 6 minutes in 4% NaOCl, 30 seconds in absolute ethanol and a final wash with autoclaved R.O. water.

Surface sterilized nodules were snipped out from the roots and crushed in 0.9% saline until forming a homogenous mixture. The nodule suspension was spread onto the surface of at least three different isolation media. The sterilized roots were air dried before being cut into approximately 1 cm fragments by a blade or scissors, and placed onto the different media plates. Plates were incubated at 27° C. and 37° C.

The plates were checked regularly at least once per week from the first week until new single colonies could not be found. When colonies appeared, they were transferred to half strength potato dextrose agar (HPDA) for purification. The single colonies were transferred onto three different media such as HPDA, oatmeal agar (ISP3) and mannitol soybean agar (MS) to distinguish them based on their different morphologies, colour and pigments produced (media recipes all per Atlas, *Handbook of Microbiological Media*, 1993).

*Actinobacteria, Sinorhizobium Meliloti* and Lucerne Seeds

Lucerne seeds named 'SARDI Ten' and *Sinorhizobium meliloti* RRI128 (referred to as RRI128), which is a commercial inoculant for lucerne, were supplied by the South Australian Research and Development Institute (SARDI). Seeds chosen for planting were similar in size and weight. Five endophytic actinobacteria (EN2, EN16, EN23, EN27, EN46) which were isolated from healthy wheat root and demonstrated to benefit plant growth of some cereals (see Patent Cooperation Treaty publication WO2005/003328, incorporated herein by reference), together with 148 endophytic actinobacteria isolated from different legumes, were tested both in vitro and in planta.

Effects of Endophytic Actinobacteria on Germination of Lucerne—on Agar

Lucerne seeds were placed in Petri dishes (usually 2-3 times the required amount) and surface sterilized by the following method: 30 seconds in 70% (v/v) ethanol, 2-3 minutes in 3% (v/v) hypochlorite solution, rinsed three times in autoclaved R.O. water, remaining in the third rinse for 10 minutes then left under the laminar flow to dry. Five sterilized seeds were put on a McKnight's solution 1% agar plate with one drop of an isolated actinobacteria suspension (200-2000 cells) applied to each seed while the control seeds received one drop of 0.9% saline. The plates were left under a 14 hour light cycle per day at room temperature (20-30° C.) for 2 weeks. The number of germinated seeds and the length of roots were recorded.

Effects of Endophytic Actinobacteria on Germination of Lucerne—in Sandy Loam

Lucerne seeds were also sterilized as described above and the sandy loam was autoclaved at 121° C. for 15 minutes. Twelve percent moisture sandy loam was made by adding McKnight's solution before adding 300 g of sandy loam with 20 sterilized seeds to a small basket, 10 cm wide and 20 cm length. The seeds were sown with actinobacterial suspension applied on the top before slightly covering with sandy loam. The baskets were kept under a 14 hour light/10 hour dark cycle at room temperature (20-30° C.) for 2 weeks. The number of seeds germinated was recorded, and when germinated, the length of the roots was measured. A total of 148 well-sporulating actinobacteria were tested.

IAA Production

The ability of the endophytic actinobacteria to produce IAA was examined following the method of Khanma et al. (*World Journal of Microbiology and Biotechnology* 25: 649-655, 2009). A 6 mm diameter plug of actinobacteria which was grown on ISP2 for 5-7 days was transferred into 5 ml of yeast malt extract (YME) containing 0.2% L-Tryptophan. The broth was shaken at 125 rpm for 7 days at 27° C. before centrifuging 1 ml of broth at 11,000 rpm for 15 min. The mixture of 0.5 ml supernatant and 1 ml Salkowski reagent (12 g of FeCl$_3$ per litre of 7.9 M H$_2$SO$_4$) was mixed well and kept in the dark for 30 minutes. The IAA production activity was measured using optical density (OD) at 530 nm. YME broth without L-tryptophan was used as the base line and pure IAA (Sigma) with different concentrations were used to make a standard curve.

Phosphate Solubilisation Activity

The phosphate solubilisation ability of selected isolates was detected following the method described by Beneduzi et al. (*Applied Soil Ecology* 39: 311-320, 2008). The actinobacteria isolates were inoculated on glucose yeast (GY) medium that contained 10 g of glucose, 2 g of yeast extract and 1.5% agar in 1 L of distilled water. Two solutions were added to the medium, the first was 5 g of K$_2$HPO$_4$ in 50 ml distilled water and the second solution was 10 g of CaCl$_2$ in 100 ml of distilled water. These two solutions were autoclaved separately and added into the GY medium before pouring into plates. These two solutions changed the colour of the GY medium to white opaque showing the presence of insoluble calcium phosphate. A positive reaction was demonstrated by the presence of a clear zone in the area surrounding the isolates.

Antagonism Tests

Rhizobial strains were grown on yeast mannitol agar (YMA; Graham, *Applied Microbiology* 17(5): 769-770, 1969) plates or slants for 3-5 days before harvesting. The rhizobial strains were harvested and serially diluted in 0.9% saline. The OD at 600 nm of the rhizobial solutions was checked and the number of colony-forming units was counted following the method of Miles and Misra (*Journal Hygiene* 38: 732-749, 1938). At the same time 100 µl of these serial dilutions at different OD values were spread onto YMA plates and allowed to dry. Two plugs about 25 mm² of each actinobacterial strain grown on International *Streptomyces* Project 2 (ISP2; Atlas, *Handbook of Microbiological Media*, 1993) medium for 7 days were placed on the surface of the inoculated YMA plates. The plates were incubated for 5-7 days at 27° C. and checked daily for antagonistic activity against the rhizobia. Rhizobia and the actinobacteria that were grown separately as pure cultures on YMA plates were used as negative controls. Streptomycin, vancomycin and were used as positive antibacterial controls. All treatments were replicated twice and incubated at 27° C.

Interaction Between Endophytic Actinobacteria and *Rhizobium* on Lucerne

Lucerne seeds were surface-sterilized as described above and sown in autoclaved pots. Each pot contained about 1 kg of sand and vermiculite mixture, and had two separate parts to allow easy drainage. Five and 148 endophytic actinobacteria isolated from surface-sterilized healthy wheat roots and surface-sterilized healthy root and nodules of four different legumes such as lucerne, pea, clover and medics, respectively, were coated on the surface of the lucerne seeds in a 0.3% (w/v) sterile xanthan gum solution. 100 ml of MQ water was added to each pot before planting the ten coated seeds. The top of the pot was covered with a thin layer of granulated plastic beads. Then, 200 mL of 1/80 McKnight's solution containing starter nitrogen (266 mg $NH_4NO$ per 20 L McKnight's solution) was gently added to each pot before covering with freezer bags and placing in the glasshouse. The number of seedlings was thinned down to four plants before adding 1 ml of *Rhizobium* RRI128 around $10^8$ CFU/ml at five days from planting. Every week 50 ml of nitrogen solution (1.2 $g \cdot L^{-1}$ of $NH_4NO_3$) was applied to each pot for nitrogen-treated plants and MQ water was added as required.

All treatments were replicated ten times completely randomized in the glasshouse, with the position of the pots changed randomly every week. The plants were harvested after the sixth to seventh week from sowing. The parameters examined were height and dry weight of the shoot, length and dry weight of the root, the number and dry weight of nodules per plant. Nodules were removed, counted and dried at 60° C. Dry weight of each nodule was calculated by dividing total nodule weight by total nodule number of two plants with five replicates.

SPAD 502 Readings, Total Nitrogen Analysis and $N_2$ Fixed in the Shoots

During the sixth week, leaves of lucerne plants were measured by a SPAD 502 meter (Chlorophyll meter SPAD-502, Konica Minolta) designed to indicate the amount of chlorophyll present in plant leaves. The three biggest leaves were checked to get SPAD readings. Moreover, dry leaves of control plants (only treated with *Sinorhizobium*), and plants treated with *Rhizobium* and EN23 and EN27, LuP30 and LuP47B harvested in the seventh week were analysed for the content of nitrogen and other elements. The leaves were dried at 60° C. for 48 h to obtain constant weight and were ground to about 1 mm in size for analysis.

$N_2$ fixation associated with the shoots was calculated by the following equation:

$$N_2 \text{ fixed in the shoots} = (\% \, N^*SDW)_{treatment} - (\% \, N^*SDW)_{uninoculated}$$

Nutrient Limitation Experiment

Lucerne seeds were surface sterilized and coated with actinobacteria as described above. Two coated seeds were sown in a 50 ml centrifuge tube containing 65 g of autoclaved washed sand and 10 ml of McKnight's starter N (0.133 mg) added five times less than compared with normal 0.665 mg per plant in pot assays. This was then covered by sand and plastic beads. The number of seedlings was thinned down to one seedling before inoculating with $10^8$ $CFU \cdot ml^{-1}$ RRI128 suspension. The tubes were kept inside the growth chamber with a 12 h light and 12 h dark cycle. Water was supplied as required until 7 weeks.

DNA Extraction

In a sterile 1.5 ml eppendorf tube 10 µl of lysozyme was added to 500 µl of Tris-EDTA (TE) pH 7.4, before re-suspending 2-3 loops of actinobacterial cells into the mixture, which was then vortexed and spun later. The eppendorf tube was incubated at 37° C. for 60 minutes before adding 10 µl of proteinase K and 32.5 µl of 10% SDS and incubated at 55° C. for 60 minutes. Next, 100 µl of 5M NaCl and 65 µl of CTAB/NaCl were added and the mixture was incubated at 55° C. for 10 minutes. Six hundred microlitres of phenolchloroform was added and the tube was left at room temperature for 30 minutes with intermittent shaking every 10 minutes. After centrifuging at 12,000 rpm for 15 minutes, the supernatant was transferred to a new sterile 1.5 ml eppendorf tube. An additional 500 µl of chloroform was added to the tube and left at room temperature for 15 minutes with mixing by inversion every 7-8 minutes before centrifuging at 12,000 rpm for 15 minutes. The aqueous phase was transferred into a new sterile 1.5 ml eppendorf tube before adding 20 µl of 10 $mg \cdot ml^{-1}$ RNAse and incubating at 37° C. for 60 minutes. Then 500 µl of chloroform was added and the tube left at room temperature for 15 minutes. After centrifuging at 12,000 rpm for 15 minutes, the supernatant was transferred to a new sterile 1.5 ml eppendorf tube. An additional 500 µl of chloroform was added and the tube left at room temperature for 15 minutes (with mixing by inversion every 7-8 minutes). After centrifuging at 12,000 rpm for 15 minutes, the supernatant was transferred to a new sterile 1.5 ml eppendorf tube (steps repeated). A 0.1×volume of 3M Na Acetate (50 µl) and 3×volume of 100% ethanol (1 ml) was added to the tube before leaving at −20° C. overnight. The supernatant was removed carefully so as not to disrupt the pellet after centrifuging at the maximum speed 16,000 rpm for 15 minutes. The pellet was washed twice with 70% ethanol and dried by placing tubes in a heating block at 55° C. with the lids open for approximately 10 minutes. Finally, the pellet was re-suspended in 50 µl of sterile water.

PCR of 16S rRNA Gene

A master mixture was prepared as 1 µl of dNTPs (10 mM), 1 µl of DNA Taq polymerase (5 U/µl), 5 µl of ThermoPol buffer, 2 µl of 27f primer (AGAGTTTGATCCTGGCTCAG; SEQ ID NO: 1), 2 µl of 1465r primer (TACG-GYTACCTTGTTACGACTT; SEQ ID NO: 2), 2 µl of DNA sample and 37 µl of injection water. PCR was performed by heating the PCR tubes at 94° C. for 2 minutes, followed by 40 cycles of 94° C. for one minute, 52° C. for one minute and 72° C. for two minutes, and 72° C. for 10 minutes. A 1.2% agarose gel containing 3 µl of GelRed (Biotium) in 40 ml agarose was used to separate the molecular weight of the PCR products. One microlitre of loading dye was mixed well with 2 µl of each PCR product before loading the gel, which was run in a running buffer 0.5×TBE at 70 V and 400 mA for 60 minutes. The products of PCR were sequenced by Macrogen, Korea. The resultant 16S rRNA sequences were compared to the GenBank database by using the National Centre for Biotechnology Information database (NCBI) BLASTN program, including the results of the highest matches for each isolate and the corresponding bit score and percentage identity.

EXAMPLE 2—ISOLATION AND IDENTIFICATION OF ENDOPHYTIC ACTINOBACTERIA 225 endophytic actinobacteria were isolated from roots and nodules of pea, lucerne, clover and medic. 73 were from nodules and 152 were from roots. Based on their morphology, 126 cultures (56%) belong to the genus *Streptomyces*, 54 (24%) belong to *Microbispora*, 20 (8.89%) belong to *Micromonospora* and 25 cultures are as yet unidentified. Humid acid vitamin B agar (HV), yeast extract casein dextrose (YECD) and tap water yeast extract (TWYE) media successfully allowed growth of almost all of the isolates mentioned. 125 cultures were isolated from HV medium, 72 cultures were from TWYE, 26 were from YECD and one of them was isolated from TSA. There was not much difference in the number of cultures isolated at 37° C. and 27° C., which were 125 and 112 cultures, respectively. Eighty five cultures were isolated from roots of lucerne, while 65 isolates were from pea (42 from roots and 23 from nodules), 37 cultures were from clover (16 from roots and 26 from nodules) and 35 were from medics (12 from roots and 23 from nodules). Thirty two out of the 73 isolates from nodules were *Streptomyces*, 17 were *Microbispora*, 5 were *Micromonospora* and 19 were unidentified.

EXAMPLE 3—EFFECTS OF ENDOPHYTIC ACTINOBACTERIA ON GERMINATION OF LUCERNE, IAA PRODUCTION AND PHOSPHATE SOLUBILISATION

Fifty six of 148 cultures (38%) isolated from lucerne promoted germination of lucerne seeds and 27 (18%) isolates negatively affected germination of lucerne seeds in terms of number of seeds germinated and length of roots on agar plates. In addition, 39 of 148 cultures improved germination of lucerne seeds with the presence of *Rhizobium* on sandy loam.

Figure 1:
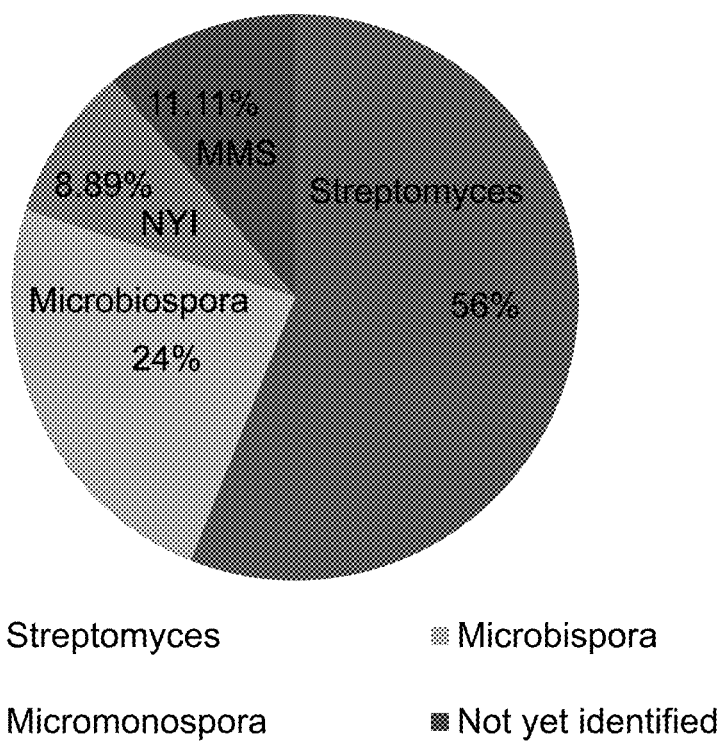
FIG. 1 shows the cultivable actinobacterial endoflora isolated from roots and nodules of different legumes— including pea, lucerne, clover and medics.
Figure 2:
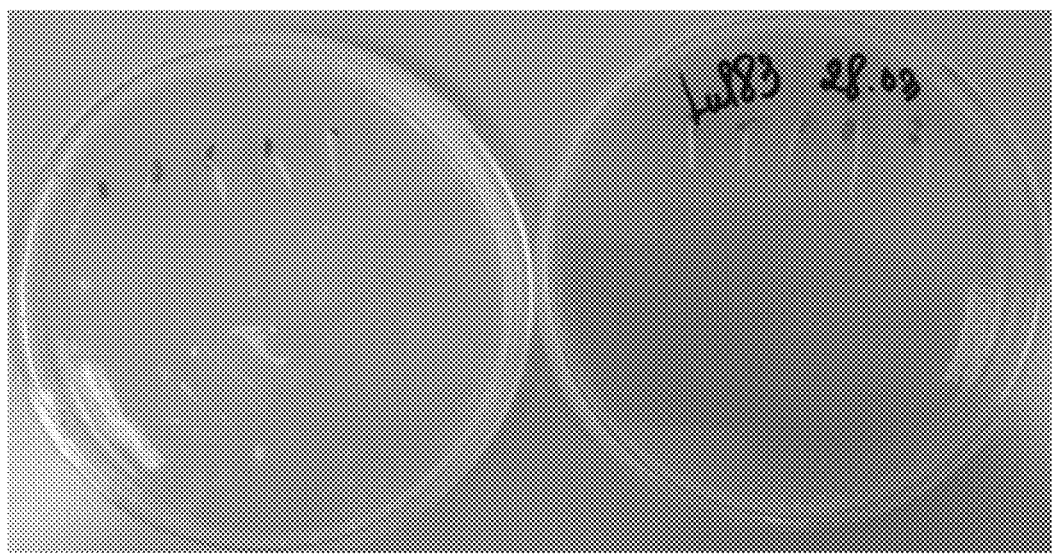
FIG. 2 shows the beneficial effects of endophytic actinobacteria on germination of lucerne seeds on agar plates after 36 hours incubation. The plate on the left shows surface-sterilised seeds with 0.85% saline; the plant on the right shows surface-sterilised seeds coated with a spore suspension of LuP83 in 0.85% saline.
Figure 3:
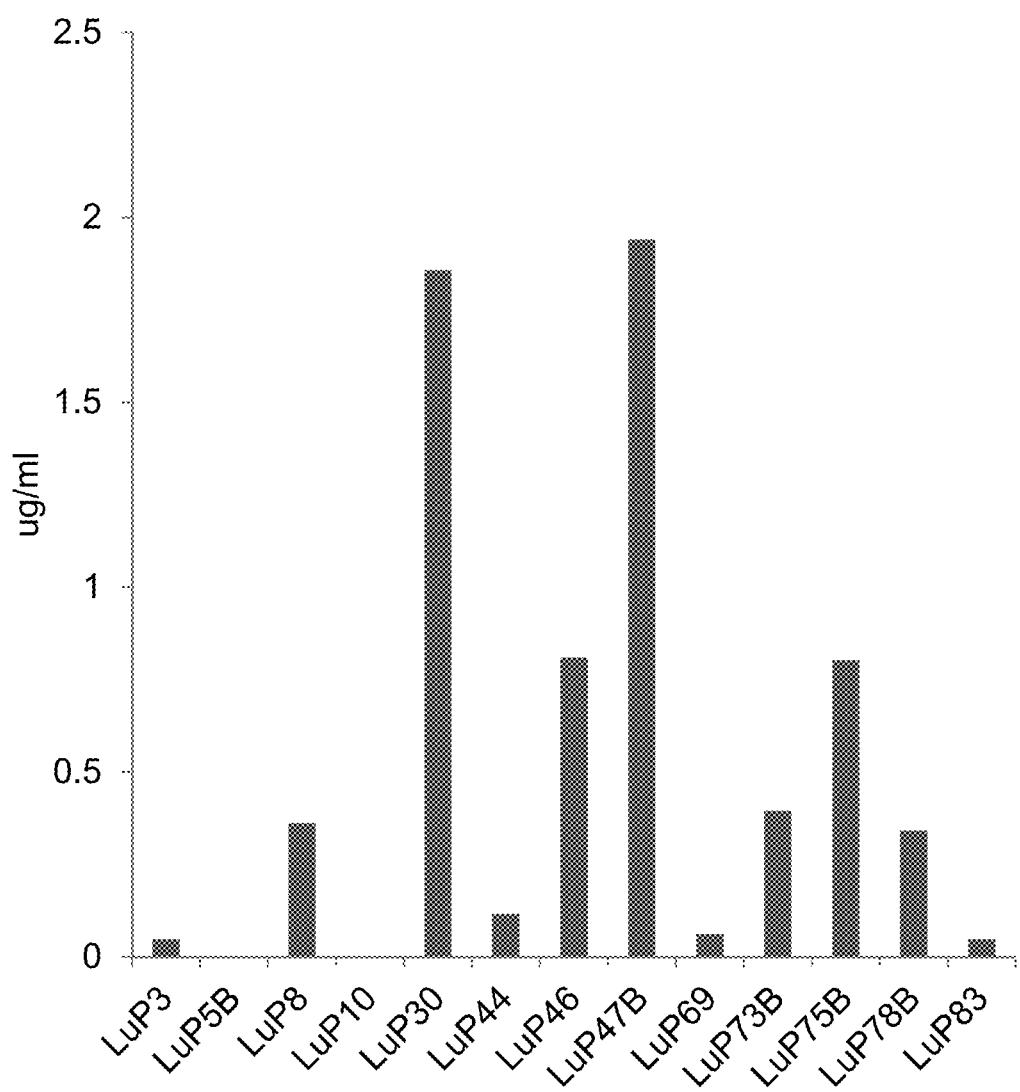
FIG. 3 shows indole acetic acid production by selected endophytic actinobacteria.

As shown in Table 1 and FIG. 3, a range of endophytic actinobacteria showed the ability to produce IAA. Table 1 also identifies cultures that were found to have phosphate solubilisation ability. They were LuP5B, LuP44 and LuP8A.

EXAMPLE 4—ANTAGONISM TESTING

Two concentrations of rhizobia were tested for antagonism with 14 endophytic actinobacteria; five non-legume-isolated and nine legume-isolated cultures. As shown in Table 2, most of the endophytic actinobacteria had neutral or positive effects on growth of three rhizobia RRI128, SRDI736, WSM1115G, except for LuP10, EN28 and EN46. LuP10 increased growth of the RRI128 but inhibited growth of SRDI736 and WSM1115G, whereas LuP3, LuP30 and LuP47B increased growth of the three rhizobia at the various concentrations.

As shown in FIG. 4, LuP30 and LuP47B showed significant rhizobial growth stimulation *Rhizobium leguminosarum* bv. *trifolii* strain WSM 1325 and *Bradyrhizobium lupini* strain WSM 471.

EXAMPLE 5—EFFECTS OF SIX ENDOPHYTIC ACTINOBACTERIA ISOLATED FROM NON-LEGUMES

As shown in Table 3, some endophytic actinobacteria isolated from wheat roots showed beneficial interactions with the RRI128-inoculated lucerne plants while some were neutral, with no significant impacts on different parameters. EN2 significantly increased the fresh and dry weight of the shoot as well as the length of the root, while EN23 increased not only height, fresh and dry weight of the shoot but also length and fresh weight of the root. In particular, the average height of the shoot plants receiving combined treatment of RRI128 and EN23 was 15.2 cm, whilst plants treated with RRI128 only was 12.55 cm. EN23 increased the shoot height of the plant by 21.1%. Moreover, EN23 significantly increased the dry weight of each nodule, the total dry weight of nodules, nitrogen content of the plant as well as total nitrogen per plant, though it did not significantly increase the number of nodules per plant. Total mass per plant treated with EN23 increased by 25.7% compared with plants treated with the *Rhizobium* only control.

Treatment with EN27 resulted in slight increases in height, fresh and dry weight of the shoot, and fresh and dry weight of the root. Although EN27 significantly reduced the number of nodules, the fresh weight of each nodule and the total dry weight of nodules per plant were higher than that of RRI128 only plants. Furthermore, EN27 also significantly increased the SPAD readings, nitrogen content (% $N_2$) and total nitrogen per plant. EN23 and EN27 increased the amount of $N_2$ fixed in the shoots, by 0.85 and 0.80 mg per plant, respectively, compared with the RRI128 only plants (Table 3). In contrast, EN16 significantly reduced the number of nodules and total dry weight of nodules per plant after seven weeks from planting. EN28 and EN46 had no significant effect on the growth of lucerne plants with the RRI128. Nitrogen content was 2.725% of mass for the control, 3.225% of mass for EN23-treated and 3.65% for EN27-treated plants. There was 1.38 mg of total N per control plant, while EN23 and EN27-treated plants had 2.23 mg and 2.18 mg total N, respectively.

EXAMPLE 6—EFFECTS OF ENDOPHYTIC ACTINOBACTERIA ISOLATED FROM LEGUMES

The interactions between *Rhizobium* RRI128 and 148 cultures isolated from legumes were screened in terms of plant growth and nitrogen fixation. LuP47B and LuP30 showed beneficial effects on the symbiosis of *Rhizobium* and lucerne, with increased height of shoot, mass of shoot and plant and nitrogen fixation per plant. As shown in Table 4, treatment with these cultures led to an increase of 35.33% and 24.87% of shoot dry weight and 29.91% and 25.87% of total mass per plant, respectively. LuP47B also increased the height of the shoot significantly, up to 26.25%. Although LuP30 did not significantly promote the height of the shoot, it developed a longer root compared with plants treated with RRI128 only. In contrast, LuP10 increased the root biomass instead of root length.

As shown in Table 5, the combination of *Rhizobium* RRI128 and EN23 significantly increased copper, phosphorous, sodium and nitrogen content in the shoot compared with the RRI128 alone. LuP30 and LuP47B treatment resulted in a significant increase all of the trace elements tested, except iron with the presence of the RRI128. Although the shoot dry weight of plants inoculated with the RRI128 and LuP30 was less than that of plants treated with RRI128 and LuP47B they showed higher amounts of copper, iron and zinc compared with LuP47B. EN23, LuP30 and LuP47B also increased nitrogen content in the shoot, with 0.35, 0.61 and 0.83 mg per each shoot, respectively (see FIG. 6).

EXAMPLE 7—EFFECTS OF ENDOPHYTIC ACTINOBACTERIA ON SYMBIOSIS OF RHIZOBIA AND LUCERNE WITH LIMITATION OF NUTRIENT SUPPLY

As shown in Table 6 and FIG. 7, in limited nutrient conditions LuP5B significantly increased all growth parameters, such as height of shoot, length of root, shoot and root dry weight, except for number of nodules. LuP47B treatment resulted in increased length of root and shoot dry weight but LuP30 did not increase other parameters of plant growth. Although LuP12A increased root dry weight, it did not promote root length. In contrast, LuP3 increased the length of root but it did not increase the root dry weight (Table 6).

EXAMPLE 8—BIOCONTROL ACTIVITY IN PLANTA

Fifty milliliter centrifugal tubes were used to screen for the biocontrol ability of actinobacterial strains against the fungal root pathogen *Rhizoctonia*. Forty five grams of autoclaved sandy loam were used at a 12% moisture content added as McKnight's starter nitrogen (266 mg of $NH_4NO_3$) solution. Two millet seeds infected with *R. solani* AG8 strain W19 were added at the top of the sandy loam, and a further 10 g of soil containing 12% moisture was added to cover the millet seeds. Two tubes without adding the infested millet seeds with the pathogen and without endophytic actinobacteria were as used as controls. The tubes were placed in a rack covered with aluminium foil and placed in a chamber for two weeks at 15° C. in the absence of light.

Lucerne seeds were surface-sterilized and pre-germinated with actinobacterial suspensions on autoclaved moist filter paper in petri dishes. When the roots were about 1-3 mm length they were dipped in 5 ml (to cover all the seeds) of the rhizobial suspension (approximately $10^8$ cfu/ml) for 3 minutes. Two pre-germinated and coated seeds were transferred into each 50 ml tube and covered with 5 g of soil (12% moisture) and a layer of plastic beads. The tubes were kept at 15° C. in a growth chamber for 3 weeks. There were two replicates of each treatment, and MQ water was added as required. The number of seedlings that emerged, the length of root and root damage were recorded.

Results of the biocontrol assay are shown in Table 7.

EXAMPLE 9—IDENTIFICATION OF ACTINOBACTERIA USING 16S RRNA GENE SEQUENCING

LuP3, LuP12A, LuP30, LuP47B, EN23, EN27, LuP8 and LuP44 were putatively identified as *Streptomyces* sp. by 16S rRNA gene sequencing.

The determined 16S rRNA gene sequences for each organism were as follows:

| Isolate | 16S rRNA gene sequence (5'-3') | Sequence Identifier |
|---|---|---|
| LuP3 | GTGGATTAGTGGCGAACGGGTGAGTAACACGTGGGCAA TCTGCCCTTCACTCTGGGACAAGCCCTGGAAACGGGGTC TAATACCGGATAATACTTTCTCCCTCCTGGGAGAAGGTT GAAAGCTCCGGCGGTGAAGGATGAGCCCGCGGCCTATC AGCTAGTTGGTGGGGTAATGGCCTACCAAGGCGACGAC GGGTAGCCGGCCTGAGAGGGCGACCGGCCACACTGGGA CTGAGACACGGCCCAGACTCCTACGGGAGGCAGCAGTG GGGAATATTGCACAATGGGCGAAAGCCTGATGCAGCGA CGCCGCGTGAGGGATGACGGCCTTCGGGTTGTAAACCT CTTTCAGCAGGGAAGAAGCGAAAGTGACGGTACCTGCA GAAGAAGCGCCGGCTAACTACGTGCCAGCAGCCGCGGT AATACGTAGGGCGCAAGCGTTGTCCGGAATTATTGGGC GTAAAGAGCTCGTAGGCGGCTTGTCACGTCGGTTGTGA AAGCCCGGGGCTTAACCCCGGGTCTGCAGTCGATACGG GCAGGCTAGAGTGTGGTAGGGGAGATCGGAATTCCTGG TGTAGCGGTGAAATGCGCAGATATCAGGAGGAACACCG GTGGCGAAGGCGGATCTCTGGGCCATTACTGACGCTGA GGAGCGAAAGCGTGGGGAGCGAACAGGATTAGATACC CTGGTAGTCCACGCCGTAAACGTTGGGAACTAAGGTGT TGGCGACATTCCACGTCGTCGGTGCCGCAGCTAACGCAT TAAGTTCCCGCCTGGGGAGTACGGCCGCAAGGCTAAA CTCAAAGGAATTGACGGGGGCCCGCACAAGCAGCGGAG CATGTGGCTTAATTCGACGCAACGCGAAGAACCTTACC AAGGCTTGACATACACCGGAAAGCATCAGAGATGGTGC CCCCCTTGTGGTCGGTGTACAGGTGGTGCATGGCTGTCG TCAGCTCGTGTCGTGAGATGTTGGGTTAAGTCCCGCAAC | SEQ ID NO: 3 |

| Isolate | 16S rRNA gene sequence (5'-3') | Sequence Identifier |
|---|---|---|
| | GAGCGCAACCCTTGTTCTGTGTTGCCAGCATGCCCTTCG GGGTGATGGGGACTCACAGGAGACTGCCGGGGTCAACT CGGAGGAAGGTGGGGACGACGTCAAGTCATCATGCCCC TTATGTCTTGGGCTGCACACGTGCTACAATGGCCGGTAC AATGAGCTGCGATGCCGCGAGGCGGAGCGAATCTCAAA AAGCCGGTCTCAGTTCGGATTGGGGTCTGCAACTCGACC CCATGAAGTCGGAGTTGCTAGTAATCGCAGATCAGCAT TGCTGCGGTGAATACGTTCCCGGGCCTTGTACACACCGC CCGTCACGTCACGAAAGTCGGTAACACCCGAAGCCG | |
| LuP12A | GATGAACCACTTCGGTGGGGATTAGTGGCGAACGGGTG AGTAACACGTGGGCAATCTGCCCTTCACTCTGGGACAA GCCCTGGAAACGGGGTCTAATACCGGATACCACTACCG CAGGCATCTGTGGTGGTTGAAAGCTCCGGCGGTGAAGG ATGAGCCCGCGGCCTATCAAGGTTGTTGGTGAGGTAAT GGCTCACCAAGGCGACGACGGGTAGCCGGCCTGAGAGG GCGACCGGCCACACTGGGACTGAGACACGGCCCAGACT CCTACGGGAGGCAGCAGTGGGGAATATTGCACAATGGG CGAAAGCCTGATGCAGCGACGCCGCGTGAGGGATGACG GCCTTCGGGTTGTAAACCTCTTTCAGCAGGGAAGAAGC GAAAGTGACGGTACCTGCAGAAGAAGCGCCGGCTAACT ACGTGCCAGCAGCCGCGGTAATACGTAGGGCGCAAGCG TTGTCCGGAATTATTGGGCGTAAAGAGCTCGTAGGCGG CTTGTCACGTCGGGTGTGAAAGCCCGGGGCTTAACCCC GGGTCTGCATTCGATACGGGCTAGCTAGAGTGTGGTAG GGGAGATCGGAATTCCTGGTGTAGCGGTGAAATGCGCA GATATCAGGAGGAACACCGGTGGCGAAGGCGGATCTCT GGGCCATTACTGACGCTGAGGAGCGAAAGCGTGGGGAG CGAACAGGATTAGATACCCTGGTAGTCCACGCCGTAAA CGGTGGGAACTAGGTGTTGGCGACATTCCACGTCGTCG GTGCCGCAGCTAACGCATTAAGTTCCCCGCCTGGGGAG TACGGCCGCAAGGCTAAAACTCAAAGGAATTGACGGGG GCCCGCACAAGCAGCGGAGCATGTGGCTTAATTCGACG CAACGCGAAGAACCTTACCAAGGCTTGACATACGCCGG AAAGCATCAGAGACGGTGCCCCCCTTGTGGTCGGTGTA CAGGTGGTGCATGGCTGTCGTCAGCTCGTGTCGTGAGAT GTTGGGTTAAGTCCCGCAACGAGCGCAACCCTTGTCCTG TGTTGCCAGCATGCCCTTCGGGGTGATGGGACTCACA GGAGACCGCCGGGGTCAACTCGGAGGAAGGTGGGGAC GACGTCAAGTCATCATGCCCCTTATGTCTTGGGCTGCAC ACGTGCTACAATGGCAGGTACAATGAGCTGCGATACCG TGAGGTGGAGCGAATCTCAAAAAGCCTGTCTCAGTTCG GATTGGGGTCTGCAACTCGACCCCATGAAGTCGGAGTT GCTAGTAATCGCAGATCAGCATTGCTGCGGTGAATACG TTCCCGGGCCTTGTACACACCGCCCGTCACGTCACGAAA GTCGGTAACACCCGAAGCCGGTGGCCTCAACCC | SEQ ID NO: 4 |
| LuP30 | CAGTCGAACGATGAACACTTCGGTGGGGATTAGTGGCG AACGGGTGAGTAACACGTGGGCAATCTGCCCTTCACTCT GGGACAAGCCCTGGAAACGGGGTCTAATACCGGATAAC ACTTCCACTCGCATGGGTGGAGGTTAAAAGCTCCGGCG GTGAAGGATGAGCCCGCGGCCTATCAGCTTGTTGGTGA GGTAATGGCTCACCAAGGCGACGACGGGTAGCCGGCCT GAGAGGGCGACCGGCCACACTGGGACTGAGACACGGCC CAGACTCCTACGGGAGGCAGCAGTGGGGAATATTGCAC AATGGGCGAAAGCCTGATGCAGCGACGCCGCGTGAGGG ATGACGGCCTTCGGGTTGTAAACCTCTTTCAGCAGGGAA GAAGCGAAAGTGACGGTACCTGCAGAAGAAGCGCCGG CTAACTACGTGCCAGCAGCCGCGGTAATACGTAGGGCG CAAGCGTTGTCCGGAATTATTGGGCGTAAAGAGCTCGT AGGCGGTCTGTCGCGTCGGATGTGAAAGCCCGGGGCTT AACCCCGGGTCTGCATTCGATACGGGCAGACTAGAGTG TGGTAGGGGAGATCGGAATTCCTGGTGTAGCGGTGAAA TGCGCAGATATCAGGAGGAACACCGGTGGCGAAGGCGG ATCTCTGGGCCATTACTGACGCTGAGGAGCGAAAGCGT GGGGAGCGAACAGGATTAGATACCCTGGTAGTCCACGC CGTAAACGGTGGGAACTAGGTGTTGGCGACATTCCACG TCGTCGGTGCCGCAGCTAACGCATTAAGTTCCCCGCCTG GGGAGTACGGCCGCAAGGCTAAAACTCAAAGGAATTGA CGGGGGCCCGCACAAGCAGCGGAGCATGTGGCTTAATT CGACGCAACGCGAAGAACCTTACCAAGGCTTGACATAC ACCGGAAACGGCCAGAGATGGTCGCCCCCTTGTGGTCG GTGTACAGGTGGTGCATGGCTGTCGTCAGCTCGTGTCGT GAGATGTTGGGTTAAGTCCCGCAACGAGCGCAACCCTT GTTCTGTGTTGCCAGCATGCCCTTCGGGGTGATGGGAC TCACAGGAGACTGCCGGGGTCAACTCGGAGGAAGGTGG | SEQ ID NO: 5 |

| Isolate | 16S rRNA gene sequence (5'-3') | Sequence Identifier |
|---|---|---|
| | GGACGACGTCAAGTCATCATGCCCCTTATGTCTTGGGCT GCACACGTGCTACAATGGCCGGTACAAAGAGCTGCGAA GCCGTGAGGTGGAGCGAATCTCAAAAAGCCGGTCTCAG TTCGGATTGGGGTCTGCAACTCGACCCCATGAAGTCGG AGTTGCTAGTAATCGCAGATCAGCATTGCTGCGGTGAAT ACGTTCCCGGGCCTTGTACACACCGCCCGTCACGTCACG AAAGTCGGTAACACCCGAAGCCGGTGGCCCAACC | |
| LuP47B | GTGAGGTAATGGCTCACCAAGGCGACGACGGGTAGCCG GCCTGAGAGGGCGACCGGCCACACTGGGACTGAGACAC GGCCCAGACTCCTACGGGAGGCAGCAGTGGGGAATATT GCACAATGGGCGAAAGCCTGATGCAGCGACGCCGCGTG AGGGATGACGGCCTTCGGGTTGTAAACCTCTTTCAGCAG GAAGAAGCGAAAGTGACGGTACCTGCAGAAGAAGCG CCGGCTAACTACGTGCCAGCAGCCGCGGTAATACGTAG GGCGCAAGCGTTGTCCGGAATTATTGGGCGTAAAGAGC TCGTAGGCGGCTTGTCACGTCGGGTGTGAAAGCCCGGG GCTTAACCCCGGGTCTGCATTCGATACGGGCTAGCTAGA GTGTGGTAAGGGAGATCGGAATTCCTGGTGTAGCGGTG AAATGCGCAGATATCAGGAGGAACACCGGTGGCGAAG GCGGATCTCTGGGCCATTACTGACGCTGAGGAGCGAAA GCGTGGGGAGCGAACAGGATTAGATACCCTGGTAGTCC ACGCCGTAAACGGTGGGAACTAAGGTGTTGGCGACATT CCACGTCGTCGGTGCCGCAGCTAACGCATTAAGTTCCCG CCCGGGGGAGTACGGCCGCAAGGCTAAAACTCAAAGGA ATTGACGGGGGCCCGCACAAGCAGCGGAGCATG | SEQ ID NO: 6 |
| EN23 | ACGAACGCTGGCGGCGTGCTTAACACATGCAAGTCGAA CGATGAAGCCGCTTCGGTGGTGGATTAGTGGCGAACGG GTGAGTAACACGTGGGCAATCTGCCCTTCACTCTGGGAC AAGCCCTGGAAACGGGGTCTAATACCGGATAACACTCT GTCCCGCATGGGACGGGGTTGAAAGCTCCGGCGGTGAA GGATGAGCCCGCGGCCTATCAGCTTGTTGGTGGGGTAA TGGCCTACCAAGGCGACGACGGGTAGCCGGCCTGAGAG GGCGACCGGCCACACTGGGACTGAGACACGGCCCAGAC TCCTACGGGAGGCAGCAGTGGGGAATATTGCACAATGG GCGAAAGCCTGATGCAGCGACGCCGCGTGAGGGATGAC GGCCTTCGGGTTGTAAACCTCTTTCAGCAGGGAAGAAG CGAAAGTGACGGTACCTGCAGAAGAAGCGCCGGCTAAC TACGTGCCAGCAGCCGCGGTAATACGTAGGGCGCAAGC GTTGTCCGGAATTATTGGGCGTAAAGAGCTCGTAGGCG GCTTGTCACGTCGGATGTGAAAGCCCGGGGCTTAACCC CGGGTCTGCATTCGATACGGGCTAgCTAGAGTGTGGTAG GGGAGATCGGAATTCCTGGTGTAgCGGTGAAATGCGCA GATATCAGGAGGAACACCGGTGGCGAAGGCGGATCTCT GGGCCATTACTGACgTcTGAGGAGCGAAAGCGTGGGgAg CGAACAGGATTAGATACCCTGgTAGTCCACGCCGTAAAC GTTGGgAACTAGgTGTTGGCGACATTCCACGTCGTCGGT GCCGCAGCTAACGCATTAAGTTCCCGCCTGGGGAGTA CGGCCGCAAGGCTAAAACTCAAAGGAATTGACGGGGGC CCGCACAAGCAGCGGAGCATGTGGCTTAATTCGACGCA ACGCGAAGAACCTTACCAAGGCTTGACATATACCGGAA AGCATCAGAGATGGTGCCCCCCTTGTGGTCGGTATACA GGTGGTGCATGGCTGTCGTCAGCTCGTGTCGTGAGATGT TGGGTTAAGTCCCGCAACGAGCGCAACCCTTGTTCTGTG TTGCCAGCATGCCCTTCGGGGTGATGGGACTCACAGG AGACTGCCGGGGTCAACTCGGAGGAAGGTGGGGACGAC GTCAAGTCATCATGCCCCTTATGTCTTGGGCTGCACACG TGCTACAATGGCCGGTACAATGAGCTGCGATGCCGCGA GGCGGAGCGAATCTCAAAAAGCCGGTCTCAGTTCGGAT TGGGGTCTGCAACTCGACCCCATGAAGTCGGAGTTGCT AGTAATCGCAGATCAGCATTGCTGCGGTGAATACGTTCC CGGGCCTTGTACACACCGCCCGTCACGTCACGAAAGTC GGTAACACCCGAAGCCGGTGGCCCAACCCTTGTGGGAG GGAGCTGTCGAAGGTGGGACTGGCGATTG | SEQ ID NO: 7 |
| EN27 | TTAANACATGCAANTCGAACGATGAACCCNGTTTCGGT GGTGGATTAGTGGCGAACGGTGAGTAANANGTGGGCAA TTTGCCCTTCATTTTGGACAAGCCCTGGAAACGGGTTTA ATACCGGATAACATTTTNTCCCGCATGGGANGGGGTTG AAAGNTCCGGCGGTGAAGGATGAGCCCGCGGCCTATNA GCTTGTTGGTGGGGTAATGGCCTACCCAAGGGAGACGG GTAGCCGGCCTGAGAGGGCGACCGGCCACACTGGGAAT GAGANACGCCCAGAATCCTACGGGAGGCAGCAGTGG GGAATATTGCACAATGGGCGAAAGCCTGATGCAGCGAN GCCGCGTGAGGGATGACGGCCTTNGGGTTGTAAACCTT | SEQ ID NO: 8 |

| Isolate | 16S rRNA gene sequence (5'-3') | Sequence Identifier |
|---|---|---|
| | TTTNAGCAGGGAAGAAGCGAAAGTGACGGTACCTGCAG<br>AAGAAGCGCCGGCTAAATAAGTGCCAGCAGCCGCGGTA<br>ATAAGTAGGGCGCAAGCGTTGTCCGGAATTATTGGGCG<br>TAAAGAGCTTGTAGGCGGCTTGTCANGTNGGATGTGAA<br>AGCCCGGGGNTTAACCCCGGGTTTGCATTTGATACGGG<br>CTAGNTAGAGTGTGGTAGGGGAGATNGGAATTCCTGGT<br>GTAGCGGTGAAATGCGCAGATATCAGGAGGAACACCGG<br>TGGCGAAGGCGGATCTCTGGGCCATTACTGACGCTGAG<br>GAGCGAAAGCGTGGGGAGCGAACAGGATTAGATACCCT<br>GGTAGTCCACGCCGTAAACGTTGGGAACTAGGTGTTGG<br>CGACATTCCACGTCGTCGGTGCCGCAGCTAACGCATTAA<br>GTTCCCCGNCTGGGGAGTACGGCCGCAAGGCTAANACT<br>CAAAGGAATTGACGGGGGCCCGNACAAGCAGCGGANC<br>ATGTGGCTTAATTCGACGCANCGCGAAGAACCTTACCA<br>AGGCTTGACATATACCGGAAAGCATCAGAGATGGTGCC<br>CCCCTTGTGGTCGNTATACANGTGGTGCATGNCTGTCGT<br>CACCTCGTGTCGTGAGATGTTGGGTTAAGTCCCGCAACG<br>AGCGCNACCCTTGNTCTGTGTTGNCANCATGCCCTTCGG<br>GGNTGATGGGGACTCACAGGANACTGNCCGGGGTCAAC<br>TCCGGANGAAGGTGGGTGACGAAGTCAAGGTCATCATG<br>NCCCCTTATGTCTTGGTGCTGCACACGTGC | |
| LuP8 | AATGGGCTAAGTTCGAAACGATTGAACCACTTTCGGTG<br>GGGATTAGTGGCGAACGGGTGAGTAACACGTGGGCAAT<br>CTGCCCTTCACTCTGGGACAAGCCCTGGAAACGGGGTCT<br>AATACCGGATACCACTACCGCAGGCATCTGTGGTGGTT<br>GAAAGCTCCGGCGGTGAAGGATGAGCCCGCGGCCTATC<br>AGCTTGTTGGTGAGGTAATGGCTCACCAAGGCGACGAC<br>GGGTAGCCGGCCTGAGAGGGCGACCGGCCACACTGGGA<br>CTGAGACACGGCCCAGACTCCTACGGGAGGCAGCAGTG<br>GGGAATATTGCACAATGGGCGAAAGCCTGATGCAGCGA<br>CGCCGCGTGAGGGATGACGGCCTTCGGGTTGTAAACCT<br>CTTTCAGCAGGGAAGAAGCGAAAGTGACGGTACCTGCA<br>GAAGAAGCGCCGGCTAACTACGTGCCAGCAGCCGCGGT<br>AATACGTAGGGCGCAAGCGTTGTCCGGAATTATTGGGC<br>GTAAAGAGCTCGTAGGCGGCTTGTCACGTCGGGTGTGA<br>AAGCCCGGGGCTTAACCCCGGGTCTGCATTCGATACGG<br>GCTAGCTAGAGTGTGGTAGGGGAGATCGGAATTCCTGG<br>TGTAGCGGTGAAATGCGCAGATATCAGGAGGAACACCG<br>GTGGCGAAGGCGGATCTCTGGGCCATTACTGACGCTGA<br>GGAGCGAAAGCGGGGGGGGCAAAAAAGGGAACCCGGC<br>CGGGGGGGG | SEQ ID NO: 9 |
| LuP44 | TCGGTGGGGATTAGTGGCGAACGGGTGAGTAACACGTG<br>GGCAATCTGCCCTTCACTCTGGGACAAGCCCTGGAAAC<br>GGGGTCTAATACCGGATACCACTACCGCAGGCATCTGT<br>GGTGGTTGAAAGCTCCGGCGGTGAAGGATGAGCCCGCG<br>GCCTATCAGCTTGTTGGTGAGGTAATGGCTCACCAAGGC<br>GACGACGGGTAGCCGGCCTGAGAGGGCGACCGGCCACA<br>CTGGGACTGAGACACGGCCCAGACTCCTACGGGAGGCA<br>GCAGTGGGGAATATTGCACAATGGGCGAAAGCCTGATG<br>CAGCGACGCCGCGTGAGGGATGACGGCCTTCGGGTTGT<br>AAACCTCTTTCAGCAGGGAAGAAGCGAAAGTGACGGTA<br>CCTGCAGAAGAAGCGCCGGCTAACTACGTGCCAGCAGC<br>CGCGGTAATACGTAGGGCGCAAGCGTTGTCCGGAATTA<br>TTGGGCGTAAAGAGCTCGTAGGCGGCTTGTCACGTCGG<br>GTGTGAAAGCCCGGGGCTTAACCCCGGGTCTGCATTCG<br>ATACGGGCTAGCTAGAGTGTGGTAGGGGAGATCGGAAT<br>TCCTGGTGTAGCGGTGAAATGCGCAGATATCAGGAGGA<br>ACACCGGTGGCGAAGGCGGATCTCTGGGCCATTACTGA<br>CGCTGAGGAGCGAAAGCGTGGGGAGCGAACAGGATTA<br>GATACCCTGGTAGTCCACGCCGTAAACGGTGGGAACTA<br>GGTGTTGGCGACATTCCACGTCGTCGGTGCCGCAGCTAA<br>CGCATTAAGTTCCCCGCCTGGGGAGTACGGCCGCAAGG<br>CTAAAACTCAAAGGAATTGACGGGGGCCCGCACAAGCA<br>GCGGAGCATGTGGCTTAATTCGACGCAACGCGAAGAAC<br>CTTACCAAGGCTTGACATACGCCGGAAAGCATCGGAGA<br>CGGGGTCCCCCTTGTGGTCGGTGTACAGGTGGTGCATGG<br>CTGTCGTCAGCTCGTGTCGTGAGATGTTGGGTTAAGTCC<br>CGCAACGAGCGCAACCCTTGTCCTGTGTTGCCAGCATGC<br>CCTTCGGGGTGATGGGGACTCACAGGAGACCGCCGGGG<br>TCAACTCGGAGGAAGGTGGGGACGACGTCAAGTCATCA<br>TGCCCCTTATGTCTTGGGCTGCACACGTGCTACAATGGC<br>AGGTACAATGAGCTGCGATACCGTGAGGTGGAGCGAAT<br>CTCAAAAAGCCTGTCTCAGTTCGGATTGGGGTCTGCAAC<br>TCGACCCCATGAAGTCGGAGTTGCTAGTAATCGCAGAT | SEQ ID NO: 10 |

-continued

| Isolate | 16S rRNA gene sequence (5'-3') | Sequence Identifier |
|---|---|---|
| | CAGCATTGCTGCGGTGAATACGTTCCCGGGCCTTGTACA CACCGCCCGTCACGTCACGAAAGTCGGTAACACCCGAA GCCGGTGGCCCAACCC | |

As shown in Table 8, the closest match for LuP3 was *Streptomyces drozdowiczii* with up to 99.4% 16S rRNA gene sequence identity. The closest match for LuP30 was *Streptomyces rishiriensis*, which showed up to 99.9% 16S rRNA gene identity. LuP12A, LuP47B, LuP8 and LuP44 are all very close to both *Streptomyces ciscaucasicus* and *Streptomyces canus*, with >99% 16S rRNA gene sequence identity.

EXAMPLE 10—EFFECT OF ACTINOBACTERIA/RHIZOBIA CO-INOCULATION ON GROWTH PARAMETERS OF LUCERNE AT DIFFERING N CONCENTRATIONS

The effects of three actinobacteria on the growth and symbiosis of lucerne and rhizobia was studied at three levels of $NH_4NO_3$ 3 ppm, 25 ppm and 50 ppm.

The factorial experiment comprised (i) 3 strains of actinobacteria, (ii) ± inoculation with *Sinorhizobium meliloti* RRI 128 and (iii) 3 levels of soil $NH_4NO_3$. The pots were prepared and watered with a nitrogen deficient McKnight's solution supplemented with $NH_4NO_3$ to provide soil nitrogen of 3, 25 and 50 ppm. Plant seeds designated to rhizobia treatments were inoculated with a suspension (1 ml per plant containing $10^8$ CFU) of rhizobia 6 days after sowing. Each treatment was replicated eight times. Pots were arranged in a completely randomised design in a greenhouse and plants four pots of each treatment were harvested at 4 and 7 weeks after inoculation with the *S. meliloti* RRI 128.

As shown in Table 9, co-inoculation of each of EN23, LuP30 and LuP47B with *S. meliloti* RRI 128 was able to statistically significantly improve at least one of root dry weight or shoot dry weight over the un-inoculated or *Rhizobium* only controls at at least one concentration of N.

As shown in Table 10, co-inoculation of each of EN23, LuP30 and LuP47B with *S. meliloti* RRI 128 was able to statistically significantly improve the number of nodules over the un-inoculated or *Rhizobium* only controls at at least one concentration of N at the 4 week and/or 7 week sampling time.

Regarding nutrient levels, in the absence of the *S. meliloti* RRI 128 EN23, LuP30 or LuP47B reduced significantly iron and copper in shoot plants after 7 weeks at both 25 mg and 50 mg/kg$_{nitrogen}$ $NH_4NO_3$ supply while sodium and molybdenum was increased. Total nitrogen in shoot plants were increased significantly with seeds coated with LuP47B at 50 mg N while EN23 and LuP30 did increase total amount of nitrogen shoot plant but not significant. The actinobacteria showed the best impact on the nutrient in shoot of lucerne at 25 mg N after 4 weeks inoculation with *S. meliloti* RRI 128 EN23. Three actinobacteria treatment plants had higher the content of iron, manganese, boron, copper, molybdenum, zinc, and macro elements such as calcium, potassium, phosphate and nitrogen.

EXAMPLE 11—EFFECT OF ACTINOBACTERIA/RHIZOBIA CO-INOCULATION ON GROWTH PARAMETERS OF LUCERNE AT DIFFERING DOSING OF RHIZOBIA INOCULATION

Increasing *S. meliloti* RRI 128 dose concentrations resulted in slight increases number of nodules and of the growth of the plant. The number of nodules per plant increased from 4.3 to 7.0 and 8.8 nodules when the concentration of rhizobia was increased from $5\times10^2$ to $5\times10^4$ and $5\times10^6$ respectively (see Table 11). The significant effects of LuP30 and LuP47B on plant growth and nodulation of lucerne plants were on $5\times10^2$ CFU·$ml^{-1}$ of *S. meliloti* RRI 128 (See FIG. 8). The shoot dry weight and total mass per plant were increased up to about 50% to 60% and was similar with plants treated with the rhizobia at $10^4$ and $10^6$ CFU·$ml^{-1}$ (see FIG. 8A). In addition, co-inoculation with either LuP30 or LuP47B individually with *S. meliloti* RRI 128 at $5\times10^2$ CFU·$ml^{-1}$ increased the number of nodules up to 7 and 9 per plant, respectively while control plants had 4.3 nodules per plant.

EXAMPLE 12—$^{15}$N EXPERIMENT

*Streptomyces* spp. LuP30 and LuP47B were added as spores to lucerne seed with a sterile 0.3% xanthan gum solution and air dried before sowing. Seeds were treated with *S. meliloti* RRI 128. The planting process was as described in EXAMPLE 10.

The nitrogen supplied was $^{15}NH_4^{15}NO_3$ (98%) with initial N concentration in soil (25 mg/kg $^{15}NH_4^{15}NO_3$). Plants were harvested after 10, 21 and 35 days after inoculation with the *S. meliloti* RRI 128. Nitrogen in shoot and root materials was analysed by mass spectrometry to determine the proportions of plant N derived from the atmosphere and soil.

The plants were harvested at three times—at 10, 21 and 35 days after inoculation with *S. meliloti* RRI 128. The effectiveness of LuP30 and LuP47B was re-confirmed by the increase of the shoot dry weight and the number of nodules after 21 and 35 days co-inoculation with *S. meliloti* RRI 128 (FIG. 9) and (Table 12). The amount of $^{15}$N and $^{14}$N in plants was estimated by spectrometry and the total N in whole plant co-inoculation with LuP30 or LuP47B was increased up to 40% and 60% respectively compared with plants treated *S. meliloti* RRI 128 alone (FIG. 10). This was mostly due to greater accumulation of $^{14}$N (derived from $N_2$-fixation) which was increased by LuP30 or LuP47B by 47% and 72%, respectively. The actinobacteria significantly increased the amount of $^{14}$N in their plants while LuP47B also increased the amount of $^{15}$N in their shoot and root (Table 13).

EXAMPLE 13—EFFECT OF ACTINOBACTERIA ON GROWTH AND SYMBIOSIS OF CLOVER

Clover cultivar Campeda (*Trifolium subterraneum* L.), was chosen to examine the effects of the two actinobacteria LuP30 and LuP47B which have shown an increase in growth and nitrogen fixation of lucerne in previous experiments. Rhizobial strain *Rhizobium* WSM 1325 was inoculated on seeds of clover.

The factorial experiment comprised (i) two strains of actinobacteria (LuP30 and LuP47B), (ii) inoculation with rhizobia strain WSM1325 for clover. Growth of rhizobia and actinobacteria, plant growth media and nutrition, sowing and water supply were as described above. The concentration of $NH_4NO_3$ was supplied at 25 mg per kg of sand and vermiculite where the actinobacteria LuP30 and LuP47B showed increased plant growth and nitrogen fixation for lucerne plants. Eight replicates for each treatment with four pots each harvested at 4 and 7 weeks after inoculation with rhizobia.

Co-inoculation of LuP30 with WSM 1325 increased the number of nodules after 7 weeks and nodule mass after 4 and 7 weeks in clover (Table 14). Actinobacteria strain LuP47B co-inoculated with *Rhizobium* WSM 1325 significantly increased the dry weight of shoot, total mass and number of nodules per plant after 4 and 7 weeks inoculation with the *Rhizobium* while the nodule mass per plant was only increased after 7 weeks (see FIG. 11 and Table 14). There was a significant change in the dry wt. of root of plants between the two harvests; for example, LuP30 increased root dry weight after 4 weeks while LuP47B increased root dry weight after 7 weeks.

EXAMPLE 14—IN VITRO INTERACTION OF RHIZOBIA AND ACTINOBACTERIA

The interaction between LuP30 or LuP47B on the growth of two rhizobia *Rhizobium* WSM 1325 and *Bradyrhizobium* WSM 471 was studied at three concentrations $10^4$, $10^6$ and $10^8$ $CFU \cdot ml^{-1}$ (or $10^3$, $10^5$ and $10^7$ cells on each agar plate) of the two rhizobial strains. The two actinobacteria LuP30 and LuP47B were grown on ISP2 for 7-10 days and agar plugs of the well grown cultures were placed onto the agar plates containing the three rates of rhizobia. The growth of the rhizobia was examined 5 to 14 days after adding the actinobacteria plugs.

LuP30 and LuP47B showed positive and non-antagonistic effects on the growth of both rhizobia (*Rhizobium* WSM 1325 and *Bradyrhizobium* WSM 471). At low concentrations of rhizobia, less than $10^7$ $CFU \cdot ml^{-1}$ or $10^5$ $CFU \cdot ml^{-1}$ on each agar plate, LuP30 and LuP47B promoted a visible increase in the growth of both rhizobia on YMA medium after 5 days incubation at 27° C. (Table 15). When the concentration of the rhizobia was more than $10^7$ $CFU \cdot ml^{-1}$ the effects of two actinobacteria LuP30 and LuP47B were not obvious on the growth of the two rhizobia as analysed by visual observation, as was observed with the low rhizobial concentrations. These results show that rhizobial strains obtain growth benefits and are not inhibited by the two actinobacteria LuP30 and LuP47B.

EXAMPLE 15—EFFECT OF ACTINOBACTERIA ON GROWTH AND SYMBIOSIS OF SOYBEAN PLANTS (*GLYCINE MAX*)

The overall aim of this experiment was to evaluate a range of endophytic actinobacterial strains on the growth of soybean plants to determine whether these strains have a broad leguminous plant host range. The results of the study of plants harvested 4 weeks after the addition of the *Bradyrhizbium* inoculum to the actinobacterial-treated plants showed that 4 of the 18 strains tested had significantly improved plant growth and/or nitrogen content of the soybean plants.

Materials and Methods

Soybean seeds (*Glycine max* cv. Djackal) were surface-sterilised and coated with spores of actinobacteria suspended in 0.3% (w/v) xanthan gum. Coated seeds (1 per pot) were sown into a pasteurised potting mix ~1 kg (50:50 by volume of sand:vermiculite) contained in 1.25 L pots. 200 ml of nitrogen deficient McKnight's nutrient solution was applied at sowing and supplemented to provide 25 mg of $NH_4NO_3$ per kg of potting media. Pots were arranged in a randomised block design with 5 replicates of each treatment. Plants were harvested at 4 weeks and 7 weeks after inoculation with *Bradyrhizobium* strain CB 1809.

Treatments were nil control, rhizobia with no actinobacteria, and *Rhizobium* plus each of the following *Streptomyces* strains: Str. EN23, Str. EN27, Str. LuP3, Str. LuP5, LuP8, Str. LuP10, Str. LuP12A, Str. LuP30, Str. LuP44, Str. LuP46B, Str. LuP47B, Str. LuP73B, Str. LuP75, Str. PG3, Str. PG4, Str. PP1, Str. PP9, CM23.

Parameters measured were:
Length, dry weight of shoot and root.
Number and total mass of nodules per plant.
Nitrogen, P and trace elements in the plant shoots.

Effectiveness of *Bradyrhizobium* CB 1809 on Nodulation and Plant Growth of Soybean Inoculation with *Bradyrhizobium* CB 1809 in the absence of actinobacteria resulted in abundant nodulation (around 120 nodules per plant) and increased shoot and root dry weights confirming the effectiveness of the *Bradyrhizobium* strain with the cultivar Djackal. There were no obvious constraints to nodulation, in the testing system.

Effect of Actinobacteria on Plant Growth and Symbiosis of Soy Plants at 4 Weeks Post Inoculation Data for four (isolated from lucerne root) of the 18 actinobacteria tested are presented, based on their positive effects. Thirteen of the strains did not affect any of the parameters measured. As shown in Table 16, plants treated with Str. LuP8 and *Bradyrhizobium* CB 1809 strain showed increases in plant growth compared to plants only inoculated with CB1809. Str. LuP47B increased dry weight of shoots and total plant weight (+15%) and LuP30 increased total plant weight (+12%). Str. LuP30, LuP44 and LuP47B also improved the nodule mass per plant by 20, 22 and 29% respectively.

As shown in Table 17, plants treated with LuP47B also had increased levels of iron, magnesium, phosphorus and nitrogen (27%) compared with plants inoculated with *Bradyrhizobium* CB1809 only. LuP8 increased total N (23%) and also iron. LuP30 increased iron content.

Effect of Actinobacteria on Plant Growth and Symbiosis of Soy Plants at 7 Weeks Post Inoculation As shown in Table 18, statistically significant results were:
LuP47B increased height of shoots by 38%;
LuP8 increased total nodule mass by 54%;

LuP8 increased fresh weight of pods by 24% and number of seeds per plant by 35%; and LuP47B increased the dry weight of seeds by 43% while LuP8 increased total dry weight of shoot and pods per plant by 24%.

EXAMPLE 16—EFFECT OF ACTINOBACTERIA ON GROWTH AND SYMBIOSIS OF FIELD PEA (*PISUM* SP.)

Pea field trials were sown Hart (28 May) and Riverton (10 June) in South Australia (SA), and at Pimpinio (15 May) in Victoria. The trials were arranged in randomised complete block design with 3 replicates, each comprising an uninoculated control and 3 inoculation treatments. Treatments were applied to Kaspa field pea which was sown to achieve a seedling density of 50 plants/m². The rhizobia treatment (*Rhizobium leguminosarum* bv. *viciae* strain WSM1455) was applied at approximately 100 fold the rate recommended commercially. The co-inoculation treatment comprised the rhizobia treatment co-inoculated with *Streptomyces* sp. strain Lup47B, which was applied as spores to the seed before sowing.

Six plants were sampled from each plot at approximately 8 weeks after sowing and nodule number and nodule dry weight per plant determined. An additional ten plant shoots were sampled from each plot in October/November (late pod fill) and used to estimate shoot biomass, pod number per plant and to estimate the % N derived from fixation using the $^{15}$N natural abundance method. Plots were machine harvested to estimate grain yield and subsamples used for the determination of grain protein (Total N Leco, CSBP).

Table 19 shows nodule number, nodule weight, pod number and total plant biomass in pea plants grown in field trials at three sites (Riverton SA, Hart SA and Pimpinio Vic). A summary of the results shown in table 19 is:

A significant effect on nodulation was seen at Pimpinio, where the actinobacteria (LuP47B)/*Rhizobium* coinoculation significantly increased the number of nodules relative to the *Rhizobium* only control; and Actinobacteria (LuP47B)/*Rhizobium* coinoculation increased biomass at all sites relative to *Rhizobium* only inoculation, with two sites and the mean of all sites achieving statistically significant increases in biomass.

Those skilled in the art will appreciate that the invention described herein is susceptible to variations and modifications other than those specifically described. It is to be understood that the invention includes all such variations and modifications. The invention also includes all of the steps, features, compositions and compounds referred to, or indicated in this specification, individually or collectively, and any and all combinations of any two or more of the steps or features.

Also, it must be noted that, as used herein, the singular forms "a", "an" and "the" include plural aspects unless the context already dictates otherwise. Thus, for example, reference to "a microorganism" includes a single microorganism as well as two or more microorganisms; "a leguminous plant" includes a single plant as well as two or more plants; and so forth.

Reference to any prior art in this specification is not, and should not be taken as, an acknowledgment or any form of suggestion that this prior art forms part of the common general knowledge in any country.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Reference is made to standard textbooks of molecular biology that contain methods for carrying out basic techniques encompassed by the present invention, including DNA restriction and ligation for the generation of the various genetic constructs described herein. See, for example, Maniatis et al, *Molecular Cloning: A Laboratory Manual* (Cold Spring Harbor Laboratory Press, New York, 1982) and Sambrook et al. (2000, supra).

TABLE 1

| Cultures | IAA production | Phosphate solubilisation |
|---|---|---|
| LuP3 | + | − |
| LuP5B | − | ++ |
| LuP8 | + | + |
| LuP10 | − | − |
| LuP12A | + | − |
| LuP30 | ++ | − |
| LuP44 | + | + |
| LuP46(2) | + | − |
| LuP47B | ++ | − |
| LuP73B | + | − |
| LuP83 | + | − |

TABLE 2

| | $OD_{600\,nm}$ <= 0.06 <= 6 × 10$^7$ cfu/ml | | | $OD_{600\,nm}$ <= 0.1 <= 1 × 10$^8$ cfu/ml | | |
|---|---|---|---|---|---|---|
| Cultures | RRI128 | SRDI736 | WSM1115G | RRI128 | SRDI736 | WSM1115G |
| EN16 | 0 | 0 | 0 | 0 | 0 | 0 |
| EN23 | 0 | 0 | ++ | 0 | 0 | + |
| EN27 | 0 | 0 | 0 | 0 | 0 | 0 |
| EN28 | 0 | 0 | − | 0 | 0 | − |
| EN46 | − | 0 | 0 | 0 | 0 | 0 |
| Lu P3 | ++ | + | + | ++ | + | + |
| LuP8 | 0 | 0 | + | 0 | 0 | ++ |
| LuP10 | ++ | −− | − | + | −− | − |
| LuP12 A | 0 | 0 | 0 | 0 | 0 | ++ |
| LuP30 | ++ | ++ | ++ | ++ | + | ++ |
| LuP44 | 0 | + | + | 0 | 0 | + |
| LuP46(2) | 0 | + | 0 | 0 | 0 | + |
| LuP47B | + | + | + | 0 | 0 | ++ |
| LuP83 | 0 | 0 | ++ | 0 | 0 | + |

TABLE 3

| Lucerne treatment | Height of shoot (cm) | Shoot dry weight (mg) | Length of root (cm) | Root dry weight (mg) |
|---|---|---|---|---|
| Untreated* | 9.21$^a$ | 30.23$^a$ | 24.64$^{bc}$ | 13.55$^{ab}$ |
| RR1128 only | 12.55$^b$ | 50.63$^b$ | 23.57$^{ab}$ | 17.49$^{ab}$ |
| RRI128 + EN2 | 13.94$^{bcd}$ | 64.17$^{cd}$ | 30.13$^d$ | 20.30$^b$ |
| RRI128 + EN16 | 12.75$^b$ | 52.55$^b$ | 18.44$^a$ | 12.44$^a$ |
| RRI128 + EN23 | 15.20$^d$ | 69.15$^d$ | 28.66$^{cd}$ | 16.48$^{ab}$ |
| RRI128 + EN27 | 14.82$^{cd}$ | 59.71$^{bcd}$ | 20.79$^{ab}$ | 20.87$^b$ |
| RRI128 + EN28 | 13.06$^{bc}$ | 55.45$^{bc}$ | 19.63$^{ab}$ | 17.38$^{ab}$ |
| RRI128 + EN46 | 13.48$^{bcd}$ | 58.30$^{bc}$ | 22.00$^{ab}$ | 16.00$^{ab}$ |

| | Nodule fresh weight (mg) | No. of nodules | SPAD 502 reading | N content (%) | N per plant (mg) |
|---|---|---|---|---|---|
| Untreated* | 0$^a$ | 0$^a$ | ND | ND | ND |
| RR1128 only | 0.58$^b$ | 22.22$^{cd}$ | 28.31$^a$ | 2.725$^{a**}$ | 1.38 |
| RRI128 + EN2 | 1.02$^{cd}$ | 23.55$^{cd}$ | 29.64$^{ab}$ | ND | ND |
| RRI128 + EN16 | 0.86$^{bc}$ | 17.42$^b$ | 29.62$^{ab}$ | ND | ND |
| RRI128 + EN23 | 1.27$^d$ | 25.74$^d$ | 31.46$^{bc}$ | 3.225$^{b**}$ | 2.23 |
| RRI128 + EN27 | 0.78$^{bc}$ | 16.85$^b$ | 31.83$^c$ | 3.65$^{c**}$ | 2.18 |
| RRI128 + EN28 | 0.74$^{bc}$ | 21.55$^{bcd}$ | 28.91$^a$ | ND | ND |
| RRI128+ EN46 | 0.91$^{bc}$ | 19.70$^{bc}$ | 28.95$^a$ | ND | ND |

Untreated*: seeds were coated with 0.3% xanthan gum without rhizobium. The different letters in the same column indicate a significant difference ($p < 0.05$). Data was analyzed using one-way ANOVA and Duncan test.

TABLE 4

| Treatment | Height of shoot (cm) | Length of root (cm) | Shoot dry weight (mg) | Root dry weight (mg) | Total Mass (mg) | No of nodules | DW of nodule (mg) | Total nodule mass (mg) |
|---|---|---|---|---|---|---|---|---|
| Untreated* | 4.85$^a$ | 18.00$^a$ | 11.75$^a$ | 15.25$^a$ | 27$^a$ | 0$^a$ | 0$^a$ | 0$^a$ |
| RR1128 only | 12.19$^b$ | 18.77$^{ab}$ | 78.4$^b$ | 35.6$^b$ | 114$^b$ | 22.10$^b$ | 0.1081$^b$ | 2.280$^b$ |
| RRI128 + EN23 | 13.33$^{bc}$ | 23.80$^{ab}$ | 89.73$^{bc}$ | 43.56$^b$ | 132.29$^{bc}$ | 21.90$^b$ | 0.1238$^{bc}$ | 2.711$^{bc}$ |
| RRI128 + EN27 | 12.21$^{bc}$ | 27.56$^{bc}$ | 80.76$^{bc}$ | 47.78$^{bc}$ | 127.54$^{bc}$ | 19.89$^b$ | 0.1054$^b$ | 2.0964$^b$ |
| RRI128 + Lu P3 | 12.96$^{bc}$c | 20.47$^{ab}$ | 83.27$^{bc}$ | 44.2$^b$ | 127.47$^{bc}$ | 22.50$^b$ | 0.1061$^b$ | 2.390$^b$ |
| RRI128 + LuP5B | 11.17$^{bc}$ | 23.45$^{ab}$ | 74.59$^b$ | 42.78$^b$ | 117.37$^b$ | 16.70$^b$ | 0.1356$^{bc}$ | 2.264$^b$ |
| RRI128 + LuP10 | 14.22$^{bc}$ | 21.30$^{ab}$ | 80.93$^{bc}$ | 58.89$^c$ | 139.82$^{bc}$ | 18.22$^b$ | 0.1261$^{bc}$ | 2.297$^b$ |
| RRI128 + LuP12A | 13.95$^{bc}$ | 22.33$^{ab}$ | 81.9$^{bc}$ | 40.3$^b$ | 122.20$^b$ | 18.30$^b$ | 0.1072$^b$ | 1.962$^b$ |
| RRI128 + Lu P30 | 13.83$^{bc}$ | 32.55$^c$ | 97.9$^{cd}$ | 45.6$^{bc}$ | 143.50$^c$ | 20.80$^b$ | 0.0985$^b$ | 2.0610$^b$ |
| RRI128 + LuP44 | 12.91$^{bc}$ | 21.57$^{ab}$ | 83.7$^{bc}$ | 49.2$^{bc}$ | 132.90$^{bc}$ | 20.50$^b$ | 0.1070$^b$ | 2.1935$^b$ |
| RRI128 + LuP47B | 15.39$^c$ | 25.92$^{bc}$ | 106.1$^d$ | 42.00$^b$ | 148.10$^c$ | 20.50$^b$ | 0.1615$^c$ | 3.380$^c$ |

Untreated*: seeds were coated with 0.3% xanthan gum without rhizobium. The different letters in the same column indicate a significant difference ($p < 0.05$). Data was analyzed using one-way ANOVA and Duncan test.

TABLE 5

| Treatment | RRI128 only | RRI128 + EN23 | RRI128 + LuP30 | RRI128 + LuP47B |
|---|---|---|---|---|
| Boron (mg) | 3.759a | 3.932a | 4.621b | 4.631b |
| Calcium (µg) | 0.839a | 0.933ab | 1.002b | 1.181c |
| Copper (µg) | 0.602a | 0.745b | 0.860c | 0.738b |
| Iron (µg) | 23.66a | 21.13a | 24.38a | 21.90a |
| Magnesium (mg) | 0.732a | 0.784a | 0.904b | 0.983b |
| Manganese (µg) | 12.54a | 12.89a | 14.82b | 15.18b |
| Phosphorus (mg) | 0.086a | 0.111b | 0.120c | 0.121c |
| Sodium (mg) | 0.102a | 0.144bc | 0.137b | 0.173c |
| Sulfur (mg) | 0.191a | 0.212ab | 0.228bc | 0.244c |
| Nitrogen (mg) | 2.598a | 2.949b | 3.205c | 3.431d |
| Zinc (µg) | 18.48a | 18.96ab | 22.75c | 21.58bc |

The different letters in the same column indicate a significant difference ($p < 0.05$). Data was analyzed using one-way ANOVA and Duncan test.

TABLE 6

| Treatment | Height of shoot | Length of root | Shoot dry weight | Root dry weight | Total Mass | No of nodules |
|---|---|---|---|---|---|---|
| Untreated* | 3$^a$ | 15.25$^b$ | 6.9$^a$ | 7.9$^e$ | 14.8$^a$ | 0$^a$ |
| RRI128 only | 3.6$^{abc}$ | 11.83$^a$ | 17.33$^{bc}$ | 12.67$^{ab}$ | 30.00$^b$ | 6.33$^{bcd}$ |
| RRI128 + LuP3 | 3.96$^{bc}$ | 15.8b$^c$ | 19.4$^{bc}$ | 17.2b$^{cd}$ | 36.6$^{bcd}$ | 7$^{bcd}$ |
| RRI128 + LuP5B | 4.34$^c$ | 18.7$^c$ | 20.4$^c$ | 18.8$^{cde}$ | 39.2$^{cd}$ | 8.2$^{bcd}$ |
| RRI128 + LuP12A | 4.18$^{bc}$ | 13.62$^{ab}$ | 18.2$^{bc}$ | 22$^e$ | 40.2$^d$ | 8$^{bcd}$ |
| RRI128 + LuP30 | 3.56$^{ab}$ | 13.32$^{ab}$ | 15.4$^b$ | 15.6$^{bc}$ | 31$^{bc}$ | 9.8$^{de}$ |
| RRI128 + LuP47B | 3.74$^{abc}$ | 16.16$^{bc}$ | 20$^c$ | 16.2$^{bcd}$ | 38.2$^{bcd}$ | 10$^{de}$ |

Untreated*: seeds were coated with 0.3% xanthan gum without rhizobium. The different letters in the same column indicate a significant difference ($p < 0.05$). Data was analyzed using one way ANOVA and Duncan test.

TABLE 7

| | Height of shoot (cm) | Shoot dry weight (mg per plant) | Root dry weight (mg per plant) | Total biomass (mg per plant) |
|---|---|---|---|---|
| Control 1 | 3.74 a | 10.01 a | 11.19 ab | 21.20 a |
| Control 2 | 2.2 d | 2.67 d | 4.27 e | 6.74 e |

TABLE 7-continued

|  | Height of shoot (cm) | Shoot dry weight (mg per plant) | Root dry weight (mg per plant) | Total biomass (mg per plant) |
|---|---|---|---|---|
| Control 3 | 2.95 c | 6.6 c | 4.9 de | 11.50 de |
| R + EN16 | 3.07c | 6.82 bc | 7.31 cde | 14.13 cd |
| R + LuP10 | 3.59 ab | 8.09 bc | 7.75 cde | 15.84 c |
| R + LuP12A | 3.12 bc | 7.67 bc | 6.45 cde | 14.12 cd |
| R + LuP30 | 2.95 c | 7.3 bc | 8.52 bcd | 15.82 c |
| R + LuP44 | 2.97 c | 6.85 bc | 9.34 bc | 16.19 bc |
| R + Lu P46(2) | 3.37 abc | 8.51 ab | 7.78 cde | 16.29 bc |
| R + LuP47B | 3.36 abc | 7.27 bc | 8.11 bcde | 15.38 c |
| R + LuP73B | 3.08 bc | 7.33 bc | 13.1 a | 20.43 ab |
| R + LuP83 | 3.12 bc | 7.16 bc | 7.69 cde | 14.75 cd |

Control 1, only rhizobium RRI128 and no *R. solani*;
Control 2, without rhizobium RRI128 and *R. solani* applied;
Control 3, rhizobium RRI128 and *R. solani* applied; R + RRI128 plus endophytic actinobacteria.

TABLE 8

| | Closest match in Gen Bank using BLASTN | | | |
|---|---|---|---|---|
| | Organism | Accession number | Bits | % Identity |
| LuP3 | *Streptomyces drozdowiczii* NRRL B-24297 | EF654097 | 2620 | 99.40 |
| | *Streptomyces drozdowiczii* NBRC101007 | N R041424 | | 99.40 |
| LuP12A | *Streptomyces ciscaucasicus* NBRC 12872 | AB184208 | 2704 | 99.78 |
| | *Streptomyces canus* NBRC 12752 | AB184118 | | 99.78 |
| LuP30 | NRRL B-3239 | EF178682 | 2728 | 99.90 |
| | *Streptomyces rishiriensis* NBRC 13407 | AB184383 | | 99.90 |
| LuP47B | *Streptomyces ciscaucasicus* NBRC 12872 | AB184208 | 2334 | 99.49 |
| | *Streptomyces canus* NBRC 12752 | AB184118 | | 99.49 |
| EN23 | *Streptomyces badius* NRRL B-2567 | NR_043350.1 | 2590 | 99% |
| EN27 | *Streptomyces parvus* Strain 5j38 | JX013965.1 | 1815 | 94% |
| LuP8 | *Streptomyces ciscaucasicus* NBRC 12872 | NR_041085.1 | 1251 | 99.2% |
| | *Streptomyces canus* NBRC 12752 | NR_112259.1 | 1251 | 99.2% |
| Lu P44 | *Streptomyces ciscaucasicus* NBRC 12872 | NR_041085.1 | 2477 | 99.7% |
| | *Streptomyces canus* NBRC 12752 | NR_112259.1 | 2477 | 99.7% |

TABLE 9

| | Shoot: root | | | Shoot weight DM (mg/plant) | | | Root weight DM (mg/plant) | | |
|---|---|---|---|---|---|---|---|---|---|
| Treatment | A | B | C | A | B | C | A | B | C |
| Single inoculation with *Streptomyces* | | | | | | | | | |
| Control[a] | 1.1 | 1.4 | 1.9 | 19.7 | 79.3 | 173 | 17.8 | 55.8 | 91 |
| EN23 | 1.2 | 2.1* | 2.9** | 19.9 | 103.5* | 215.9* | 17.3 | 48.6 | 75.1* |
| LuP30 | 1.0 | 2.2* | 2.6* | 20.3 | 94.1* | 215.9* | 19.6 | 43.8 | 83.6 |
| LuP47B | 1.2 | 2.6** | 2.7* | 19.7 | 103* | 212* | 17.1 | 39.6* | 78.5 |
| Co-inoculation with *S. meliloti* RRI 128 | | | | | | | | | |
| Control[b] | 1.8 | 2.7 | 2.1 | 229 | 268 | 348 | 129 | 100 | 169 |
| EN23 | 2.1 | 2.3 | 2.5 | 238 | 340* | 436** | 114 | 151* | 172 |
| LuP30 | 3.7** | 2.8 | 2.7* | 283* | 392** | 379* | 76** | 141* | 142* |
| LuP47B | 2.8* | 3.5* | 2.0 | 284* | 365** | 331 | 101* | 109 | 163 |

TABLE 10

| | 4 weeks | | | 7 weeks | | |
|---|---|---|---|---|---|---|
| Treatment | 3 mg N | 25 mg N | 50 mg N | 3 mg N | 25 mg N | 50 mg N |
| RRI 128 | 22a | 24a | 40a | 27a | 47a | 69b |
| RRI 128 + EN23 | 21a | 53b | 52b | 30ab | 51a | 56a |
| RRI 128 + LuP30 | 31b | 51b | 48b | 41c | 57a | 66ab |
| RRI 128 + LuP47B | 24a | 42b | 36a | 37bc | 49a | 71b |

TABLE 11

| Actinobacteria | S. meliloti RRI 128 concentrations (CFU · ml$^{-1}$) | | |
|---|---|---|---|
| | $5 \times 10^2$ | $5 \times 10^4$ | $5 \times 10^6$ |
| | Number of nodules per plant | | |
| Nil | 4.3 ± 0.9 | 7.0 ± 0.9 | 8.8 ± 1.5 |
| LuP30 | 7.0 ± 1.1 | 7.3 ± 2.3 | 8.5 ± 1.9 |
| LuP47B | 9.0 ± 1.8 | 7.8 ± 1.1 | 9.8 ± 2.9 |

TABLE 15

| | ≤10$^3$ cfu/plate | | ≤10$^5$ cfu/plate | | ≤10$^7$ cfu/plate | |
|---|---|---|---|---|---|---|
| Cultures | WSM 1325 | WSM 471 | WSM 1325 | WSM 471 | WSM 1325 | WSM 471 |
| LuP30 | ++ | ++ | ++ | ++ | + | + |
| LuP47B | ++ | ++ | ++ | ++ | + | + |

TABLE 12

| | Shoot:root | | | Shoot weight DM (mg/plant) | | | Root weight DM (mg/plant) | | | Number of nodules (#/plant) | | |
|---|---|---|---|---|---|---|---|---|---|---|---|---|
| Treatment | 10d | 21d | 35d | 10d | 21d | 35d | 10d | 21d | 35d | 10d | 21d | 35d |
| | Single inoculation with Streptomyces | | | | | | | | | | | |
| Controla | 2.4 | 1.9 | 1.8 | 5.8 | 31.0 | 64.9 | 2.4 | 16.2 | 36.5 | 0 | 0 | 0 |
| LuP30 | 2.6 | 1.9 | 1.9 | 5.7 | 30.1 | 67.2 | 2.2 | 16.2 | 36.3 | 0 | 0 | 0 |
| LuP47B | 2.0 | 1.9 | 1.7 | 5.1 | 28.8 | 65.1 | 2.5 | 15.1 | 37.6 | 0 | 0 | 0 |
| | Co-inoculation with S. meliloti RRI 128 | | | | | | | | | | | |
| Controlb | 2.5 | 1.9 | 1.9 | 5.8 | 25.9 | 87.6 | 2.3 | 13.7 | 45.9 | 0 | 18.6 | 30.0 |
| LuP30 | 2.3 | 2.2 | 2.1 | 5.8 | 33.7* | 110.2* | 2.5 | 15.3 | 52.8 | 0 | 24.6* | 48.6* |
| LuP47B | 2.3 | 2.1 | 1.9 | 5.4 | 34.3* | 110.7* | 2.3 | 16.1 | 59.6* | 0 | 22.8* | 37.2 |

TABLE 13

| | 21d | | | 35d | | |
|---|---|---|---|---|---|---|
| Treatment | $^{15}$N | $^{14}$N | Total N | $^{15}$N | $^{14}$N | Total N |
| | Shoot (µg) | | | | | |
| RRI 128 only | 256a | 489a | 745a | 543a | 1732a | 2275a |
| RRI 128 + LuP30 | 312ab | 503a | 816a | 658a | 2564a | 3222b |
| RRI 128 + LuP47B | 343b | 586a | 929a | 648a | 2956b | 3605b |
| | Root (µg) | | | | | |
| RRI 128 only | 102a | 175a | 276a | 279a | 735a | 1014a |
| RRI 128 + LuP30 | 116ab | 184a | 300a | 313ab | 1062ab | 1375ab |
| RRI 128 + LuP47B | 125b | 197a | 322a | 364b | 1280b | 1644b |

TABLE 16

| Treatment | DW of shoot (mg) | DW of root (mg) | Total DW (mg) | Number of nodules | Nodule mass (mg/plant) |
|---|---|---|---|---|---|
| Untreated | 1320$^a$ | 511.8$^a$ | 1760$^a$ | 0$^a$ | 0$^a$ |
| CB 1809 | 2120$^b$ | 515$^a$ | 2640$^b$ | 119$^b$ | 115$^b$ |
| CB 1809 + LuP8 | 2520$^c$ | 717$^b$ | 3240$^c$ | 97$^b$ | 115$^b$ |
| CB 1809 + LuP30 | 2330$^{bc}$ | 614.6$^{ab}$ | 2940$^c$ | 134$^b$ | 139$^c$ |
| CB 1809 + LuP44 | 2170$^b$ | 606.8$^{ab}$ | 2780$^b$ | 109$^b$ | 141$^c$ |
| CB 1809 + LuP47B | 2500$^c$ | 528.2$^a$ | 3030$^c$ | 122$^b$ | 149$^c$ |

TABLE 14

| | Root length (cm) | | Root weight (mg DM/ plant) | | Nodule number (#/plant) | | Total nodule mass (mg) | |
|---|---|---|---|---|---|---|---|---|
| Treatment | 4w | 7w | 4w | 7w | 4w | 7w | 4w | 7w |
| Untreated* | 20a | 30a | 35.0a | 46.0a | 0a | 0a | 0a | 0a |
| WSM 1325 only | 30b | 34ab | 63.5b | 69.8b | 114b | 119b | 7.5b | 8.3b |
| WSM 1325+ LuP30 | 36c | 39b | 71.7c | 70.6b | 127bc | 168c | 9.3c | 11.2c |
| WSM 1325 + LuP47B | 29b | 31a | 59.6b | 79.3b | 138c | 175c | 7.9b | 11.7c |

TABLE 17

| Treatment | Copper (µg) | Iron (µg) | Magnesium (mg) | Phosphorous (mg) | Sodium (mg) | Nitrogen (mg) |
|---|---|---|---|---|---|---|
| Untreated | 13.8$^a$ | 94$^a$ | 7.1$^a$ | 2.8$^a$ | 153$^a$ | 13.2$^a$ |
| CB 1809 | 25.6$^{bc}$ | 162$^b$ | 9.5$^b$ | 2.9$^a$ | 499$^{cd}$ | 49.8$^b$ |
| CB 1809+ LuP8 | 23.3$^{bc}$ | 203$^c$ | 11.1$^{bc}$ | 3.3$^{ab}$ | 404$^c$ | 61.6$^c$ |
| CB 1809 + LuP30 | 23.9$^{bc}$ | 208$^c$ | 10.8$^{bc}$ | 3.2$^{ab}$ | 577$^d$ | 59.8$^{bc}$ |
| CB 1809 + LuP44 | 24.5$^{bc}$ | 180$^{bc}$ | 10.5$^{bc}$ | 3.1$^{ab}$ | 496$^{cd}$ | 51.9$^{bc}$ |
| CB 1809 + LuP47B | 27.5$^c$ | 214$^c$ | 12.0$^c$ | 3.6$^b$ | 559$^d$ | 63.1$^c$ |

TABLE 18

| Treatment | H of shoot (cm) | DW of shoot (g) | DW of root (g) | No of nodules (#/plant) | Total nodule mass (mg) |
|---|---|---|---|---|---|
| Untreated | 25.7a | 0.88a | 0.41a | 0a | 0.0a |
| Rhi only | 30.7a | 1.10ab | 0.39a | 86b | 91.5bc |
| Rhi + LuP8 | 34.8ab | 1.38bc | 0.39a | 80b | 140.7d |
| Rhi + LuP30 | 30.4a | 1.12ab | 0.37a | 67b | 85.5bc |
| Rhi + LuP44 | 34.0ab | 1.09ab | 0.37a | 71b | 89.3bc |
| Rhi + LuP47B | 42.3b | 1.26abc | 0.34a | 85b | 109.8bc |
| Rhi + B | 29.4a | 1.06ab | 0.43a | 91b | 115.9c |
| N | 30.0a | 1.58c | 0.58b | 0a | 0.0a |

| Treatment | No of Pods (#/plant) | FW of pods (g) | DW of pod + seed (g) | No seeds (#/plant) | DW of seed (g) | Total mass of shoot and pods (g) |
|---|---|---|---|---|---|---|
| Untreated | 2.5a | 1.3a | 0.34a | 5.33a | 0.07a | 1.22a |
| Rhi only | 5.0bc | 3.7b | 0.92bcd | 9.13b | 0.30b | 2.02bc |
| Rhi +LuP8 | 6.1c | 4.6c | 1.12d | 12.38c | 0.36bc | 2.50d |
| Rhi +LuP30 | 4.5bc | 3.7b | 0.83b | 9.75bc | 0.31b | 1.95bc |
| Rhi +LuP44 | 5.3bc | 3.7b | 0.95bcd | 10.75bc | 0.31b | 1.81b |
| Rhi + LuP47B | 5.1bc | 4.2bc | 1.06cd | 10.38bc | 0.43c | 2.33cd |
| Rhi + B | 4.3b | 3.8b | 0.88bc | 8.88b | 0.36bc | 1.94bc |
| N | 6.0bc | 4.7c | 1.09d | 10.5bc | 0.44c | 2.68d |

TABLE 19

| | Nodule # #/plant | Nodule weight mg/ plant | Pod # # per 10 plants | Peak Biomass g per 10 plants | Nodule # #/plant | Nodule weight mg/ plant | Pod # # per 10 plants | Peak Biomass g per 10 plants |
|---|---|---|---|---|---|---|---|---|
| | Riverton SA | | | | Hart SA | | | |
| No inoculation | 36 | 6.1 | 76 | 165 | 45 | 7.1 | 80 | 149 |
| WSM1455 (Group F) | 32 | 9.3 | 85 | 182 | 56 | 8.2 | 106* | 184 |
| Actino bacteria (Lup47b) | 26 | 4.7 | 109 | 229* | 47 | 7.2 | 104* | 193* |
| L.S.D. (P = 0.05) | NS | NS | NS | 38 | NS | NS | 19 | 43 |
| | Pimpinio Vic | | | | Mean of all sites | | | |
| No inoculation | 29 | 12.5 | 8 | 75 | 36 | 9.0 | 50 | 124 |
| WSM1455 (Group F) | 28 | 14.8 | 7 | 75 | 37 | 11.2 | 60* | 140 |
| Actino bacteria (Lup47b) | 58* | 9.9 | 4 | 91 | 45 | 7.5 | 65* | 163* |
| L.S.D. (P = 0.05) | 12 | NS | NS | NS | NS | NS | 10 | 18 |

The invention claimed is:

1. A method for enhancing at least one growth parameter of a leguminous plant grown from a leguminous seed, the method comprising co-inoculating the leguminous seed with:
   a. at least one rhizobial microorganism; and
   b. at least one *Streptomyces* microorganism comprising a 16S rRNA gene nucleotide sequence which is at least 98% identical to one or more of: SEQ ID NO: 5 and SEQ ID NO: 8;
   wherein the plant grown from the co-inoculated leguminous seed exhibits at least one enhanced growth parameter relative to a leguminous plant grown from a seed of the same taxon that has not been co-inoculated and wherein the co-inoculation comprises coating the leguminous seed with a first formulation comprising at least about 200 individual cells of the *Streptomyces* microorganism.

2. The method of claim 1, wherein the rhizobial microorganism is a *Rhizobium* sp.

3. The method of claim 1, wherein the 16S rRNA gene nucleotide sequence is at least 98% identical to SEQ ID NO: 5.

4. The method of claim 1, wherein the first formulation comprises about 200-2000 individual cells of the *Streptomyces* microorganism.

5. The method of claim 1, wherein the first formulation comprises an additive.

6. The method of claim 5, wherein the additive is xanthan gum, and wherein the amount of xanthan gum in the first formulation is 0.3% w/v.

7. The method of claim 1, wherein the co-inoculating comprises co-inoculating the seed with a second formulation comprising the rhizobial microorganism.

8. The method of claim 7, wherein the second formulation comprises about less than $5 \times 10^4$ CFUs of the rhizobial microorganism, and wherein the leguminous plant grown from the leguminous seed comprises about 20% more nodules than a control plant grown from a control seed of the same taxon that is singly inoculated with the same amount of the rhizobial microorganism.

9. The method of claim 7, wherein the second formulation comprises about $5 \times 10^2$ CFUs of the rhizobial microorganism, and wherein a leguminous plant grown from the leguminous seed comprises about 50% more nodules than a control plant grown from a control seed of the same taxon that is singly inoculated with the same amount of the rhizobial microorganism.

10. The method of claim 1, wherein the rhizobial microorganism is a *Sinorhizobium* sp.

11. The method of claim 1, wherein the rhizobial microorganism is a *Bradyrhizobium* sp.

12. The method of claim 1, wherein 16S rRNA gene nucleotide sequence is 100% identical to SEQ ID NO: 5.

13. The method of claim 1, wherein the leguminous seed is a seed of a leguminous plant selected from the group consisting of: *Medicago* sp., *Trifolium* sp., *Pisum* sp., and *Glycine* sp.

14. The method of claim 1, wherein the 16S rRNA gene nucleotide sequence is at least 98% identical to SEQ ID NO: 8.

15. The method of claim 1, wherein the 16S rRNA gene nucleotide sequence is 100% identical to SEQ ID NO: 8.

16. The method of claim 1, wherein the growth parameter is a number and/or mass of nodules of the leguminous plant.

17. The method of claim 1, wherein the growth parameter is a number and/or mass of seed pods and/or seed produced by the leguminous plant.

18. The method of claim 1, wherein the growth parameter is a concentration and/or amount of a nutrient in the leguminous plant.

19. The method of claim 18, wherein the nutrient is selected from: Boron, Calcium, Copper, Magnesium, Manganese, Phosphorous, Sodium, Sulphur, Nitrogen and/or Zinc.

20. The method of claim 1, wherein the growth parameter is a germination rate of a leguminous plant.

21. The method of claim 1, wherein the leguminous plant is selected from the group consisting of: *Medicago* sp., *Trifolium* sp., *Pisum* sp., and *Glycine* sp.

22. The method of claim 1, wherein the leguminous plant is exposed to a pathogen and, when exposed to the pathogen, the co-inoculated leguminous plant has at least one enhanced growth parameter relative to a leguminous plant of the same taxon that has not been co-inoculated.

23. The method of claim 22, wherein the pathogen is a root pathogen.

24. The method of claim 22, wherein the pathogen is a fungal pathogen.

25. The method of claim 24, wherein the pathogen is a *Rhizoctonia* sp.

26. A leguminous plant reproductive material co-inoculated with:
   a. at least one rhizobial microorganism; and
   b. at least one *Streptomyces* microorganism selected from *Streptomyces* sp. LuP30 as deposited under NMI accession number V13/030101 or *Streptomyces* sp. LuP47B as deposited under NMI accession number V13/030100,
   wherein the leguminous plant reproductive material is coated with a first formulation comprising at least about 200 individual cells of the *Streptomyces* microorganism.

27. A method comprising:
co-inoculating a leguminous seed with:
- a. at least one rhizobial microorganism; and
- b. at least one *Streptomyces* microorganism comprising a 16S rRNA gene nucleotide sequence which is at least 98% identical to one or more of: SEQ ID NO: 5 and SEQ ID NO: 8;

wherein the co-inoculation comprises coating the leguminous seed with a first formulation comprising at least about 200 individual cells of the *Streptomyces* microorganism.

\* \* \* \* \*